(12) United States Patent
Narquizian et al.

(10) Patent No.: US 9,079,919 B2
(45) Date of Patent: Jul. 14, 2015

(54) SPIRO-[1,3]-OXAZINES AND SPIRO-[1,4]-OXAZEPINES AS BACE1 AND/OR BACE2 INHIBITORS

(75) Inventors: Robert Narquizian, Zaessingue (FR); Emmanuel Pinard, Linsdorf (FR); Wolfgang Wostl, Grenzach-Wyhlen (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 283 days.

(21) Appl. No.: 13/476,094

(22) Filed: May 21, 2012

(65) Prior Publication Data
US 2012/0302549 A1    Nov. 29, 2012

(30) Foreign Application Priority Data
May 27, 2011    (EP) ..................................... 11167835

(51) Int. Cl.
| | | |
|---|---|---|
| A61K 31/537 | (2006.01) |
| C07D 265/08 | (2006.01) |
| C07D 413/12 | (2006.01) |
| C07D 413/14 | (2006.01) |
| C07D 498/10 | (2006.01) |

(52) U.S. Cl.
CPC ................................... C07D 498/10 (2013.01)

(58) Field of Classification Search
CPC .. A61K 31/537; C07D 265/08; C07D 413/12; C07D 413/14
USPC .............................. 514/228.8; 540/71; 544/71
See application file for complete search history.

(56) References Cited

FOREIGN PATENT DOCUMENTS

| EP | 2151435 | 2/2010 |
|---|---|---|
| WO | 2008/030412 | 3/2008 |
| WO | 2010/021680 | 2/2010 |
| WO | 2010/073078 | 7/2010 |

OTHER PUBLICATIONS

Maugeri et al., "Srpski Arhivza Celokupno Lekarstuo" ((Suppl 1)), 138:50-52 ( 2010).
Woodard-Grice et al., "J. Biol. Chem." 283(39):26364-26373 (2008).
Desnues et al., "Clinical & Vaccine Immunology" 13(2):170-178 (2006).
Kuhn et al., "J. Biol. Chem." 282(16):11982-11995 (2007).
Fukui et al., Cell Metab. 2:373-384 ( 2005).
Akpinar et al., Cell Metab. 2:385-397 ( 2005).
Talantov et al., "Clin. Cancer Res." 11:7234-7242 (2005).
Finzi et al., "Ultrastruct. Pathol." 32(6):246-251 ( 2008).
Basset et al., "Scandinavian Journal of Immunology" 51(3):307-311 (2000).
Hodges et al., Hum. Mol. Genet. 15:965-977 (2006).
Wild et al., "Diabetes Care" 27(5):1047-1053 (2004).
Toegel et al., "Osteoarthritis & Cartilage" 18(2):240-248 (2010).
Vassar et al., Bace, Science 286:735 (1999).
Greenberg et al., Ann. Neurol. 57:664-678 (2005).
Sugimoto et al., "J. Biol. Chem." 282(48):34896-34903 (2007).
Roberds et al., Hum. Mol. Genet. 10(12):1317-1324 (2001).
Hedlund et al., Cancer Research 68(2):388-394 (2008).
Lagos et al., "Blood" 109(4):1550-1558 (2007).
Selkoe et al., "Annual Review Cell Biology" 10:373-403 (1994).
Li et al., "Aging Cell" 5(2):153-165 (2006).
Hardy et al., "Science" 297 (5580):353-356 (2002).
Prentki et al., J. Clin. Investig. 116(7):1802-1812 (2006).
Kiljanski et al., "Thyroid" 15(7):645-652 (2005).
Gatchel et al., Proc. Natl. Acad. Sci. USA 105:1291-1296 (2008).
McConlogue et al., "J. Biol. Chem." 282(36):26326-26334 (2007).
Kondoh et al., "Breast Cancer & Research Treatment" 78(1):37-44 (2003).
Zimmet et al., Nature 414:782-787 (2001).
Kihara et al., Proc. Natl. Acad. Sci. USA 106:21807-21812 (2009).
Hussain et al., Mol. Cell Neurosci. 16:609-619 ( 2000).
Hoffmeister et al., "Journal of the Pancreas" 10(5):501-506 (2009).
Kim et al., "Neurobiology of Disease" 22(2):346-356 (2006).
Koistinen et al., "Muscle & Nerve" 34(4):444-450 (2006).
Barbiero et al., Exp. Neurol. 182:335-345 (2003).
Baggio et al., Annu. Rev. Med. 57:265-281 (2006).
Merten et al., "Zeitschrift fur Kardiologie" ((English language Summary is attached to the reference)), 93(11):855-863 (2004).
Grewal et al., Mol. Cell Biol. 26:4970-4981 (2006).
Vattemi et al., "Lancet" ((9297)), 358:1962-1964 (2001).
Luo et al., "Nature Neuroscience" 3:231-232 (2001).
Lichtenthaler et al., "J. Biol. Chem." 278(49):48713-48719 (2003).
The letter of opposition in the corresponding Costa Rican Application No. 2013-0580, which was notified by the Costa Rican Patent Office on Mar. 12, 2014.

(Continued)

*Primary Examiner* — Brenda Coleman

(57) ABSTRACT

The present invention provides spiro-[1,3]-oxazines and spiro-[1,4]-oxazepines of formula I

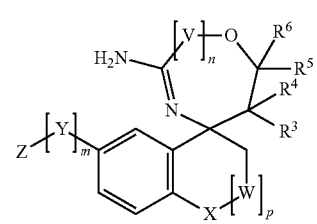

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

22 Claims, No Drawings

(56) References Cited

OTHER PUBLICATIONS

Hilpert et al., 'β-Secretase (BACE1) Inhibitors with High in Vivo Efficacy Suitable for Clinical Evaluation in Alzheimer's Disease,' J. Med. Chem. Apr. 16, 2013, 56, 3980-3995.

Lima et al., "Bioisosterism: a useful strategy for molecular modification and drug design," Curr Med Chem. 2005:12(1):23-49.

Patani et al., "Bioisosterism: A Rational Approach in Drug Design," Chem.Ref. (1996), vol. 96, pp. 3147-3176.

The Written Opinion by the Intellectual Property Office of Singapore, issued on Mar. 23, 2015, in the corresponding Singapore Application No. 2013082607.

SPIRO-[1,3]-OXAZINES AND SPIRO-[1,4]-OXAZEPINES AS BACE1 AND/OR BACE2 INHIBITORS

PRIORITY TO RELATED APPLICATION(S)

This application claims the benefit of European Patent Application No. 11167835.5, filed May 27, 2011, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580:353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop Aβ-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the AD peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & CJ Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

FIELD OF THE INVENTION

The present invention provides spiro-[1,3]-oxazines and spiro-[1,4]-oxazepines having BACE1 and/or BACE2 inhibitory properties, their manufacture, pharmaceutical compositions containing them and their use as therapeutically active substances.

SUMMARY OF THE INVENTION

The present invention provides novel compounds of formula I, their manufacture, pharmaceutical compositions based on a compound in accordance with the invention and their production as well as the use of compounds of formula I in the control or prevention of illnesses such as Alzheimer's disease and type 2 diabetes. The novel compounds of formula I have improved pharmacological properties.

The present invention provides a compound of formula I,

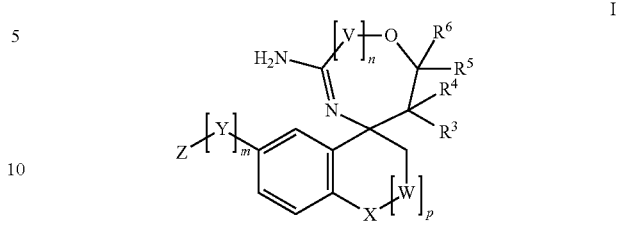

wherein the substituents and variables are as described below and in the claims, or a pharmaceutically acceptable salt thereof.

The present compounds have Asp2 (β-secretase, BACE1 or Memapsin-2) inhibitory activity and/or BACE2 inhibitory activity. The present compounds having Asp2 (β-secretase, BACE1 or Memapsin-2) inhibitory activity can be used in the therapeutic and/or prophylactic treatment of diseases and disorders characterized by elevated β-amyloid levels and/or β-amyloid oligomers and/or β-amyloid plaques and further deposits, particularly Alzheimer's disease. The present compounds having BACE2 inhibitory activity can be used in the therapeutic and/or prophylactic treatment of diseases and disorders such as type 2 diabetes and other metabolic disorders.

DETAILED DESCRIPTION OF THE INVENTION

The present invention provides a compound of formula I and pharmaceutically acceptable salts thereof, the preparation of the above mentioned compounds, pharmaceutical compositions containing them and their manufacture as well as methods for the therapeutic and/or prophylactic treatment of diseases and disorders which are associated with inhibition of BACE1 and/or BACE2 activity, such as Alzheimer's disease and type 2 diabetes by administering compounds of the invention. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which can be linear or branched, with single or multiple branching, wherein the alkyl group contains 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. The term "$C_{1-3}$-alkyl", alone or in combination with other groups, stands for a hydrocarbon radical which can be linear or branched, wherein the alkyl group contains 1 to 3 carbon atoms. Specific examples are methyl and ethyl, particularly methyl.

The term "cyano-$C_{1-6}$-alkyl", alone or in combination with other groups, refers to $C_{1-6}$-alkyl as defined herein, which is substituted by one or multiple cyano groups, particularly 1-5 cyano groups, more particularly 1 cyano group. Examples are cyano-methyl and the like.

The term "halogen-$C_{1-6}$-alkyl", alone or in combination with other groups, refers to $C_{1-6}$-alkyl as defined herein, which is substituted by one or multiple halogen atoms, particularly 1-5 halogen atoms, more particularly 1-3 halogen atoms, most particularly 1 halogen atom or 3 halogen atoms. The term "halogen-$C_{1-3}$-alkyl", alone or in combination with other groups, refers to $C_{1-3}$-alkyl as defined herein, which is substituted by one or multiple halogen atoms, particularly 1-5 halogen atoms, more particularly 1-3 halogen atoms, most particularly 1 halogen atom or 3 halogen atoms. A particular halogen is fluoro. A particular "halogen-$C_{1-6}$-alkyl" is fluoro-$C_{1-6}$-alkyl, and a particular "halogen-$C_{1-3}$-alkyl" is fluoro-$C_{1-3}$-alkyl. Examples are difluoromethyl, chloromethyl, fluoromethyl and the like. A specific example is trifluoromethyl.

The term "$C_{1-6}$-alkoxy-$C_{1-6}$-alkyl", alone or in combination with other groups, refers to $C_{1-6}$-alkyl, which is substituted by one or multiple $C_{1-6}$-alkoxy as defined herein. Examples are MeO-Me, 1MeO-Et, 2MeO-Et, 1MeO-2EtO-propyl and the like.

The term "cyano", alone or in combination with other groups, refers to N≡C—.

The term "halogen", alone or in combination with other groups, denotes chloro (Cl), iodo (I), fluoro (F) and bromo (Br). Particular "halogen" atoms are Cl and F, specifically F.

The term "heteroaryl", alone or in combination with other groups, refers to an aromatic group of having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl, pyrimidinyl and 1H-pyrazolyl. Specific groups are pyridin-2-yl, pyridin-3-yl, pyridin-4-yl, pyrimidin-5-yl and 1H-pyrazol-5-yl.

The term "aryl" denotes a monovalent aromatic carbocyclic mono- or bicyclic ring system containing 6 to 10 carbon ring atoms. Examples of aryl moieties include phenyl and naphthyl. Particular "aryl" is phenyl.

The term "heterocyclyl", alone or in combination with other groups, denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocyclyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, and dihydropyranyl. A particular "heterocyclyl" is tetrahydrofuranyl.

The term "$C_{1-6}$-alkoxy", alone or in combination with other groups, stands for an —O—$C_{1-6}$-alkyl radical which can be linear or branched, with single or multiple branching, wherein the alkyl group in contains 1 to 6 carbon atoms, for example, methoxy (OMe), ethoxy (OEt, propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" groups are those with 1 to 4 carbon atoms. Specific examples are methoxy and ethoxy.

The term "halogen-$C_{1-6}$-alkoxy", alone or in combination with other groups, refers to $C_{1-6}$-alkoxy as defined herein, which is substituted by one or multiple halogen atoms, in particular fluoro. A particular "halogen-$C_{1-6}$-alkoxy" is fluoro-$C_{1-6}$-alkoxy. Specific groups are difluoromethoxy and trifluoromethoxy.

The term "$C_{2-6}$-alkynyl", alone or in combination with other groups, denotes a monovalent linear or branched hydrocarbon group of 2 to 6 carbon atoms, in particular from 2 to 4 carbon atoms, containing one, two or three triple bonds. Examples of $C_{2-6}$-alkynyl include ethynyl, propynyl and n-butynyl. Specific examples are ethynyl and propynyl.

The term "pharmaceutically acceptable salts" refers to salts that are suitable for use in contact with the tissues of humans and animals. Examples of suitable salts with inorganic and organic acids are, but are not limited to, acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Specific examples are formic acid, trifluoroacetic acid and hydrochloric acid. Particular examples are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), triphenylmethyl (Tr), 4-monomethoxytrityl (MMTr), 4,4-dimethoxy-trityl (DMTr), 4,4',4"-trimethoxytrityl and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

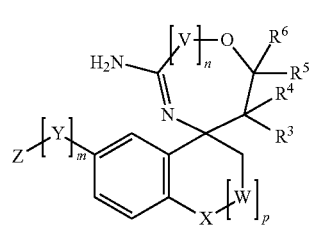

wherein
V is —CR$^{7a}$R$^{7b}$—;
W is —CR$^{2a}$R$^{2b}$—;
X is —CR$^{1a}$R$^{1b}$—; —O—, —S— or —SO$_2$—;
Y —NH—C=O—;
Z is selected from the group consisting of
    heteroaryl,
    heteroaryl substituted by 1-4 substituents individually selected from R$^8$, aryl, and
    aryl substituted by 1-4 substituents individually selected from R$^8$;
R$^{1a}$ is selected from the group consisting of
    hydrogen,
    halogen, and
    C$_{1-6}$-alkyl;
R$^{1b}$ is selected from the group consisting of
    hydrogen,
    halogen, and
    C$_{1-6}$-alkyl;
R$^{2a}$ is selected from the group consisting of
    hydrogen and
    C$_{1-6}$-alkyl;
R$^{2b}$ is selected from the group consisting of
    hydrogen,
    aryl, and
    C$_{1-6}$-alkyl;
or R$^{2a}$ and R$^{2b}$ together with the C to which they are attached form a heterocyclyl;
R$^3$ is selected from the group consisting of
    hydrogen and
    halogen;
R$^4$ is selected from the group consisting of
    hydrogen and
    halogen;

$R^5$ is selected from the group consisting of
  hydrogen and
  $C_{1-6}$-alkyl;
$R^6$ is selected from the group consisting of
  hydrogen and
  $C_{1-6}$-alkyl;
$R^{7a}$ is selected from the group consisting of
  hydrogen and
  $C_{1-6}$-alkyl;
$R^{7b}$ is selected from the group consisting of
  hydrogen and
  $C_{1-6}$-alkyl;
$R^8$ is selected from the group consisting of
  cyano,
  cyano-$C_{1-6}$-alkyl,
  halogen,
  halogen-$C_{1-6}$-alkoxy,
  halogen-$C_{1-6}$-alkyl,
  $C_{1-6}$-alkoxy,
  $C_{1-6}$-alkoxy-$C_{1-6}$-alkyl,
  $C_{2-6}$-alkynyl, and
  $C_{1-6}$-alkyl;
n is 0 or 1;
m is 0 or 1; and
p is 0 or 1;
or pharmaceutically acceptable salts thereof.

A certain embodiment is a compound as described herein, wherein
V is —$CR^{7a}R^{7b}$—;
W is —$CR^{2a}R^{2b}$—;
X is —$CR^{1a}R^{1b}$—, —O—, —S— or —$SO_2$—;
Y —NH—C=O—;
Z is selected from the group consisting of
  heteroaryl,
  heteroaryl substituted by 1-2 substituents individually selected from $R^8$, and
  aryl substituted by 1-2 substituents individually selected from $R^8$;
$R^{1a}$ is selected from the group consisting of
  hydrogen,
  halogen, and
  $C_{1-6}$-alkyl;
$R^{1b}$ is selected from the group consisting of
  hydrogen,
  halogen, and
  $C_{1-6}$-alkyl;
$R^{2a}$ is selected from the group consisting of
  hydrogen and
  $C_{1-6}$-alkyl;
$R^{2b}$ is selected from the group consisting of
  hydrogen,
  phenyl, and
  $C_{1-6}$-alkyl;
or $R^{2a}$ and $R^{2b}$ together with the C to which they are attached form tetrahydropyranyl;
$R^3$ is halogen;
$R^4$ is halogen;
$R^5$ is hydrogen;
$R^6$ is hydrogen;
$R^{7a}$ is hydrogen;
$R^{7b}$ is hydrogen;
$R^8$ is selected from the group consisting of
  cyano,
  halogen,
  halogen-$C_{1-6}$-alkyl, and
  $C_{1-6}$-alkoxy;

n is 0 or 1;
m is 0 or 1;
p is 0 or 1;
or pharmaceutically acceptable salts thereof.

A certain embodiment is a compound as described herein, wherein
V is —$CR^{7a}R^{7b}$—;
W is —$CR^{2a}R^{2b}$—;
X is —$CR^{1a}R^{1b}$—;
Y —NH—C=O—;
Z is selected from the group consisting of
  heteroaryl,
  heteroaryl substituted by 1-2 substituents individually selected from $R^8$, and
  aryl substituted by 1-2 substituents individually selected from $R^8$;
$R^{1a}$ is selected from the group consisting of
  hydrogen,
  halogen, and
  $C_{1-6}$-alkyl;
$R^{1b}$ is selected from the group consisting of
  hydrogen,
  halogen, and
  $C_{1-6}$-alkyl;
$R^{2a}$ is selected from the group consisting of
  hydrogen and
  $C_{1-6}$-alkyl;
$R^{2b}$ is selected from the group consisting of
  hydrogen,
  phenyl, and
  $C_{1-6}$-alkyl;
$R^3$ is halogen;
$R^4$ is halogen;
$R^5$ is hydrogen;
$R^6$ is hydrogen;
$R^{7a}$ is hydrogen;
$R^{7b}$ is hydrogen;
$R^8$ is selected from the group consisting of
  cyano,
  halogen, and
  halogen-$C_{1-6}$-alkyl;
n is 0 or 1;
m is 0 or 1; and
p is 0 or 1;
or pharmaceutically acceptable salts thereof.

A certain embodiment is a compound as described herein, wherein
X is —$CR^{1a}R^{1b}$—;
Y —NH—C=O—;
Z is heteroaryl substituted by $R^8$;
$R^{1a}$ is hydrogen;
$R^{1b}$ is hydrogen;
$R^3$ is halogen;
$R^4$ is halogen;
$R^5$ is hydrogen;
$R^6$ is hydrogen;
$R^{7a}$ is hydrogen;
$R^{7b}$ is hydrogen;
$R^8$ is selected from the group consisting of
  cyano, and
  halogen;
n is 0;
m is 1; and
p is 0;
or pharmaceutically acceptable salts thereof.

A certain embodiment is a compound as described herein, wherein n is 0.

A certain embodiment is a compound as described herein, wherein n is 1.

A certain embodiment is a compound as described herein, wherein m is 0.

A certain embodiment is a compound as described herein, wherein m is 1.

A certain embodiment is a compound as described herein, wherein p is 0.

A certain embodiment is a compound as described herein, wherein p is 1.

A certain embodiment is a compound as described herein, wherein X is —$CR^{1a}R^{1b}$— and $R^{1a}$ and $R^{1b}$ are both hydrogen.

A certain embodiment is a compound as described herein, wherein X is —$CR^{1a}R^{1b}$—.

A certain embodiment is a compound as described herein, wherein $R^{1a}$ is hydrogen.

A certain embodiment is a compound as described herein, wherein $R^{1a}$ is halogen.

A certain embodiment is a compound as described herein, wherein $R^{1a}$ is F.

A certain embodiment is a compound as described herein, wherein $R^{1a}$ is $C_{1-6}$-alkyl.

A certain embodiment is a compound as described herein, wherein $R^{1a}$ is methyl.

A certain embodiment is a compound as described herein, wherein $R^{1b}$ is hydrogen.

A certain embodiment is a compound as described herein, wherein $R^{1b}$ is halogen.

A certain embodiment is a compound as described herein, wherein $R^{1b}$ is F.

A certain embodiment is a compound as described herein, wherein $R^{1b}$ is $C_{1-6}$-alkyl.

A certain embodiment is a compound as described herein, wherein $R^{1b}$ is methyl.

A certain embodiment is a compound as described herein, wherein $R^{2a}$ is $C_{1-6}$-alkyl.

A certain embodiment is a compound as described herein, wherein $R^{2a}$ is methyl.

A certain embodiment is a compound as described herein, wherein $R^{2a}$ is hydrogen.

A certain embodiment is a compound as described herein, wherein $R^{2b}$ is $C_{1-6}$-alkyl.

A certain embodiment is a compound as described herein, wherein $R^{2b}$ is methyl.

A certain embodiment is a compound as described herein, wherein $R^{2b}$ is hydrogen.

A certain embodiment is a compound as described herein, wherein $R^{2b}$ is aryl.

A certain embodiment is a compound as described herein, wherein $R^{2b}$ is phenyl.

A certain embodiment is a compound as described herein, wherein $R^{2a}$ and $R^{2b}$ form together with the C to which they are attached form heterocyclyl.

A certain embodiment is a compound as described herein, wherein $R^{2a}$ and $R^{2b}$ together with the C to which they are attached form tetrahydropyranyl.

A certain embodiment is a compound as described herein, wherein X is —O—.

A certain embodiment is a compound as described herein, wherein X is —S—.

A certain embodiment is a compound as described herein, wherein X is —$SO_2$—.

A certain embodiment is a compound as described herein, wherein p is 1, W is —$CR^{2a}R^{2b}$— and $R^{2a}$ and $R^{2b}$ are both hydrogen.

A certain embodiment is a compound as described herein, wherein V is —$CR^{7a}R^{7b}$— and $R^{7a}$ and $R^{7b}$ are both hydrogen.

A certain embodiment is a compound as described herein, wherein V is —$CR^{7a}R^{7b}$—.

A certain embodiment is a compound as described herein, wherein $R^{7a}$ is hydrogen.

A certain embodiment is a compound as described herein, wherein $R^{7b}$ is hydrogen.

A certain embodiment is a compound as described herein, wherein W is —$CR^{2a}R^{2b}$—.

A certain embodiment is a compound as described herein, wherein $R^3$ is halogen.

A certain embodiment is a compound as described herein, wherein $R^3$ is F.

A certain embodiment is a compound as described herein, wherein $R^4$ is halogen.

A certain embodiment is a compound as described herein, wherein $R^4$ is F.

A certain embodiment is a compound as described herein, wherein $R^5$ is hydrogen.

A certain embodiment is a compound as described herein, wherein $R^6$ is hydrogen.

A certain embodiment is a compound as described herein, wherein Y is —NH—C=O—.

A certain embodiment is a compound as described herein, wherein Z is heteroaryl substituted by halogen or cyano.

A certain embodiment is a compound as described herein, wherein Z is 2-chloropyridinyl, 3,5-dichlorophenyl, 3,5-dichloropyridinyl, 3-cyano-phenyl, 4-chloro-1H-pyrazoleyl, 5-chloropyridinyl, 5-chloropyridinyl, 5-cyanopyridinyl, 5-cyanopyridinyl, 5-fluoropyridinyl, 5-fluoropyridinyl, 5-methoxypyridinyl, 5-trifluoromethylpyridinyl or pyrimidinyl.

A certain embodiment is a compound as described herein, wherein Z is 2-chloropyridin-4-yl, 3,5-dichlorophenyl, 3,5-dichloropyridin-2-yl, 3-cyano-phenyl, 4-chloro-1H-pyrazole-5-yl, 5-chloropyridin-2-yl, 5-chloropyridin-3-yl, 5-cyanopyridin-2-yl, 5-cyanopyridin-3-yl, 5-fluoropyridin-2-yl, 5-fluoropyridin-3-yl, 5-methoxypyridin-3-yl, 5-trifluoromethylpyridin-2-yl or pyrimidin-5-yl.

A certain embodiment is a compound as described herein, wherein Z is 5-cyanopyridin-2-yl, 5-chloropyridin-2-yl, 5-chloropyridin-3-yl or 5-fluoropyridin-2-yl.

A certain embodiment is a compound as described herein, wherein Z is heteroaryl.

A certain embodiment is a compound as described herein, wherein Z is pyrimidinyl.

A certain embodiment is a compound as described herein, wherein Z is heteroaryl substituted by 1-2 substituents individually selected from $R^8$.

A certain embodiment is a compound as described herein, wherein Z is 1H-pyrazolyl, pyridinyl or pyrimidinyl.

A certain embodiment is a compound as described herein, wherein Z is 1H-pyrazol-5-yl, pyridin-2-yl, pyridin-3-yl, pyridin-4-yl or pyrimidin-5-yl.

A certain embodiment is a compound as described herein, wherein Z is aryl.

A certain embodiment is a compound as described herein, wherein Z is aryl substituted by 1-4 substituents individually selected from $R^8$.

A certain embodiment is a compound as described herein, wherein Z is phenyl substituted by 1-2 substituents individually selected from chloro and cyano.

A certain embodiment is a compound as described herein, wherein $R^8$ is cyano.

A certain embodiment is a compound as described herein, wherein $R^8$ is halogen.

A certain embodiment is a compound as described herein, wherein $R^8$ is chloro.

A certain embodiment is a compound as described herein, wherein $R^8$ is fluoro.

A certain embodiment is a compound as described herein, wherein $R^8$ is halogen-$C_{1-6}$-alkyl.

A certain embodiment is a compound as described herein, wherein $R^8$ is trifluoromethyl.

A certain embodiment is a compound as described herein, wherein $R^8$ is $C_{1-6}$-alkoxy.

A certain embodiment is a compound as described herein, wherein $R^8$ is methoxy.

A certain embodiment is a compound as described herein, selected from the group consisting of (R)-7-(5-chloropyridin-3-yl)-5',5'-difluoro-3,4,5',6'-tetrahydro-2H-spiro[naphthalene-1,4'-[1,3]oxazin]-2'-amine, (2'R,4R)-6'-(5-chloropyridin-3-yl)-5,5-difluoro-5,5'',6,6''-tetrahydro-4''H-dispiro[1,3-oxazine-4,4'-chromene-2',3''-pyran]-2-amine formate, (2RS,4R)-5',5'-difluoro-2-phenyl-6-(pyrimidin-5-yl)-5',6'-dihydrospiro[chroman-4,4'-[1,3]oxazin]-2'-amine, (2RS,4R)-6-(3,5-dichlorophenyl)-5',5'-difluoro-2-phenyl-5',6'-dihydrospiro[chroman-4,4'-[1,3]oxazin]-2'-amine, (2RS,4R)-6-(3,5-dichlorophenyl)-6',6'-difluoro-2-phenyl-6',7'-dihydro-2'H-spiro[chroman-4,5'-[1,4]oxazepin]-3'-amine, (2RS,4R)-6-(5-chloropyridin-3-yl)-5',5'-difluoro-2-phenyl-5',6'-dihydrospiro[chroman-4,4'-[1,3]oxazin]-2'-amine, (2RS,4R)-6-(5-chloropyridin-3-yl)-6',6'-difluoro-2-phenyl-6',7'-dihydro-2'H-spiro[chroman-4,5'-[1,4]oxazepin]-3'-amine, (2RS,4R)-6',6'-difluoro-2-phenyl-6-(pyrimidin-5-yl)-6',7'-dihydro-2'H-spiro[chroman-4,5'-[1,4]oxazepin]-3'-amine, (2'S,4R)-6'-(5-chloropyridin-3-yl)-5,5-difluoro-5,5'',6,6''-tetrahydro-4''H-dispiro[1,3-oxazine-4,4'-chromene-2',3''-pyran]-2-amine formate, (R)-3-(2'-Amino-5',5'-difluoro-2,3,5',6'-tetrahydrospiro[indene-1,4'-[1,3]oxazine]-6-yl)benzonitrile, (R)-4,4,5',5'-tetrafluoro-7-(5-fluoropyridin-3-yl)-3,4,5',6'-tetrahydro-2H-spiro[naphthalene-1,4'-[1,3]oxazin]-2'-amine, (R)-5-(2'-amino-4,4,5',5'-tetrafluoro-3,4,5',6'-tetrahydro-2H-spiro[naphthalene-1,4'-[1,3]oxazine]-7-yl)nicotinonitrile, (R)-5-(2'-amino-5',5'-difluoro-2,3,5',6'-tetrahydrospiro[indene-1,4'-[1,3]oxazine]-6-yl)nicotinonitrile, (R)-5-(2'-amino-5',5'-difluoro-3,4,5',6'-tetrahydro-2H-spiro[naphthalene-1,4'-[1,3]oxazine]-7-yl)nicotinonitrile, (R)-5',5'-difluoro-6-(5-methoxypyridin-3-yl)-5',6'-dihydrospiro[chroman-4,4'-[1,3]oxazin]-2'-amine, (R)-5',5'-difluoro-6-(pyrimidin-5-yl)-2,3,5',6'-tetrahydrospiro[indene-1,4'-[1,3]oxazin]-2'-amine, (R)-5',5'-difluoro-6-(pyrimidin-5-yl)-5',6'-dihydrospiro[chroman-4,4'-[1,3]oxazin]-2'-amine, (R)-6-(2-chloropyridin-4-yl)-5',5'-difluoro-2,3,5',6'-tetrahydrospiro[indene-1,4'-[1,3]oxazin]-2'-amine, (R)-6-(3,5-dichlorophenyl)-5',5'-difluoro-2,3,5',6'-tetrahydrospiro[indene-1,4'-[1,3]oxazin]-2'-amine, (R)-6-(3,5-dichlorophenyl)-5',5'-difluoro-5',6'-dihydrospiro[chroman-4,4'-[1,3]oxazin]-2'-amine, (R)-6-(3,5-dichlorophenyl)-6',6'-difluoro-6',7'-dihydro-2'H-spiro[chroman-4,5'-[1,4]oxazepin]-3'-amine, (R)-6-(5-chloropyridin-3-yl)-5',5'-difluoro-2,2-dimethyl-5',6'-dihydrospiro[chroman-4,4'-[1,3]oxazin]-2'-amine, (R)-6-(5-chloropyridin-3-yl)-5',5'-difluoro-2,3,5',6'-tetrahydrospiro[indene-1,4'-[1,3]oxazin]-2'-amine, (R)-6'-(5-chloropyridin-3-yl)-5,5-difluoro-5,6-dihydrospiro[[1,3]oxazine-4,4'-thiochroman]-2-amine, (R)-6-(5-chloropyridin-3-yl)-5',5'-difluoro-5',6'-dihydrospiro[chroman-4,4'-[1,3]oxazin]-2'-amine, (R)-6-(5-chloropyridin-3-yl)-6',6'-difluoro-6',7'-dihydro-2'H-spiro[chroman-4,5'-[1,4]oxazepin]-3'-amine, (R)-7-(5-chloropyridin-3-yl)-4,4,5',5'-tetrafluoro-3,4,5',6'-tetrahydro-2H-spiro[naphthalene-1,4'-[1,3]oxazin]-2'-amine, (R)—N-(2'-amino-5',5'-difluoro-2,2-dimethyl-5',6'-dihydrospiro[chroman-4,4'-[1,3]oxazine]-6-yl)-5-chloropicolinamide, (R)—N-(2'-amino-5',5'-difluoro-2,2-dimethyl-5',6'-dihydrospiro[chroman-4,4'-[1,3]oxazine]-6-yl)-5-cyanopicolinamide, (R)—N-(2'-amino-5',5'-difluoro-2,3,5',6'-tetrahydrospiro[indene-1,4'-[1,3]oxazine]-6-yl)-5-cyanopicolinamide, (R)—N-(2'-amino-5',5'-difluoro-2,3,5',6'-tetrahydrospiro[indene-1,4'-[1,3]oxazine]-6-yl)-5-chloropicolinamide, (R)—N-(2'-amino-5',5'-difluoro-2,3,5',6'-tetrahydrospiro[indene-1,4'-[1,3]oxazine]-6-yl)-5-fluoropicolinamide, (R)—N-(2'-amino-5',5'-difluoro-2,3,5',6'-tetrahydrospiro[indene-1,4'-[1,3]oxazine]-6-yl)-5-(trifluoromethyl)picolinamide, (R)—N-(2'-amino-5',5'-difluoro-3,4,5',6'-tetrahydro-2H-spiro[naphthalene-1,4'-[1,3]oxazine]-7-yl)-5-chloropicolinamide, (R)—N-(2'-amino-5',5'-difluoro-3,4,5',6'-tetrahydro-2H-spiro[naphthalene-1,4'-[1,3]oxazine]-7-yl)-5-cyanopicolinamide, (R)—N-(2'-amino-5',5'-difluoro-4,4-dimethyl-3,4,5',6'-tetrahydro-2H-spiro[naphthalene-1,4'-[1,3]oxazine]-7-yl)-5-cyanopicolinamide, (R)—N-(2-amino-5,5-difluoro-5,6-dihydrospiro[[1,3]oxazine-4,4'-thiochroman]-6'-yl)-5-chloropicolinamide, (R)—N-(2-amino-5,5-difluoro-5,6-dihydrospiro[[1,3]oxazine-4,4'-thiochroman]-6'-yl)-5-cyanopicolinamide, (R)—N-(2'-amino-5',5'-difluoro-5',6'-dihydrospiro[chroman-4,4'-[1,3]oxazine]-6-yl)-5-chloropicolinamide, (R)—N-(2'-amino-5',5'-difluoro-5',6'-dihydrospiro[chroman-4,4'-[1,3]oxazine]-6-yl)-5-cyanopicolinamide, (R)—N-(2'-amino-5',5'-difluoro-5',6'-dihydrospiro[chroman-4,4'-[1,3]oxazine]-6-yl)-4-chloro-1H-pyrazole-5-carboxamide, (R)—N-(3'-amino-6',6'-difluoro-3,4,6',7'-tetrahydro-2H,2'H-spiro[naphthalene-1,5'-[1,4]oxazepine]-7-yl)-5-cyanopicolinamide, (R)—N-(3'-amino-6',6'-difluoro-3,4,6',7'-tetrahydro-2H,2'H-spiro[naphthalene-1,5'-[1,4]oxazepine]-7-yl)-5-chloropicolinamide, (R)—N-(3'-amino-6',6'-difluoro-6',7'-dihydro-2'H-spiro[chroman-4,5'-[1,4]oxazepine]-6-yl)-5-cyanopicolinamide, (R)—N-(3'-amino-6',6'-difluoro-6',7'-dihydro-2'H-spiro[chroman-4,5'-[1,4]oxazepine]-6-yl)-5-chloropicolinamide, (R)—N-(3'-amino-6',6'-difluoro-6',7'-dihydro-2'H-spiro[chroman-4,5'-[1,4]oxazepine]-6-yl)-3,5-dichloropicolinamide, 3-((2RS,4R)-2'-amino-5',5'-difluoro-2-phenyl-5',6'-dihydrospiro[chroman-4,4'-[1,3]oxazine]-6-yl)benzonitrile, 3-((2RS,4R)-3'-amino-6',6'-difluoro-2-phenyl-6',7'-dihydro-2'H-spiro[chroman-4,5'-[1,4]oxazepine]-6-yl)benzonitrile, 3-[(2'R,4R)-2-amino-5,5-difluoro-5,5'',6,6''-tetrahydro-4''H-dispiro[1,3-oxazine-4,4'-chromene-2',3''-pyran]-6'-yl]benzonitrile formate, 5-((2RS,4R)-2'-amino-5',5'-difluoro-2-phenyl-5',6'-dihydrospiro[chroman-4,4'-[1,3]oxazine]-6-yl)nicotinonitrile, 5-((2RS,4R)-3'-amino-6',6'-difluoro-2-phenyl-6',7'-dihydro-2'H-spiro[chroman-4,5'-[1,4]oxazepine]-6-yl)nicotinonitrile, N-((2R or 2S,4R)-2'-amino-5',5'-difluoro-2-phenyl-5',6'-dihydrospiro[chroman-4,4'-[1,3]oxazine]-6-yl)-5-chloropicolinamide, N-((2R or 2S,4R)-2'-amino-5',5'-difluoro-2-phenyl-5',6'-dihydrospiro[chroman-4,4'-[1,3]oxazine]-6-yl)-5-cyanopicolinamide, N-((2R or 2S,4R)-2'-amino-5',5'-difluoro-2-phenyl-5',6'-dihydrospiro[chroman-4,4'-[1,3]oxazine]-6-yl)-5-fluoropicolinamide, N-((2R or 2S,4R)-2'-amino-5',5'-difluoro-2-phenyl-5',6'-dihydrospiro[chroman-4,4'-[1,3]oxazine]-6-yl)-5-(trifluoromethyl)picolinamide, N-((2RS,4R)-3'-amino-6',6'-difluoro-2-phenyl-6',7'-dihydro-2'H-spiro[chroman-4,5'-[1,4]oxazepine]-6-yl)-5-(trifluoromethyl)picolinamide, N-((2RS,4R)-3'-amino-6',6'-difluoro-2-phenyl-6',7'-dihydro-2'H-spiro[chroman-4,5'-[1,4]oxazepine]-6-yl)-5-cyanopicolinamide, N-[(2'R,4R)-2-amino-5,5-difluoro-5,5'',6,6''-tetrahydro-4''H-dispiro[1,3-oxazine-4,4'-chromene-2',3''-pyran]-6'-yl]-5-cyanopyridine-2-carboxamide, N-[(4R)-2-amino-5,5-difluoro-1',1'-dioxido-2',3',5,6-tetrahydrospiro[1,3-oxazine-4,4'-thiochromen]-6'-yl]-5-chloropyridine-2-carboxamide, and N-[(4R)-2-amino-5,5-difluoro-1',1'-dioxido-2',3',5,6-tetrahydrospiro[1,3-oxazine-4,4'-thiochromen]-6'-yl]-5-cyanoopyridine-2-carboxamide, or a pharmaceutical acceptable salt thereof.

A certain embodiment is a compound as described herein, selected from the group consisting of (R)—N-(2'-Amino-5',5'-difluoro-2,3,5',6'-tetrahydrospiro[indene-1,4'-[1,3]oxazine]-6-yl)-5-cyanopicolinamide, (R)-6-(5-Chloropyridin-3-yl)-5',5'-difluoro-5',6'-dihydrospiro[chroman-4,4'-[1,3]oxazin]-2'-amine, (R)—N-(2'-Amino-5',5'-difluoro-2,3,5',6'-tetrahydrospiro[indene-1,4'-[1,3]oxazine]-6-yl)-5-chloropicolinamide, and (R)—N-(2'-Amino-5',5'-difluoro-2,3,5',6'-tetrahydrospiro[indene-1,4'-[1,3]oxazine]-6-yl)-5-fluoropicolinamide, or a pharmaceutical acceptable salt thereof.

A certain embodiment of the invention provides a process as described below,

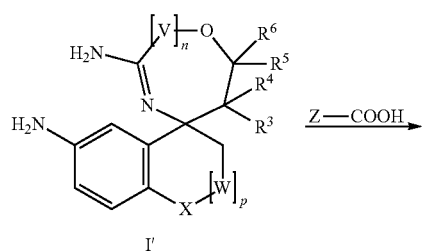

I'

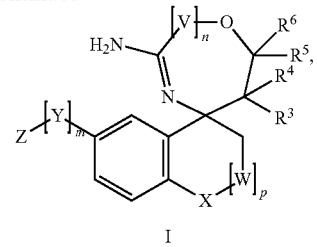

I wherein V, W, Y, Z, n, p, $R^1$, $R^2$, $R^3$, $R^4$, $R^5$ and $R^6$ are as described herein and m is 1.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of type 2 diabetes.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of diabetes.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

A certain embodiment of the invention provides a method for the use in the therapeutic and/or prophylactic treatment of diabetes, which method comprises administering a compound of formula I as described herein to a human being or animal.

A certain embodiment of the invention provides a method for the use in the therapeutic and/or prophylactic treatment of type 2 diabetes, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric forms, e.g. in the following tautomeric form:

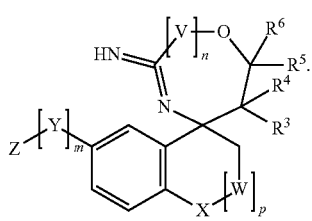

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric center of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Particular examples of isomers of a compound of formula I are compounds of formula Ia wherein the residues have the meaning as described in any of the embodiments.

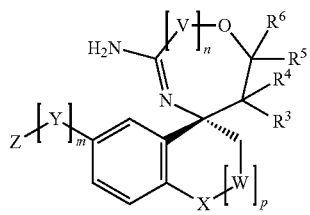

Ia

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

Sulfinyl imines of formula A2, wherein X is —$CR^{1a}R^{1b}$ ($R^{1a}$, $R^{1b}$ are hydrogen, lower alkyl or fluorine) and W is —$CR^{2a}R^{2b}$ (with p=1, $R^{1a}$, $R^{1b}$ are hydrogen), can be prepared in analogy to T. P. Tang & J. A. Ellman, J. Org. Chem. 1999, 64, 12, by condensation of an aryl ketone A1 and a sulfinamide, e.g. an alkyl sulfinamide, most particularly (R)-(+)-tert-butylsulfinamide, in the presence of a Lewis acid such as e.g. a titanium(IV)alkoxide, more particularly titanium(IV)ethoxide in a solvent such as an ether, e.g. diethyl ether or more particularly tetrahydrofuran.

The conversion of the sulfinyl imine A2 to the sulfinamide ester A3 proceeds stereoselectively by the chiral directing group as described by Tang & Ellman. The sulfinyl imine A2 can be reacted in a Reformatsky reaction with a zinc enolate generated from e.g. an alkyl bromodifluoroacetate, particularly ethyl bromodifluoroacetate, and activated zinc powder at ambient to elevated temperature, particularly at 23 to 60° C. in a solvent such as an ether, e.g. diethyl ether or more particularly tetrahydrofuran.

The alcohol of formula A4 can be prepared by the reduction of an ethylester of formula A3 with an alkali hydride, particularly lithium borohydride or lithium aluminium hydride, in a solvent such as an ether, e.g. diethyl ether or more particularly tetrahydrofuran.

Hydrolysis of the chiral directing group in the sulfinamide alcohol of formula A4 to give the aminoalcohol of formula A5 can be accomplished with a mineral acid, e.g. sulfuric acid or particularly hydrochloric acid, in a solvent such as an ether, e.g. diethyl ether, tetrahydrofuran or more particularly 1,4-dioxane.

The aminooxazine of formula A6 can be prepared by reaction of an aminoalcohol of formula A5 with cyanogen bromide in a solvent such as an alcohol, particularly ethanol.

The reduction of derivatives of formula A6, wherein Q is a nitro group, to give anilines of formula A7 can be accomplished by hydrogenation using a catalyst, such as palladium on carbon, in protic solvents, such as alcohols, in particular ethanol or methanol.

Scheme A: Synthesis of compounds of formula I.1 and I.2.

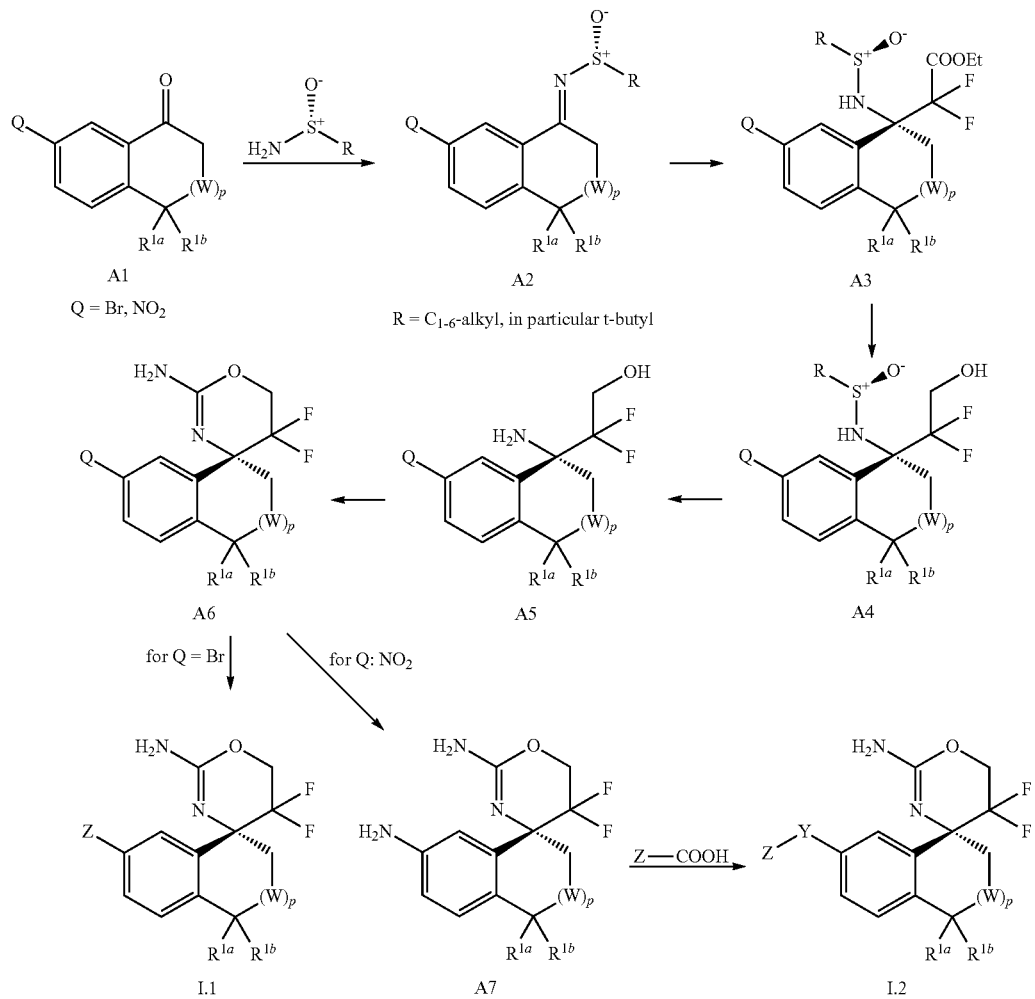

Target amines of formula I.1 can be prepared by palladium-catalyzed cross coupling between compounds of formula A6 and derivatives of formula Z—$R^a$, wherein $R^a$ has the meaning of a boronic acid or ester under conditions (Suzuki-Miyaura-coupling) known to those skilled in the art.

Target amides of formula I.2 can be prepared by selective coupling of anilines of formula A7 and a carboxylic acid of formula Z—COOH with 4-(4,6-dimethoxy[1.3.5]triazin-2-yl)-4-methylmorpholinium chloride hydrate (DMTMM) as the condensating agent in a solvent such as methanol.

Another typical procedure for the preparation of anilines of formula A7 via N-protected intermediates is illustrated in Scheme A.1.

Protection of the amino group in compounds of formula A6, wherein Q is bromine, to produce aryl bromides of formula A6.1 can be performed with triarylmethyl chlorides, such as triphenylmethyl chloride (Tr-Cl), p-methoxyphenyl-diphenylmethyl chloride (MMTr-Cl), di(p-methoxyphenyl)phenylmethyl chloride (DMTr-Cl) or tri(p-methoxyphenyl)methyl chloride (TMTr-Cl), particularly DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of formula A6.1 can be reacted with ammonia equivalents, such as benzophenone imine, in the presence of a suitable transition metal catalyst, such as bis(dibenzylideneacetone)palladium (0) (($dba)_2Pd$) or tris(dibenzylideneacetone) dipalladium (0) (($dba)_3Pd_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula A6.2.

Deprotection of both amino groups in compounds of formula A6.2 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the $P^1$-group.

Then the addition of water to cleave the benzophenone imine and reaction at ambient temperature produces diamines of formula A7.

Scheme A.1: Alternative synthesis of intermediate anilines of formula A7.

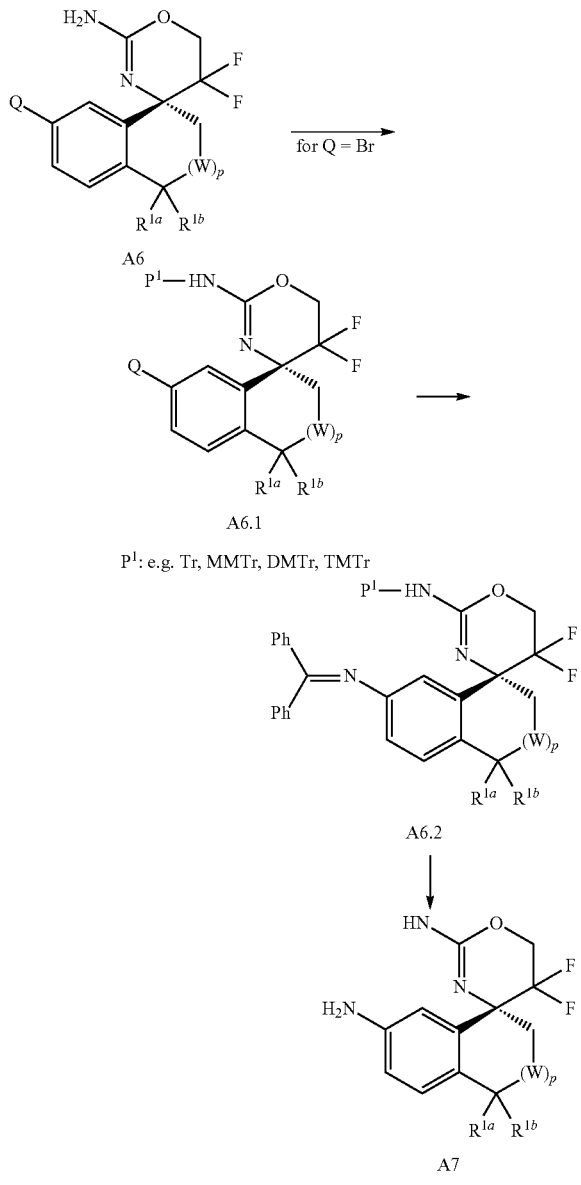

Sulfinyl imines of formula B2, wherein X is O or S and W is —$CR^{2a}R^{2b}$ (with p=1, $R^{2a}$, $R^{2b}$ are hydrogen, lower alkyl, phenyl, or taken together with the C they are attached to form a heterocyclyl) can form a heterocycloalkyl), can be prepared in analogy to T. P. Tang & J. A. Ellman, J. Org. Chem. 1999, 64, 12, by condensation of an aryl ketone B1 and a sulfinamide, e.g. an alkyl sulfinamide, most particularly (R)-(+)-tert-butylsulfinamide, in the presence of a Lewis acid such as e.g. a titanium(IV)alkoxide, more particularly titanium(IV) ethoxide in a solvent such as an ether, e.g. diethyl ether or more particularly tetrahydrofuran.

The conversion of the sulfinyl imine B2 to the sulfinamide ester B3 proceeds stereoselectively by the chiral directing group as described by Tang & Ellman. The sulfinyl imine B2 can be reacted in a Reformatsky reaction with a zinc enolate generated from e.g. an alkyl bromodifluoroacetate, particularly ethyl bromodifluoroacetate, and activated zinc powder at ambient to elevated temperature, particularly at 23 to 60° C. in a solvent such as an ether, e.g. diethyl ether or more particularly tetrahydrofuran.

The alcohol of formula B4 can be prepared by the reduction of an ethylester of formula B3 with an alkali hydride, particularly lithium borohydride or lithium aluminium hydride, in a solvent such as an ether, e.g. diethyl ether or more particularly tetrahydrofuran.

Hydrolysis of the chiral directing group in the sulfinamide alcohol of formula B4 to give the aminoalcohol of formula B5 can be accomplished with a mineral acid, e.g. sulfuric acid or particularly hydrochloric acid, in a solvent such as an ether, e.g. diethyl ether, tetrahydrofuran or more particularly 1,4-dioxane.

The aminooxazine of formula B6 can be prepared by reaction of an aminoalcohol of formula B5 with cyanogen bromide in a solvent such as an alcohol, particularly ethanol.

The reduction of derivatives of formula B6, wherein Q is a nitro group, to give anilines of formula B7 can be accomplished by hydrogenation using a catalyst, such as palladium on carbon, in protic solvents, such as alcohols, in particular ethanol or methanol.

Scheme B: Synthesis of compounds of formula I.3 and I.4.

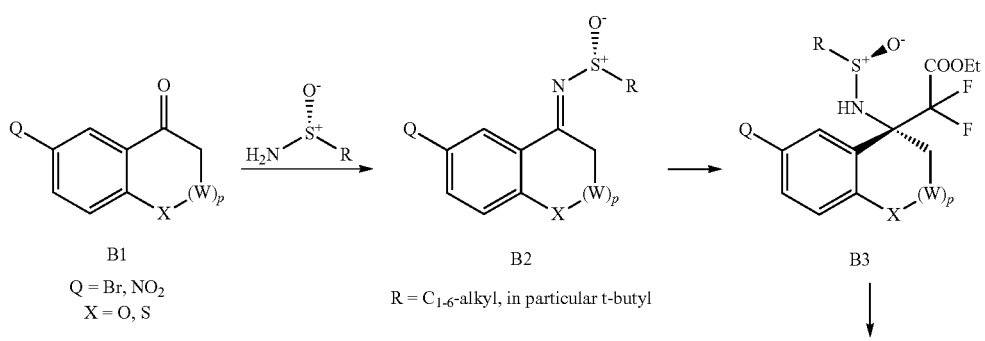

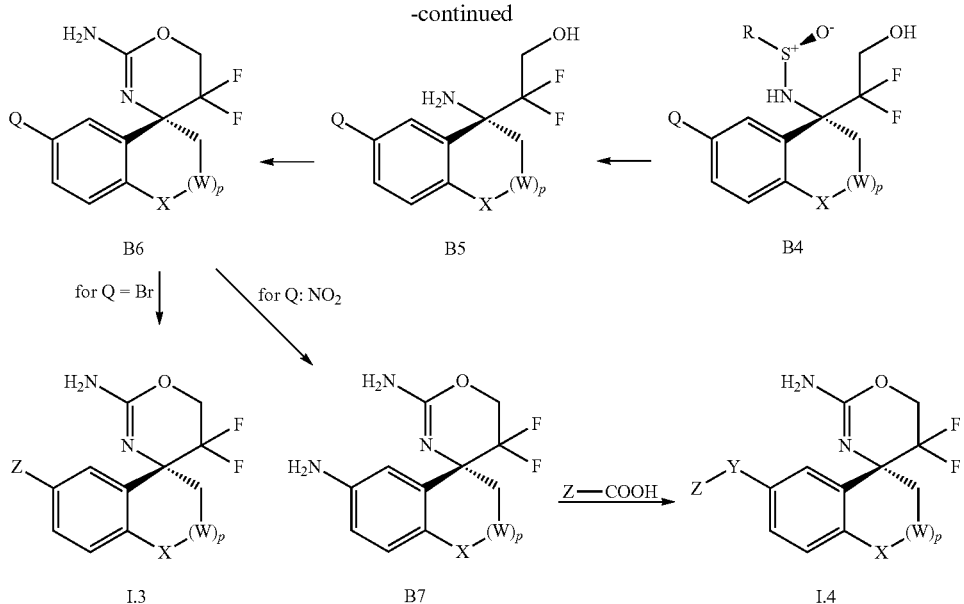

Target amines of formula I.3 can be prepared by palladium-catalyzed cross coupling between compounds of formula B6 and derivatives of formula Z—$R^a$, wherein $R^a$ has the meaning of a boronic acid or ester under conditions (Suzuki-Miyaura-coupling) known to those skilled in the art.

Target amides of formula I.4 can be prepared by selective coupling of anilines of formula B7 and a carboxylic acid of formula Z—COOH with 4-(4,6-dimethoxy[1.3.5]triazin-2-yl)-4-methylmorpholinium chloride hydrate (DMTMM) as the condensating agent in a solvent such as methanol.

Target amides of formula I.3 or I.4, wherein X is $SO_2$, can be prepared from compounds of formula I.3 or I.4, wherein X is S, by oxidation in inert solvents at temperatures between 0° C. and ambient temperature using e.g. potassium peroxomonosulphate as the oxidizing agent.

Alternatively, anilines of formula B7 can be prepared via N-protected intermediates as illustrated in Scheme B.1.

Protection of the amino group in compounds of formula A6, wherein Q is bromine, to produce aryl bromides of formula B6.1 can be performed with triarylmethyl chlorides, such as triphenylmethyl chloride (Tr-Cl), p-methoxyphenyldiphenylmethyl chloride (MMTr-Cl), di(p-methoxyphenyl)phenylmethyl chloride (DMTr-Cl) or tri(p-methoxyphenyl)methyl chloride (TMTr-Cl), particularly DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of formula B6.1 can be reacted with ammonia equivalents, such as benzophenone imine, in the presence of a suitable transition metal catalyst, such as bis(dibenzylideneacetone)palladium (0) (($dba)_2Pd$) or tris(dibenzylideneacetone) dipalladium (0) (($dba)_3Pd_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula B6.2.

Deprotection of both amino groups in compounds of formula B6.2 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the $P^1$-group. Then the addition of water to cleave the benzophenone imine and reaction at ambient temperature produces diamines of formula B7.

Scheme B.1: Alternative synthesis of intermediate anilines of formula B7.

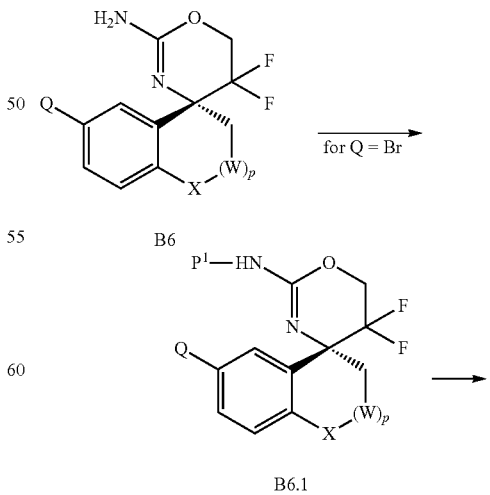

$P^1$: e.g. Tr, MMTr, DMTr, TMTr

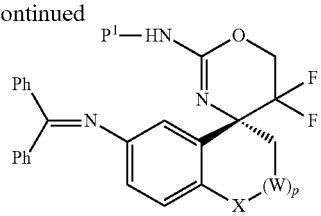

B6.2

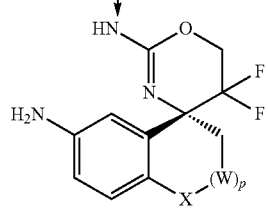

B7

Alkylation of alcohols of formula A4 or B4 to nitriles of formula C1 can be accomplished with a suitable mild base particularly silver(I) oxide in a solvent such as tetrahydrofuran or dichloromethane, more particularly dichloromethane, in the presence of an alkylating catalyst such as tetra-butyl ammonium iodide.

Hydrolysis of the chiral directing group in nitriles of formula C1 to give amino nitriles of formula C2 can be accomplished with a mineral acid, e.g. sulfuric acid or particularly hydrochloric acid in a solvent such as an ether, e.g. diethyl ether or more particularly 1,4-dioxane.

Aminooxazepines of formula C3 can be prepared by the reaction of amino nitriles of formula C2 and trimethyl aluminium in a solvent such as a xylene or toluene, particularly toluene.

The reduction of derivatives of formula C3, wherein Q is a nitro group, to give anilines of formula C4 can be accomplished by hydrogenation using a catalyst, such as palladium on carbon, in protic solvents, such as alcohols, in particular ethanol or methanol.

Scheme C: Synthesis of compounds of formula I.5 and I.6.

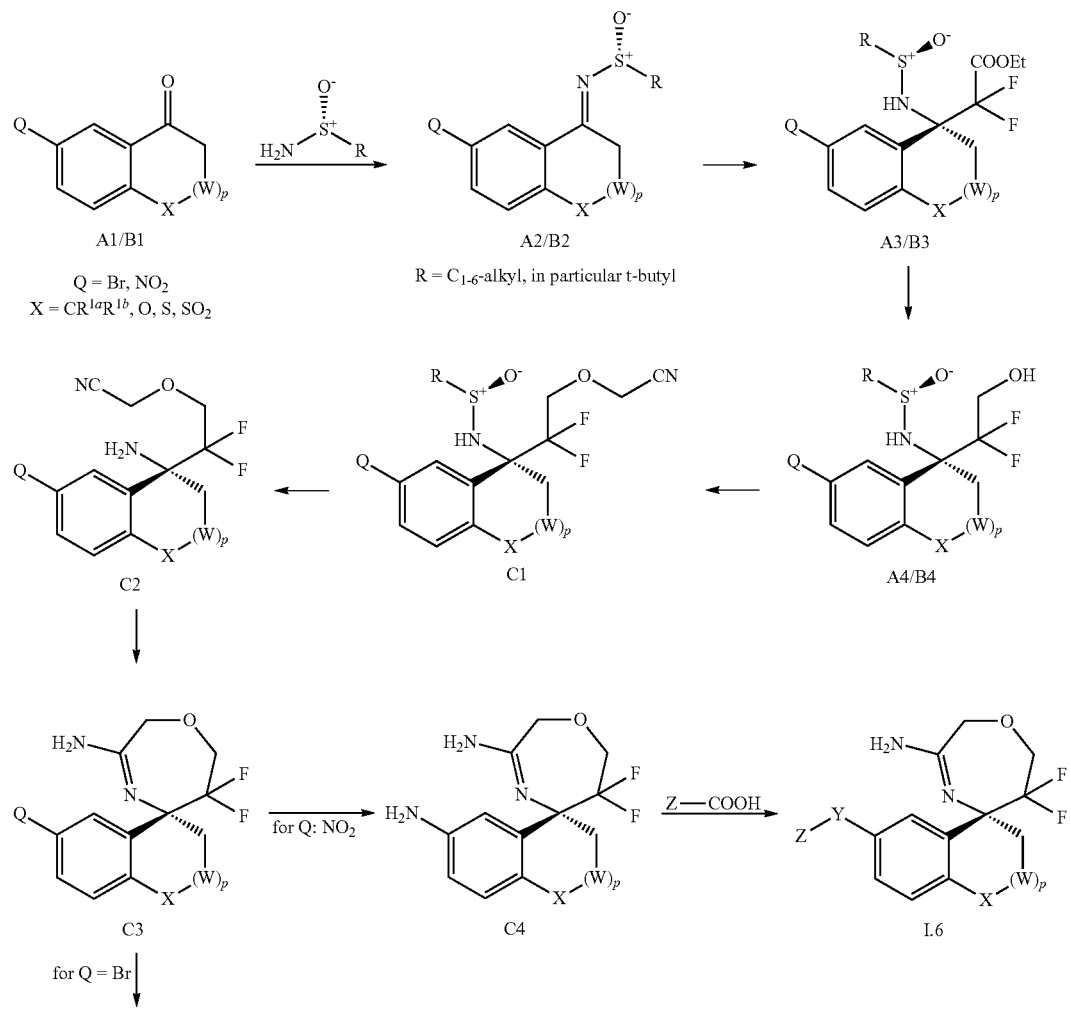

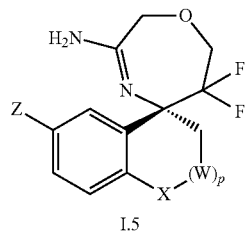

I.5

Target amines of formula I.5 can be prepared by palladium-catalyzed cross coupling between compounds of formula C3 and derivatives of formula Z—$R^a$, wherein $R^a$ has the meaning of a boronic acid or ester under conditions (Suzuki-Miyaura-coupling) known to those skilled in the art.

Target amides of formula I.6 can be prepared by selective coupling of anilines of formula C4 and a carboxylic acid of formula Z—COOH with 4-(4,6-dimethoxy[1.3.5]triazin-2-yl)-4-methylmorpholinium chloride hydrate (DMTMM) as the condensating agent in a solvent such as methanol.

The corresponding pharmaceutically acceptable salts with acids can be obtained by standard methods known to the person skilled in the art, e.g. by dissolving the compound of formula I in a suitable solvent such as e.g. dioxane or tetrahydrofuran (THF) and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatised at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the test given hereinafter.

Cellular Aβ-Lowering Assay:

a) Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume of 1N $H_2SO_4$ the reaction was measured in an ELISA reader at 450 nm wavelength. The concentrations of Aβ in the culture supernatants were calculated from a standard curve obtained with known amounts of pure Aβ peptide.

b) Alternatively, the Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in 1/3 volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat#AL275C).

In a Perkin-Elmer White Optiplate-384 (Cat#6007290), 2 ul culture supernatants were combined with 2 μl of a 10× AlphaLISA Anti-hAβ Acceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The IC50 values were calculated using the Excel XLfit software.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+ Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

$IC_{50}$ values of selected examples, $^{a)}$ and $^{b)}$ indicate the respective cellular assay used

| Exam. | Structure | BACE1 cell act. Aβ40 $IC_{50}$ [μM] | BACE2 cell act. $IC_{50}$ [μM] |
|---|---|---|---|
| 1 | 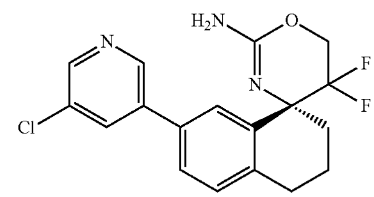 [SMILES: NC1=N[C@@]2(CCCc3ccc(-c4cncc(Cl)c4)cc32)C(F)(F)CO1] | $0.100^{a)}$ | 0.543 |
| 2 | 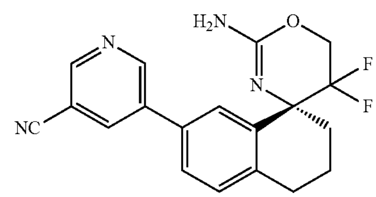 [SMILES: N#Cc1cncc(-c2ccc3c(c2)[C@@]2(CCC3)N=C(N)OCC2(F)F)c1] | $0.080^{a)}$ | 0.526 |
| 3 | 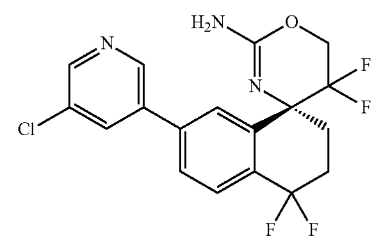 [SMILES: NC1=N[C@@]2(CCC(F)(F)c3ccc(-c4cncc(Cl)c4)cc32)C(F)(F)CO1] | $2.550^{a)}$ | — |
| 4 | 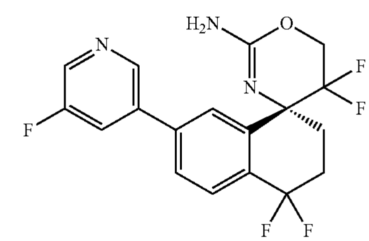 [SMILES: NC1=N[C@@]2(CCC(F)(F)c3ccc(-c4cncc(F)c4)cc32)C(F)(F)CO1] | $5.690^{a)}$ | — |
| 5 | 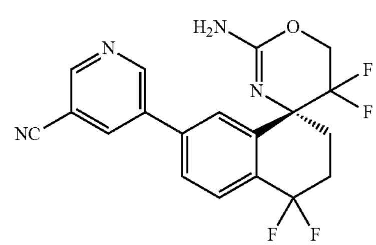 [SMILES: N#Cc1cncc(-c2ccc3c(c2)[C@@]2(CCC3(F)F)N=C(N)OCC2(F)F)c1] | $2.770^{a)}$ | — |

TABLE 1-continued

IC$_{50}$ values of selected examples, [a] and [b] indicate the respective cellular assay used

| Exam. | Structure | BACE1 cell act. Aβ40 IC$_{50}$ [μM] | BACE2 cell act. IC$_{50}$ [μM] |
|---|---|---|---|
| 6 | 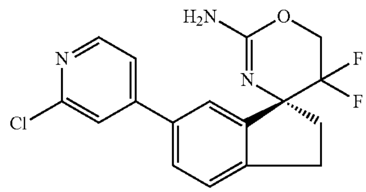 [SMILES: NC1=N[C@@]2(CCc3ccc(-c4ccnc(Cl)c4)cc32)C(F)(F)CO1] | 1.360[a] | — |
| 7 | 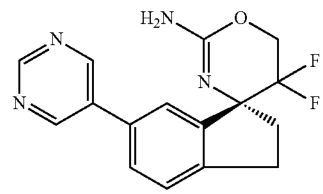 [SMILES: NC1=N[C@@]2(CCc3ccc(-c4cncnc4)cc32)C(F)(F)CO1] | 2.370[a] | — |
| 8 | 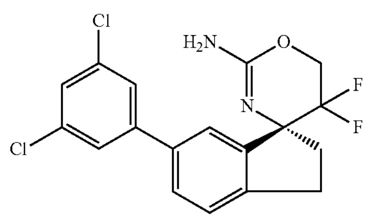 [SMILES: NC1=N[C@@]2(CCc3ccc(-c4cc(Cl)cc(Cl)c4)cc32)C(F)(F)CO1] | 2.450[a] | 2.730 |
| 9 | 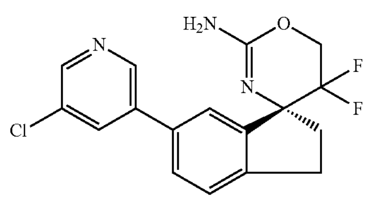 | 0.790[a] | 3.580 |
| 10 | 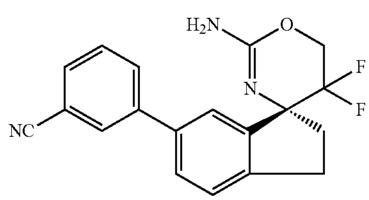 [SMILES: N#Cc1cccc(-c2ccc3c(c2)[C@@]2(CC3)N=C(N)OCC2(F)F)c1] | 0.960[a] | — |
| 11 | 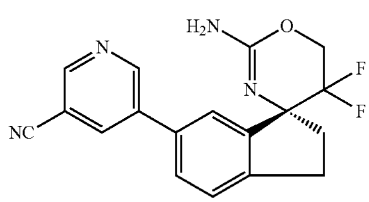 [SMILES: N#Cc1cncc(-c2ccc3c(c2)[C@@]2(CC3)N=C(N)OCC2(F)F)c1] | 3.380[b] | — |
| 12 | 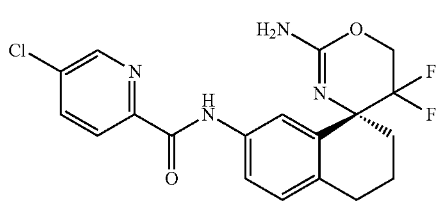 [SMILES: NC1=N[C@@]2(CCCc3ccc(NC(=O)c4ccc(Cl)cn4)cc32)C(F)(F)CO1] | 0.022[a] | — |

TABLE 1-continued

IC$_{50}$ values of selected examples, $^{a)}$ and $^{b)}$ indicate the respective cellular assay used

| Exam. | Structure | BACE1 cell act. Aβ40 IC$_{50}$ [μM] | BACE2 cell act. IC$_{50}$ [μM] |
|---|---|---|---|
| 13 | 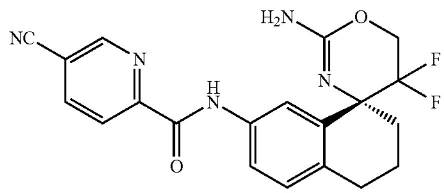 [SMILES: N#Cc1ccc(C(=O)Nc2ccc3c(c2)[C@@]2(CCC3)N=C(N)OCC2(F)F)nc1] | 0.005$^{a)}$ | 0.116 |
| 14 | 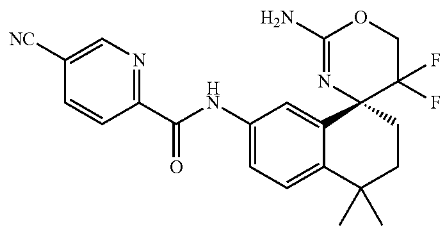 [SMILES: CC1(C)CC[C@@]2(N=C(N)OCC2(F)F)c2cc(NC(=O)c3ccc(C#N)cn3)ccc21] | 1.110$^{a)}$ | 13.034 |
| 15 | 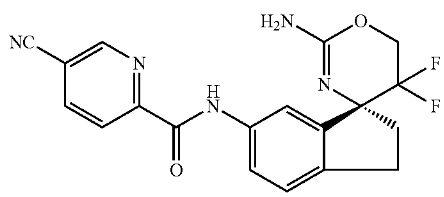 [SMILES: N#Cc1ccc(C(=O)Nc2ccc3c(c2)[C@@]2(CC3)N=C(N)OCC2(F)F)nc1] | 0.510$^{a)}$ | — |
| 16 | 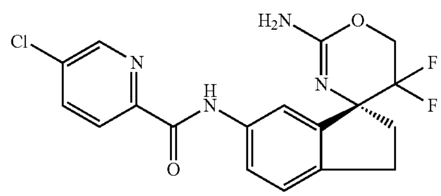 [SMILES: NC1=N[C@@]2(CCc3ccc(NC(=O)c4ccc(Cl)cn4)cc32)C(F)(F)CO1] | 2.490$^{a)}$ | — |
| 18 | 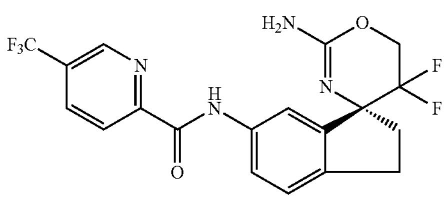 | 0.660$^{a)}$ | — |
| 19 | 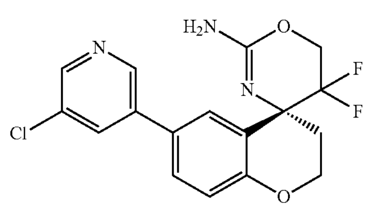 [SMILES: NC1=N[C@@]2(CCOc3ccc(-c4cncc(Cl)c4)cc32)C(F)(F)CO1] | 0.380$^{a)}$ | 0.124 |
| 20 | 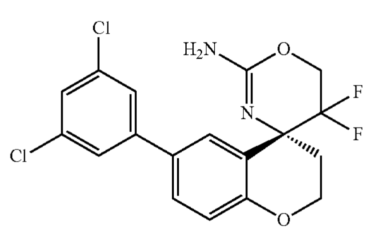 [SMILES: NC1=N[C@@]2(CCOc3ccc(-c4cc(Cl)cc(Cl)c4)cc32)C(F)(F)CO1] | 2.020$^{a)}$ | 3.995 |

TABLE 1-continued

IC$_{50}$ values of selected examples, $^{a)}$ and $^{b)}$ indicate the respective cellular assay used

| Exam. | Structure | BACE1 cell act. Aβ40 IC$_{50}$ [μM] | BACE2 cell act. IC$_{50}$ [μM] |
|---|---|---|---|
| 21 | 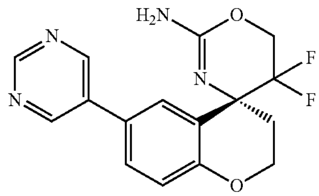 [SMILES: NC1=N[C@@]2(CCOc3ccc(-c4cncnc4)cc32)C(F)(F)CO1] | 5.140$^{a)}$ | — |
| 22 | 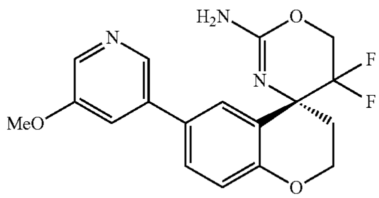 [SMILES: COc1cncc(-c2ccc3c(c2)[C@@]2(CCO3)N=C(N)OCC2(F)F)c1] | 2.780$^{a)}$ | 0.926 |
| 23 | 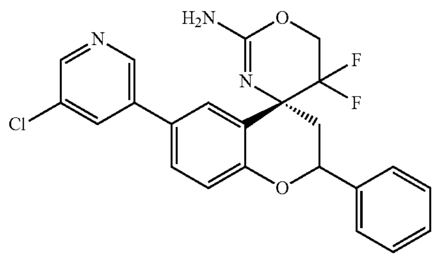 | 0.420$^{a)}$ | — |
| 24 | 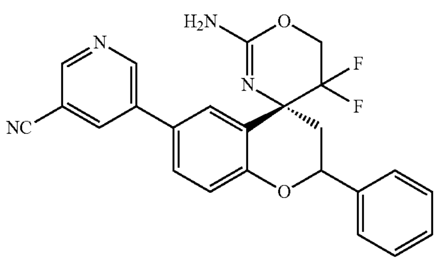 | 0.098$^{a)}$ | — |
| 25 | 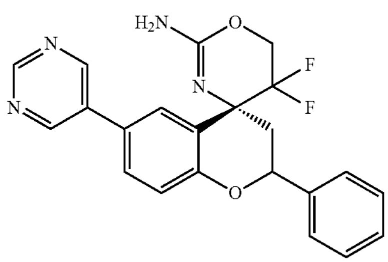 | 1.580$^{a)}$ | — |
| 26 | 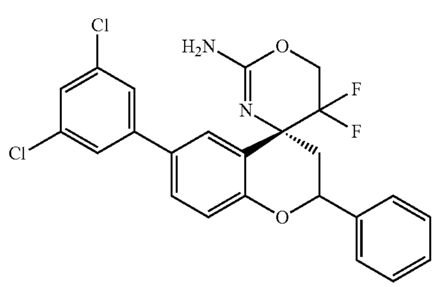 | 2.868$^{a)}$ | — |

TABLE 1-continued

IC$_{50}$ values of selected examples, $^{a)}$ and $^{b)}$ indicate the respective cellular assay used

| Exam. | Structure | BACE1 cell act. Aβ40 IC$_{50}$ [μM] | BACE2 cell act. IC$_{50}$ [μM] |
|---|---|---|---|
| 27 | 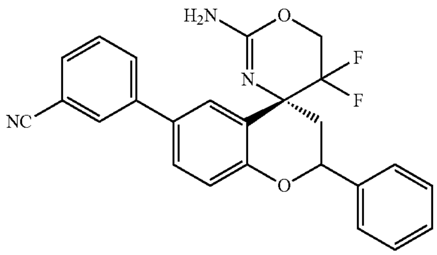 | 0.260$^{a)}$ | — |
| 28 | 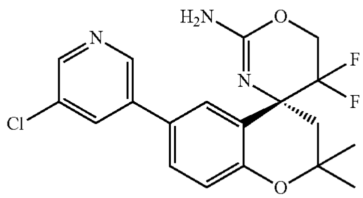 [SMILES: CC1(C)C[C@@]2(N=C(N)OCC2(F)F)c2cc(-c3cncc(Cl)c3)ccc2O1] | 2.530$^{a)}$ | — |
| 29 | 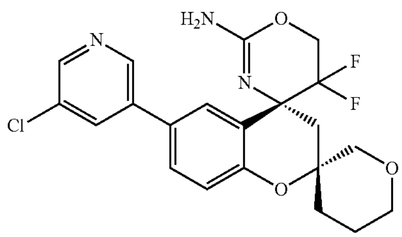 [SMILES: NC1=N[C@@]2(C[C@@]3(CCCOC3)Oc3ccc(-c4cncc(Cl)c4)cc32)C(F)(F)CO1] | 4.430$^{b)}$ | — |
| 30 | 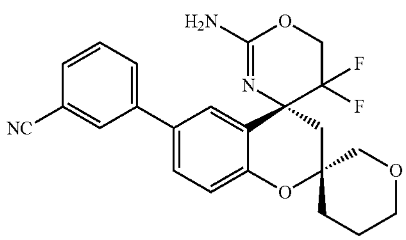 [SMILES: N#Cc1cccc(-c2ccc3c(c2)[C@@]2(C[C@@]4(CCCOC4)O3)N=C(N)OCC2(F)F)c1] | 6.580$^{b)}$ | — |
| 31 | 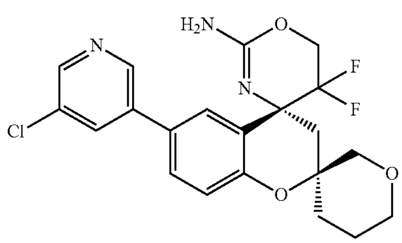 [SMILES: NC1=N[C@@]2(C[C@]3(CCCOC3)Oc3ccc(-c4cncc(Cl)c4)cc32)C(F)(F)CO1] | 9.000$^{b)}$ | — |
| 32 | 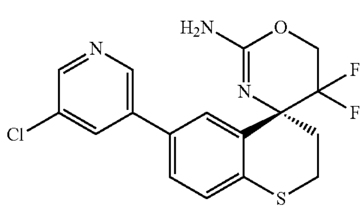 | 0.676$^{a)}$ | 1.947 |

TABLE 1-continued

IC$_{50}$ values of selected examples, $^{a)}$ and $^{b)}$ indicate the respective cellular assay used

| Exam. | Structure | BACE1 cell act. Aβ40 IC$_{50}$ [μM] | BACE2 cell act. IC$_{50}$ [μM] |
|---|---|---|---|
| 33 | 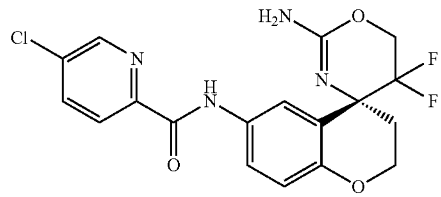 [SMILES: NC1=N[C@@]2(CCOc3ccc(NC(=O)c4ccc(Cl)cn4)cc32)C(F)(F)CO1] | 0.360$^{a)}$ | 0.986 |
| 34 | 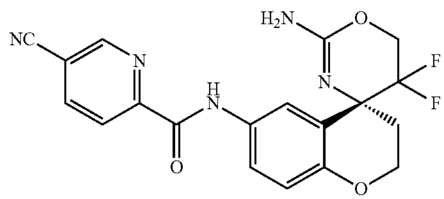 [SMILES: N#Cc1ccc(C(=O)Nc2ccc3c(c2)[C@@]2(CCO3)N=C(N)OCC2(F)F)nc1] | 0.080$^{a)}$ | 1.924 |
| 35 | 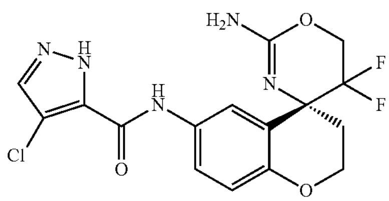 [SMILES: NC1=N[C@@]2(CCOc3ccc(NC(=O)c4[nH]ncc4Cl)cc32)C(F)(F)CO1] | 1.250$^{a)}$ | — |
| 36 | 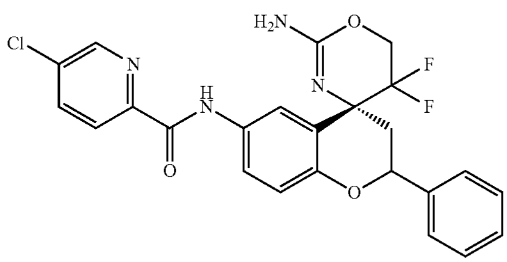 | 0.195$^{a)}$ | — |
| 37 | 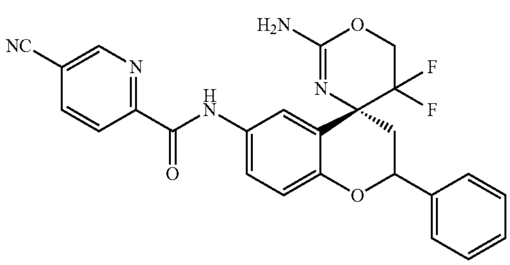 | 0.070$^{a)}$ | — |
| 38 | 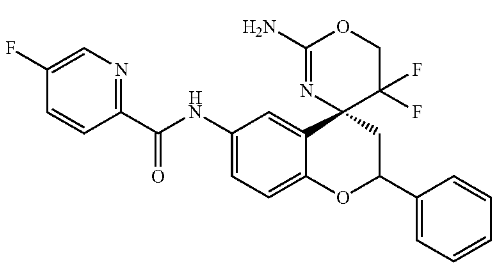 | 0.510$^{a)}$ | — |

TABLE 1-continued

IC$_{50}$ values of selected examples, $^{a)}$ and $^{b)}$ indicate the respective cellular assay used

| Exam. | Structure | BACE1 cell act. Aβ40 IC$_{50}$ [μM] | BACE2 cell act. IC$_{50}$ [μM] |
|---|---|---|---|
| 39 | 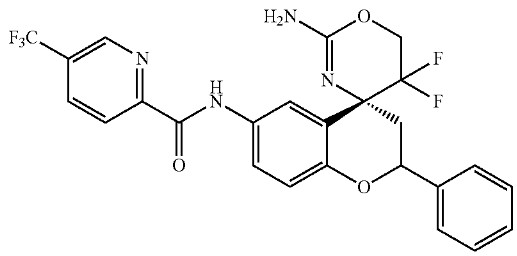 | 0.280$^{a)}$ | — |
| 40 | 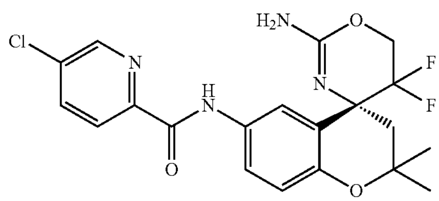 [SMILES: CC1(C)C[C@@]2(N=C(N)OCC2(F)F)c2cc(NC(=O)c3ccc(Cl)cn3)ccc2O1] | 2.260$^{a)}$ | — |
| 41 | 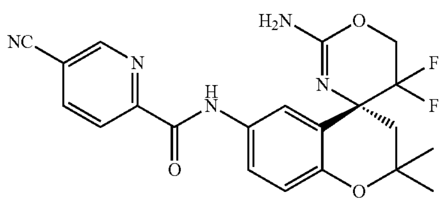 [SMILES: CC1(C)C[C@@]2(N=C(N)OCC2(F)F)c2cc(NC(=O)c3ccc(C#N)cn3)ccc2O1] | 0.230$^{a)}$ | — |
| 42 | 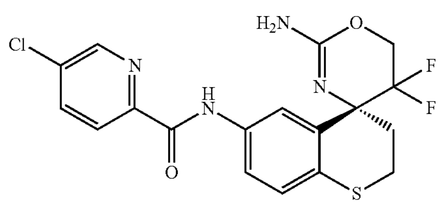 | 0.035$^{a)}$ | 0.438 |
| 43 | 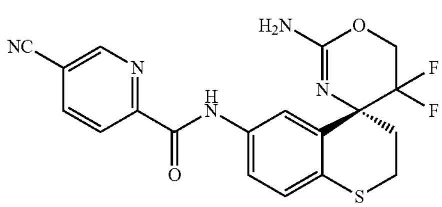 | 0.010$^{a)}$ | 0.148 |
| 44 | 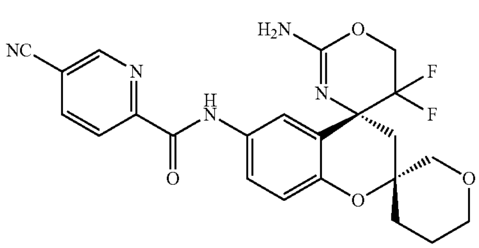 [SMILES: N#Cc1ccc(C(=O)Nc2ccc3c(c2)[C@@]2(C[C@@]4(CCCOC4)O3)N=C(N)OCC2(F)F)nc1] | 5.172$^{b)}$ | — |

TABLE 1-continued

IC$_{50}$ values of selected examples, $^{a)}$ and $^{b)}$ indicate the respective cellular assay used

| Exam. | Structure | BACE1 cell act. Aβ40 IC$_{50}$ [μM] | BACE2 cell act. IC$_{50}$ [μM] |
|---|---|---|---|
| 45 | 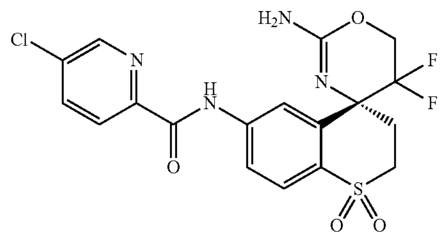 [SMILES: NC1=N[C@@]2(CCS(=O)(=O)c3ccc(NC(=O)c4ccc(Cl)cn4)cc32)C(F)(F)CO1] | 6.960$^{a)}$ | — |
| 46 | 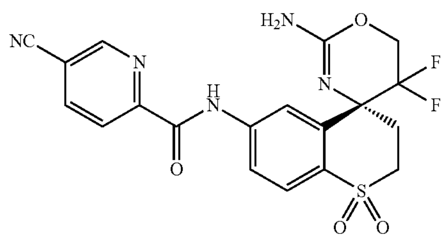 [SMILES: N#Cc1ccc(C(=O)Nc2ccc3c(c2)[C@@]2(CCS3(=O)=O)N=C(N)OCC2(F)F)nc1] | 3.400$^{a)}$ | — |
| 47 | 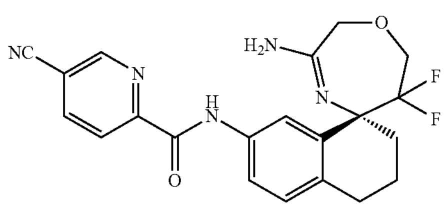 [SMILES: N#Cc1ccc(C(=O)Nc2ccc3c(c2)[C@@]2(CCC3)N=C(N)COCC2(F)F)nc1] | 0.240$^{a)}$ | — |
| 48 | 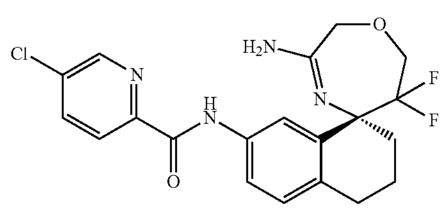 [SMILES: NC1=N[C@@]2(CCCc3ccc(NC(=O)c4ccc(Cl)cn4)cc32)C(F)(F)COC1] | 0.450$^{a)}$ | — |
| 49 | 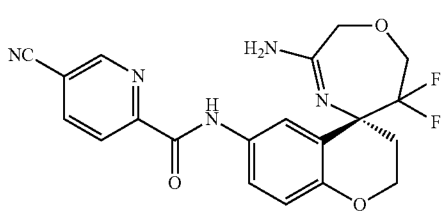 [SMILES: N#Cc1ccc(C(=O)Nc2ccc3c(c2)[C@@]2(CCO3)N=C(N)COCC2(F)F)nc1] | 0.830$^{a)}$ | — |
| 50 | 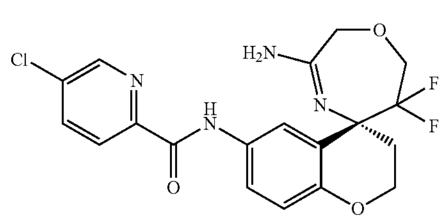 [SMILES: NC1=N[C@@]2(CCOc3ccc(NC(=O)c4ccc(Cl)cn4)cc32)C(F)(F)COC1] | 2.130$^{a)}$ | — |

TABLE 1-continued

IC$_{50}$ values of selected examples, [a] and [b] indicate the respective cellular assay used

| Exam. | Structure | BACE1 cell act. Aβ40 IC$_{50}$ [μM] | BACE2 cell act. IC$_{50}$ [μM] |
|---|---|---|---|
| 51 | 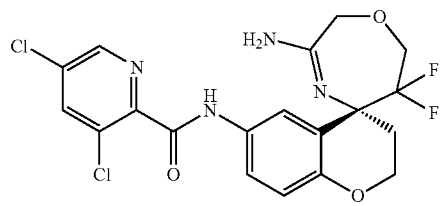 [SMILES: NC1=N[C@@]2(CCOc3ccc(NC(=O)c4ncc(Cl)cc4Cl)cc32)C(F)(F)COC1] | 1.691[a] | 5.866 |
| 52 | 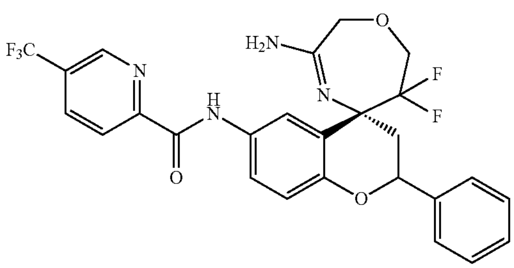 | 3.380[a] | — |
| 53 | 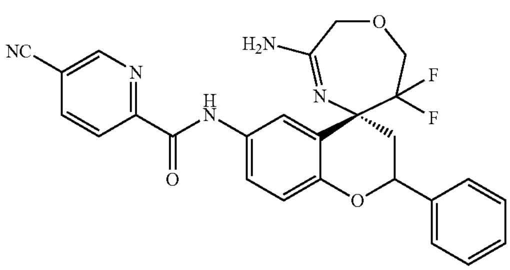 | 0.470[a] | — |
| 54 | 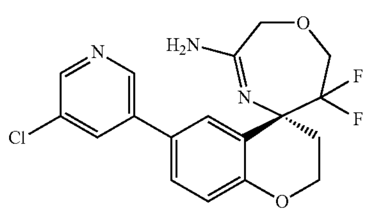 [SMILES: NC1=N[C@@]2(CCOc3ccc(-c4cncc(Cl)c4)cc32)C(F)(F)COC1] | 1.160[a] | — |
| 55 | 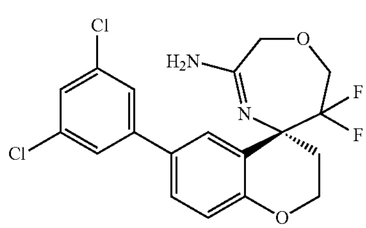 [SMILES: NC1=N[C@@]2(CCOc3ccc(-c4cc(Cl)cc(Cl)c4)cc32)C(F)(F)COC1] | 3.830[a] | 10.525 |
| 56 | 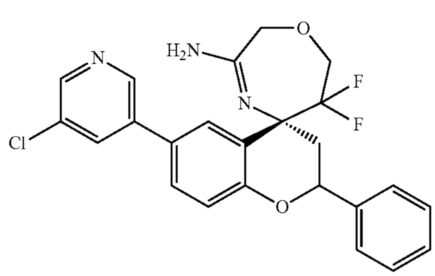 | 2.100[a] | — |

TABLE 1-continued

IC$_{50}$ values of selected examples, $^{a)}$ and $^{b)}$ indicate the respective cellular assay used

| Exam. | Structure | BACE1 cell act. Aβ40 IC$_{50}$ [μM] | BACE2 cell act. IC$_{50}$ [μM] |
|---|---|---|---|
| 57 | 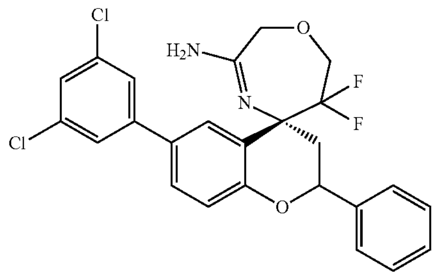 | 6.280$^{a)}$ | — |
| 58 | 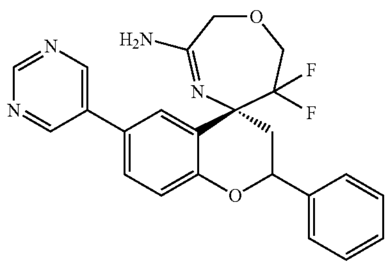 | 1.290$^{a)}$ | — |
| 59 | 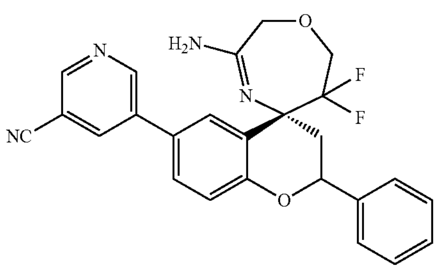 | 0.340$^{a)}$ | — |
| 60 | 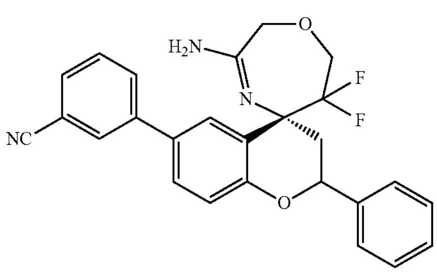 | 1.040$^{a)}$ | — |

Pharmaceutical Compositions

The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |

TABLE 3-continued possible capsule ingredient composition

| ingredient | mg/capsule | | | |
|---|---|---|---|---|
| | 5 | 25 | 100 | 500 |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof. MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Synthesis of the Intermediate Sulfinyl Imines A2

General Procedure

To a solution of the (R)-(+)-tert-butylsulfinamide (66 mmol) in tetrahydrofuran (350 ml) was added subsequently the ketone A1 (72.6 mmol) and titanium(IV)ethoxide (132 mmol) and the solution was stirred at reflux temperature for 5 h. The mixture was cooled to 22° C., treated with brine (400 ml), the suspension was stirred for 10 min and filtered over Dicalite®. The layers were separated, the aqueous layer was extracted with ethyl acetate, the combined organic layers were washed with water, dried and concentrated in vacuo. The residue was purified by chromatography on silica using cylohexane/ethyl acetate as the eluent to give the pure sulfinyl imine A2.

Intermediate A2.1

(X=—$CR^{1a}, R^{1b}$; $R^{1a}, R^{1b}$=H; W=—$CR^{2a}, R^{2b}$; $R^{2a}, R^{2b}$=H; p=1)

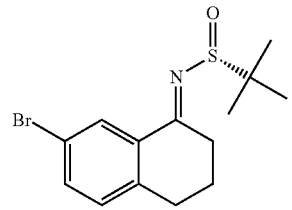 [SMILES: CC(C)(C)[S@@](=O)/N=C1\CCCc2ccc(Br)cc21]

Starting from 7-bromo-3,4-dihydro-2H-naphthalen-1-one {CAS[32281-97-3]} (intermediate A1.1), the product (R)-2-methyl-propane-2-sulfinic acid [7-bromo-3,4-dihydro-2H-naphthalen-(1E)-ylidene]-amide (64% yield) was obtained as a yellow solid. MS (ISP): m/z=328.1 $[M+H]^+$ and 329.9 $[M+2+H]^+$.

Intermediate A2.2

(X=—$CR^{1a}, R^{1b}$; $R^{1a}, R^{1b}$=H; W=—$CR^{2a}, R^{2b}$; $R^{2a}, R^{2b}$=H; p=1)

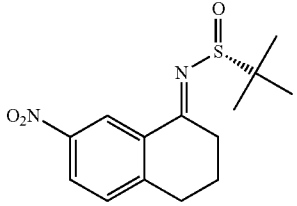 [SMILES: CC(C)(C)[S@@](=O)/N=C1\CCCc2ccc([N+](=O)[O-])cc21]

Starting from 7-nitro-3,4-dihydro-2H-naphthalen-1-one {CAS[40353-34-2]} (intermediate A1.2), the product (R)-2-methyl-propane-2-sulfinic acid [7-nitro-3,4-dihydro-2H-naphthalen-(1E)-ylidene]-amide (62% yield) was obtained as a yellow solid.

Intermediate A2.3
(X=—CR$^{1a}$, R$^{1b}$; R$^{1a}$, R$^{1b}$=CH$_3$; W=—CR$^{2a}$, R$^{2b}$; R$^{2a}$, R$^{2b}$=H; p=1)

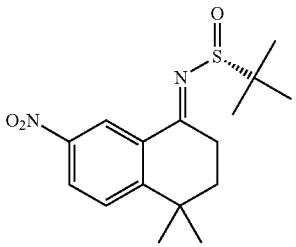 [SMILES: CC1(C)CC/C(=N\[S@](=O)C(C)(C)C)c2cc([N+](=O)[O-])ccc21]

Starting from 4,4-dimethyl-7-nitro-3,4-dihydro-2H-naphthalen-1-one (WO03095430) (intermediate A1.3), the product (R)-2-methyl-propane-2-sulfinic acid [4,4-dimethyl-7-nitro-3,4-dihydro-2H-naphthalen-(1E)-ylidene]-amide (66% yield) was obtained as a yellow solid. MS (ISP): m/z=323.5 [M+H]$^+$.

Intermediate A2.4
(X=—CR$^{1a}$, R$^{1b}$; R$^{1a}$, R$^{1b}$=F; W=—CR$^{2a}$, R$^{2b}$; R$^{2a}$, R$^{2b}$=H; p=1)

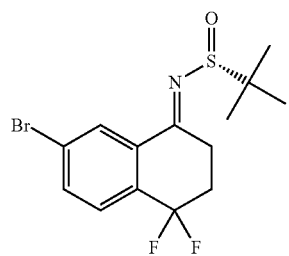 [SMILES: CC(C)(C)[S@@](=O)/N=C1\CCC(F)(F)c2ccc(Br)cc21]

Starting from 7-bromo-4,4-difluoro-3,4-dihydro-2H-naphthalen-1-one (intermediate A1.4), the product (R)-2-methyl-propane-2-sulfinic acid [7-bromo-4,4-difluoro-3,4-dihydro-2H-naphthalen-(1E)-ylidene]-amide (97% yield) was obtained as a light brown solid. MS (ISP): m/z=365.9 [M+H]$^+$.

The 7-bromo-4,4-difluoro-3,4-dihydro-2H-naphthalen-1-one (intermediate A1.4) was obtained as follows:

a) 6'-Bromo-3',4'-dihydro-2'H-spiro[[1,3]dithiolane-2,1'-naphthalene]

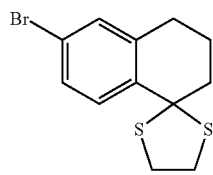 [SMILES: Brc1ccc2c(c1)CCCC21SCCS1]

A solution of 6-bromo-3,4-dihydro-2H-naphthalen-1-one (CAS[66361-67-9]) (0.9 g, 4.00 mmol) in dichloromethane (8 ml) was cooled to 0° C. and treated with 1,2-ethandithiol (769 mg, 686 µl, 8.00 mmol) and boron trifluoro etherate (284 mg, 247 µl, 2.00 mmol). The reaction mixture was left to warm to room temperature and stirred for 15 hours. For the workup, the reaction mixture was poured into a solution of sodium hydroxide (1N) followed by extraction with dichloromethane (40 ml). The organic layer was dried over sodium sulphate and evaporated. The crude product was purified by chromatography on silica gel using a gradient of heptane/ethyl acetate=100:0 to 70:30 as the eluent. The 6'-bromo-3',4'-dihydro-2'H-spiro[[1,3]dithiolane-2,1'-naphthalene] (1.06 g, 88% yield) was obtained as a light red oil.

b) 6-Bromo-1,1-difluoro-1,2,3,4-tetrahydro-naphthalene

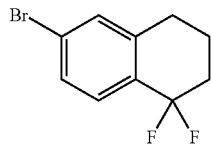

A suspension of N-iodosuccinimide (1.78 g, 7.9 mmol) in dichloromethane (15 ml) was cooled to –70° C. Hydrogen fluoride-pyridine (1.57 g, 1.42 ml, 15.8 mmol) was added dropwise. A cold solution (–70° C.) of 6'-bromo-3',4'-dihydro-2'H-spiro[[1,3]dithiolane-2,1'-naphthalene] (1.19 g, 3.95 mmol) in dichloromethane (10 ml) was added dropwise and the white suspension changed to a brown. The mixture was stirred at –70° C. for 15 minutes. For the workup, the dark red solution was poured into a mixture of hexane (50 ml) and dichloromethane (10 ml). The deeply colored solution was first passed through a layer of silica gel, then through a layer of a silica-NH$_2$ phase and Dicalite®. The resulting colorless solution was evaporated and the crude product purified by chromatography on silica gel using a gradient of heptane/ethyl acetate=100:0 to 90:10 as the eluent. The 6-bromo-1,1-difluoro-1,2,3,4-tetrahydro-naphthalene (668 mg, 68% yield) was obtained as a pale yellow oil.

c) 7-Bromo-4,4-difluoro-3,4-dihydro-2H-naphthalen-1-one

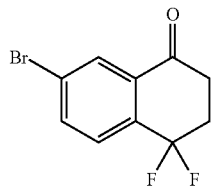 [SMILES: O=C1CCC(F)(F)c2ccc(Br)cc21]

A solution of 6-bromo-1,1-difluoro-1,2,3,4-tetrahydro-naphthalene (691 mg, 2.8 mmol) in tert-butanol (7 ml). A solution of potassium dihydrogenphosphate (769 mg, 5.59 mmol) in water (2 ml) and a solution of sodium phosphate heptahydrate (1.51 g, 5.59 mmol) in water (2 ml) were added. Thereafter, potassium permanganate (670 mg, 4.2 mmol) was added and the reaction mixture stirred at room temperature for 15 hours. For the workup, the mixture was diluted with ethyl acetate (200 ml), the organic layer separated, washed with water (10 ml) and brine (10 ml), finally dried over sodium sulphate and evaporated at reduced pressure. The crude product was purified by chromatography on silica gel using a gradient of heptane/ethyl acetate=100:0 to 80:20 as the eluent. The 7-bromo-4,4-difluoro-3,4-dihydro-2H-naphthalen-1-one (515 mg, 71% yield) was obtained as a colorless oil.

Intermediate A2.5
(X=—CR$^{1a}$, R$^{1b}$; R$^{1a}$, R$^{1b}$=H; p=0)

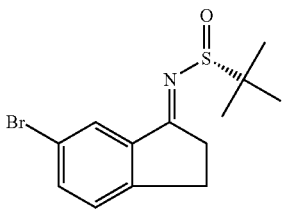 [SMILES: CC(C)(C)[S@@](=O)/N=C1\CCc2ccc(Br)cc21]

Starting from 6-bromo-indan-1-one {CAS[14548-39-1]} (intermediate A1.5), the product (R)-2-methyl-propane-2-sulfinic acid [6-bromo-indan-(1E)-ylidene]-amide (34% yield) was obtained as a yellow solid. MS (ISP): m/z=314.2 [M+H]$^+$.

Intermediate A2.6
(X=—CR$^{1a}$, R$^{1b}$; R$^{1a}$, R$^{1b}$=H; p=0)

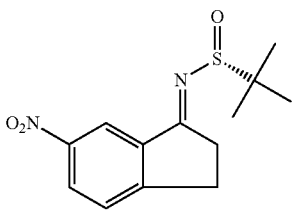 [SMILES: CC(C)(C)[S@@](=O)/N=C1\CCc2ccc([N+](=O)[O-])cc21]

Starting from 6-nitro-indan-1-one {CAS[24623-24-3]} (intermediate A1.6), the product (R)-2-methyl-propane-2-sulfinic acid [6-nitro-indan-(1E)-ylidene]-amide (51% yield) was obtained as a blackish semi-solid. MS (ISP): m/z=281.0 [M+H]$^+$.

Synthesis of the Intermediate Sulfinamide Esters A3
General Procedure (Via Reformatsky Reaction)

In a dry apparatus a suspension of freshly activated zinc powder (1.63 g, 24.9 mmol) in dry tetrahydrofuran (70 ml) was heated under an inert atmosphere to reflux. A solution of the sulfinyl imine A2 (24.9 mmol) and the bromo-acetate (24.9 mmol) in dry tetrahydrofuran (15 ml) was added dropwise over a period of 15 min and the suspension was heated to reflux for 5 h (5 hours). The cooled mixture was partitioned between a saturated aqueous solution of ammonium chloride and ethyl acetate, the organic layer was dried and evaporated. The crude material was purified by flash chromatography using heptane/ethyl acetate as the eluent to give the sulfinamide ester A3.

Intermediate A3.1

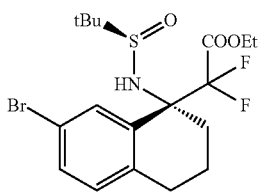 [SMILES: CCOC(=O)C(F)(F)[C@@]1(N[S@](=O)C(C)(C)C)CCCc2ccc(Br)cc21]

Starting from (R)-2-methyl-propane-2-sulfinic acid [7-bromo-3,4-dihydro-2H-naphthalen-(1E)-ylidene]-amide (intermediate A2.1), the product [(R)-7-bromo-1-((R)-2-methyl-propane-2-sulfinylamino)-1,2,3,4-tetrahydro-naphthalen-1-yl]-difluoro-acetic acid ethyl ester (90% yield) was obtained as a light brown oil. MS (ISP): m/z=452.1 [M+H]$^+$ and 454.1 [M+2+H]$^+$.

Intermediate A3.2

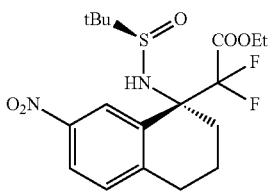 [SMILES: CCOC(=O)C(F)(F)[C@@]1(N[S@](=O)C(C)(C)C)CCCc2ccc([N+](=O)[O-])cc21]

Starting from (R)-2-methyl-propane-2-sulfinic acid [7-nitro-3,4-dihydro-2H-naphthalen-(1E)-ylidene]-amide (intermediate A2.2), the product difluoro-[(R)-1-((R)-2-methyl-propane-2-sulfinylamino)-7-nitro-1,2,3,4-tetrahydro-naphthalen-1-yl]-acetic acid ethyl ester (83% yield) was obtained as a yellow oil. MS (ISP): m/z=419.2 [M+H]$^+$.

Intermediate A3.3

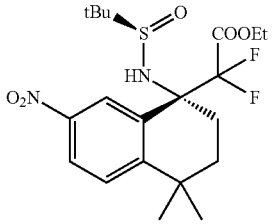 [SMILES: CCOC(=O)C(F)(F)[C@@]1(N[S@](=O)C(C)(C)C)CCC(C)(C)c2ccc([N+](=O)[O-])cc21]

Starting from (R)-2-methyl-propane-2-sulfinic acid [4,4-dimethyl-7-nitro-3,4-dihydro-2H-naphthalen-(1E)-ylidene]-amide (intermediate A2.3), the product [(R)-4,4-dimethyl-1-((R)-2-methyl-propane-2-sulfinylamino)-7-nitro-1,2,3,4-tetrahydro-naphthalen-1-yl]-difluoro-acetic acid ethyl ester (73% yield) was obtained as a yellow oil. MS (ISP): m/z=447.5 [M+H]$^+$.

Intermediate A3.4

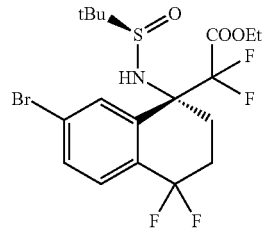 [SMILES: CCOC(=O)C(F)(F)[C@@]1(N[S@](=O)C(C)(C)C)CCC(F)(F)c2ccc(Br)cc21]

Starting from (R)-2-methyl-propane-2-sulfinic acid [7-bromo-4,4-difluoro-3,4-dihydro-2H-naphthalen-(1E)-ylidene]-amide (intermediate A2.4) and ethyl 2-bromo-2,2-difluoroacetate, the product [(R)-7-bromo-4,4-difluoro-1-((R)-2-methyl-propane-2-sulfinylamino)-1,2,3,4-tetrahydro-naphthalen-1-yl]-difluoro-acetic acid ethyl ester (58% yield) was obtained as a brown solid. MS (ISP): m/z=488.1 [M+H]$^+$ and 490.0 [M+H]$^+$.

Intermediate A3.5

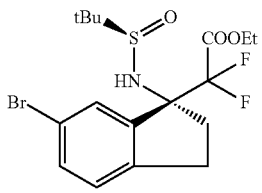 [SMILES: CCOC(=O)C(F)(F)[C@@]1(N[S@](=O)C(C)(C)C)CCc2ccc(Br)cc21]

Starting from (R)-2-methyl-propane-2-sulfinic acid [6-bromo-indan-(1E)-ylidene]-amide (intermediate A2.5), the product [(R)-6-bromo-1-((R)-2-methyl-propane-2-sulfinylamino)-indan-1-yl]-difluoro-acetic acid ethyl ester (43% yield) was obtained as a deep brown solid. MS (ISP): m/z=438.0 [M+H]$^+$.

Intermediate A3.6

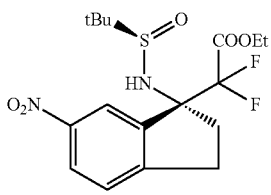 [SMILES: CCOC(=O)C(F)(F)[C@@]1(N[S@](=O)C(C)(C)C)CCc2ccc([N+](=O)[O-])cc21]

Starting from (R)-2-methyl-propane-2-sulfinic acid [6-nitro-indan-(1E)-ylidene]-amide (intermediate A2.6), the product difluoro-[(R)-1-((R)-2-methyl-propane-2-sulfinylamino)-6-nitro-indan-1-yl]-acetic acid ethyl ester (60% yield) was obtained as a blackish semi-solid. MS (ISP): m/z=405.0 [M+H]$^+$.

Synthesis of the Intermediate Sulfinamide Alcohols A4

General Procedure

A solution of the sulfinamide ester A3 (12.7 mmol) in dry tetrahydrofuran (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate as the eluent to give the pure intermediate sulfinamide alcohol A4.

Intermediate A4.1

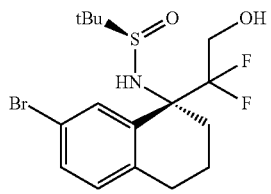 [SMILES: CC(C)(C)[S@@](=O)N[C@]1(C(F)(F)CO)CCCc2ccc(Br)cc21]

Starting from [(R)-7-bromo-1-((R)-2-methyl-propane-2-sulfinylamino)-1,2,3,4-tetrahydro-naphthalen-1-yl]-difluoro-acetic acid ethyl ester (intermediate A3.1), the product (R)-2-methyl-propane-2-sulfinic acid [(R)-7-bromo-1-(1,1-difluoro-2-hydroxy-ethyl)-1,2,3,4-tetrahydro-naphthalen-1-yl]-amide (45% yield) was obtained as a white solid. MS (ISP): m/z=410.1 [M+H]$^+$ and 412.1 [M+2+H]$^+$.

Intermediate A4.2

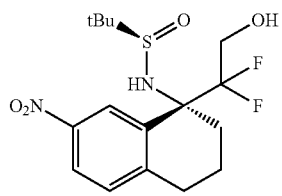 [SMILES: CC(C)(C)[S@@](=O)N[C@]1(C(F)(F)CO)CCCc2ccc([N+](=O)[O-])cc21]

Starting from difluoro-[(R)-1-((R)-2-methyl-propane-2-sulfinylamino)-7-nitro-1,2,3,4-tetrahydro-naphthalen-1-yl]-acetic acid ethyl ester (intermediate A3.2), the product (R)-2-methyl-propane-2-sulfinic acid [(R)-1-(1,1-difluoro-2-hydroxy-ethyl)-7-nitro-1,2,3,4-tetrahydro-naphthalen-1-yl]-amide (92% yield) was obtained as a brown solid. MS (ISP): m/z=377.4 [M+H]$^+$.

Intermediate A4.3

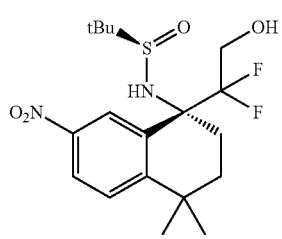 [SMILES: CC1(C)CC[C@](N[S@](=O)C(C)(C)C)(C(F)(F)CO)c2cc([N+](=O)[O-])ccc21]

Starting from [(R)-4,4-dimethyl-1-((R)-2-methyl-propane-2-sulfinylamino)-7-nitro-1,2,3,4-tetrahydro-naphthalen-1-yl]-difluoro-acetic acid ethyl ester (intermediate A3.3), the product (R)-2-methyl-propane-2-sulfinic acid [(R)-1-(1,1-difluoro-2-hydroxy-ethyl)-4,4-dimethyl-7-nitro-1,2,3,4-tetrahydro-naphthalen-1-yl]-amide (50% yield) was obtained as a light brown solid. MS (ISP): m/z=405.5 [M+H]$^+$.

Intermediate A4.4

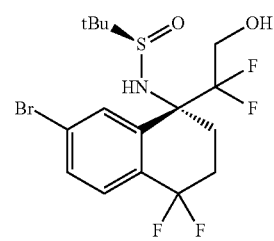 [SMILES: CC(C)(C)[S@@](=O)N[C@]1(C(F)(F)CO)CCC(F)(F)c2ccc(Br)cc21]

Starting from [(R)-7-bromo-4,4-difluoro-1-((R)-2-methyl-propane-2-sulfinylamino)-1,2,3,4-tetrahydro-naphthalen-1-yl]-difluoro-acetic acid ethyl ester (intermediate A3.4), the product (R)-2-methyl-propane-2-sulfinic acid [(R)-7-bromo-1-(1,1-difluoro-2-hydroxy-ethyl)-4,4-difluoro-1,2,3,4-tetrahydro-naphthalen-1-yl]-amide (100% yield) was obtained as a grey foam. MS (ISP): m/z=446.0 [M+H]$^+$ and 447.9 [M+H]$^+$.

Intermediate A4.5

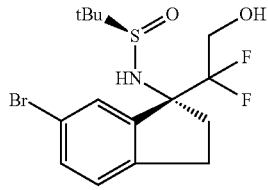 [SMILES: CC(C)(C)[S@@](=O)N[C@]1(C(F)(F)CO)CCc2ccc(Br)cc21]

Starting from [(R)-6-bromo-1-((R)-2-methyl-propane-2-sulfinylamino)-indan-1-yl]-difluoro-acetic acid ethyl ester (intermediate A3.5), the product (R)-2-methyl-propane-2-sulfinic acid [(R)-6-bromo-1-(1,1-difluoro-2-hydroxy-ethyl)-indan-1-yl]-amide (77% yield) was obtained as a deep brown solid. MS (ISP): m/z=395.8 [M+H]$^+$.

Intermediate A4.6

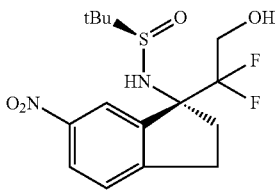 [SMILES: CC(C)(C)[S@@](=O)N[C@]1(C(F)(F)CO)CCc2ccc([N+](=O)[O-])cc21]

Starting from difluoro-[(R)-1-((R)-2-methyl-propane-2-sulfinylamino)-6-nitro-indan-1-yl]-acetic acid ethyl ester (intermediate A3.6), the product (R)-2-methyl-propane-2-sulfinic acid [(R)-1-(1,1-difluoro-2-hydroxy-ethyl)-6-nitro-indan-1-yl]amide (84% yield) was obtained as a deep brown solid. MS (ISP): m/z=363.2 [M+H]$^+$.

Synthesis of the Intermediate Amino Alcohols A5

General Procedure:

A solution of the sulfinamide alcohols A4 (10.3 mmol) in methanol or tetrahydrofuran (30 to 60 ml) was treated with a solution of hydrochloric acid in 1,4-dioxane (4 M, 10-13 ml) and stirring was continued at 23° C. for 2 to 18 h. The mixture was partitioned between ethyl acetate and an aqueous solution of sodium carbonate (2 M), the organic layer was dried over sodium sulphate, filtered and evaporated to give a residue which was purified by chromatography on silica using a mixture of n-heptane and ethyl acetate as the eluent to give the pure aminoalcohols A5.

Intermediate A5.1

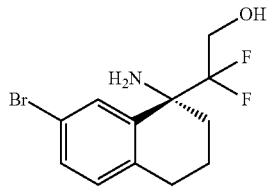

Starting from (R)-2-methyl-propane-2-sulfinic acid [(R)-7-bromo-1-(1,1-difluoro-2-hydroxy-ethyl)-1,2,3,4-tetrahydro-naphthalen-1-yl]-amide (intermediate A4.1), the product 2-((R)-1-amino-7-bromo-1,2,3,4-tetrahydro-naphthalen-1-yl)-2,2-difluoro-ethanol (25% yield) was obtained as a pale yellow gum. MS (ISP): m/z=306.0 [M+H]$^+$ and 308.1 [M+2+H]$^+$.

Intermediate A5.2

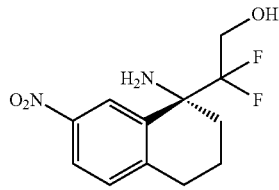 [SMILES: N[C@]1(C(F)(F)CO)CCCc2ccc([N+](=O)[O-])cc21]

Starting from (R)-2-methyl-propane-2-sulfinic acid [(R)-1-(1,1-difluoro-2-hydroxy-ethyl)-7-nitro-1,2,3,4-tetrahydro-naphthalen-1-yl]amide (intermediate A4.2), the product 2-((R)-1-amino-7-nitro-1,2,3,4-tetrahydro-naphthalen-1-yl)-2,2-difluoro-ethanol (74% yield) was obtained as a pale yellow solid. MS (ISN): m/z=271.3 [M−H]$^-$.

Intermediate A5.3

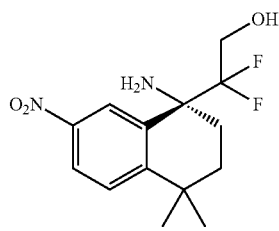 [SMILES: CC1(C)CC[C@](N)(C(F)(F)CO)c2cc([N+](=O)[O-])ccc21]

Starting from (R)-2-methyl-propane-2-sulfinic acid [(R)-1-(1,1-difluoro-2-hydroxy-ethyl)-4,4-dimethyl-7-nitro-1,2,3,4-tetrahydro-naphthalen-1-yl]-amide (intermediate A4.3), the product 2-((R)-1-amino-4,4-dimethyl-7-nitro-1,2,3,4-tetrahydro-naphthalen-1-yl)-2,2-difluoro-ethanol (49% yield) was obtained as an off-white foam. MS (ISP): m/z=301.4 [M+H]$^+$.

Intermediate A5.4

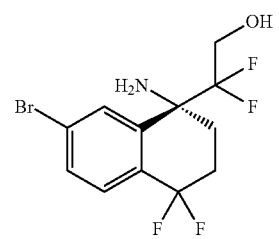 [SMILES: N[C@]1(C(F)(F)CO)CCC(F)(F)c2ccc(Br)cc21]

Starting from (R)-2-methyl-propane-2-sulfinic acid [(R)-7-bromo-1-(1,1-difluoro-2-hydroxy-ethyl)-4,4-difluoro-1,2,3,4-tetrahydro-naphthalen-1-yl]-amide (intermediate A4.4), the product 2-((R)-1-amino-7-bromo-4,4-difluoro-1,2,3,4-tetrahydro-naphthalen-1-yl)-2,2-difluoro-ethanol (44% yield) was obtained as a yellow oil. MS (ISP): m/z=342.0 [M+H]$^+$ and 344.0 [M+2+H]$^+$.

Intermediate A5.5

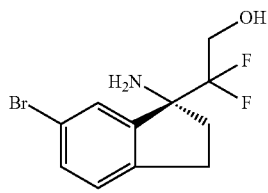

Starting from (R)-2-methyl-propane-2-sulfinic acid [(R)-6-bromo-1-(1,1-difluoro-2-hydroxy-ethyl)-indan-1-yl]-amide (intermediate A4.5), the product 2-((R)-1-amino-6-bromo-indan-1-yl)-2,2-difluoro-ethanol (81% yield) was obtained as a deep brown solid. MS (ISP): m/z=291.0 [M+H]$^+$.

Intermediate A5.6

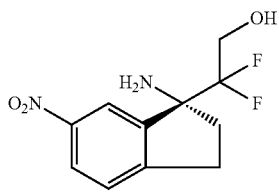 [SMILES: N[C@]1(C(F)(F)CO)CCc2ccc([N+](=O)[O-])cc21]

Starting from (R)-2-methyl-propane-2-sulfinic acid [(R)-1-(1,1-difluoro-2-hydroxy-ethyl)-6-nitro-indan-1-yl]-amide (intermediate A4.6), the product 2-((R)-1-amino-6-nitro-indan-1-yl)-2,2-difluoro-ethanol (70% yield) was obtained as a deep brown solid. MS (ISP): m/z=258.9 [M+H]$^+$.

Syntheses of the Intermediate Amino Oxazines A6

General Procedure

A dried tube was charged with a mixture of the amino alcohol A5 (18.8 mmol), cyanogen bromide (33.9 mmol) and ethanol (61 ml). The tube was sealed and heated at 90° C. for 16 hours. For the workup, the reaction mixture was cooled and evaporated at reduced pressure. The residue was partitioned between ethyl acetate (150 ml) and a saturated aqueous solution of sodium carbonate (50 ml). The aqueous layer was separated and re-extracted with ethyl acetate (2×50 ml). The organic layers were washed with brine (50 ml), then combined, dried over sodium sulphate and evaporated at reduced pressure. The product was used in the next step without further purification.

Intermediate A6.1

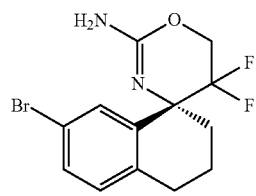

Starting from 2-((R)-1-amino-7-bromo-1,2,3,4-tetrahydro-naphthalen-1-yl)-2,2-difluoro-ethanol (intermediate A5.1), the product (R)-7-bromo-5',5'-difluoro-3,4,5',6'-tetrahydro-2H-spiro[naphthalene-1,4'-[1,3]oxazin]-2'-amine (50% yield) was obtained as a white solid. MS (ISP): m/z=331.0 [M+H]$^+$ and 333.0 [M+2+H]$^+$.

Intermediate A6.2

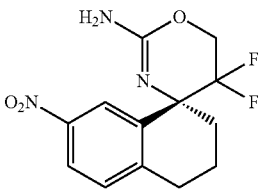 [SMILES: NC1=N[C@@]2(CCCc3ccc([N+](=O)[O-])cc32)C(F)(F)CO1]

Starting from 2-((R)-1-amino-7-nitro-1,2,3,4-tetrahydro-naphthalen-1-yl)-2,2-difluoro-ethanol (intermediate A5.2), the product (R)-5',5'-difluoro-7-nitro-3,4,5',6'-tetrahydro-2H-spiro[naphthalene-1,4'-[1,3]oxazin]-2'-amine (62% yield) was obtained as a white solid. MS (ISP): m/z=298.2 [M+H]$^+$.

Intermediate A6.3

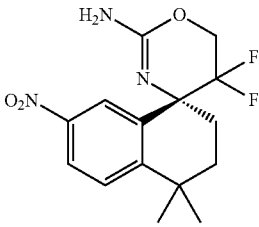 [SMILES: CC1(C)CC[C@@]2(N=C(N)OCC2(F)F)c2cc([N+](=O)[O-])ccc21]

Starting from 2-((R)-1-amino-4,4-dimethyl-7-nitro-1,2,3,4-tetrahydro-naphthalen-1-yl)-2,2-difluoro-ethanol (intermediate A5.3), the product (R)-5',5'-difluoro-4,4-dimethyl-7-nitro-3,4,5',6'-tetrahydro-2H-spiro[naphthalene-1,4'-[1,3]oxazin]-2'-amine (51% yield) was obtained as a pale yellow gum. MS (ISP): m/z=326.5 [M+H]$^+$.

Intermediate A6.4

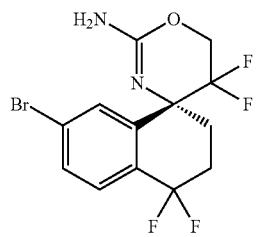 [SMILES: NC1=N[C@@]2(CCC(F)(F)c3ccc(Br)cc32)C(F)(F)CO1]

Starting from 2-((R)-1-amino-7-bromo-4,4-difluoro-1,2,3,4-tetrahydro-naphthalen-1-yl)-2,2-difluoro-ethanol (intermediate A5.4), the product (R)-7-bromo-4,4,5',5'-tetrafluoro-3,4,5',6'-tetrahydro-2H-spiro[naphthalene-1,4'-[1,3]oxazin]-2'-amine (65% yield) was obtained as a white solid. MS (ISP): m/z=366.9 [M+H]$^+$ and 369.0 [M+H]$^+$.

Intermediate A6.5

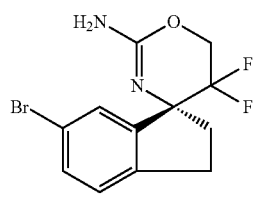 [SMILES: NC1=N[C@@]2(CCc3ccc(Br)cc32)C(F)(F)CO1]

Starting from 2-((R)-1-amino-6-bromo-indan-1-yl)-2,2-difluoro-ethanol (intermediate A5.5), the product (R)-6-bromo-5',5'-difluoro-2,3,5',6'-tetrahydrospiro[indene-1,4'-[1,3]oxazin]-2'-amine (64% yield) was obtained as an off-white solid. MS (ISP): m/z=346.8 [M+H]+.
Intermediate A6.6

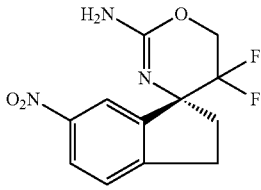 [SMILES: NC1=N[C@@]2(CCc3ccc([N+](=O)[O-])cc32)C(F)(F)CO1]

a) (R)-1-(1,1-Difluoro-2-hydroxy-ethyl)-6-nitro-indan-1-yl-cyanamide

A mixture of 2-((R)-1-amino-6-nitro-indan-1-yl)-2,2-difluoro-ethanol (intermediate A5.6), (1.6 g, 6.2 mmol) and sodium acetate (1.54 g, 18.6 mmol) in ethanol (30 ml) was warmed to 40° C. The mixture was then treated with cyanogen bromide (724 mg, 6.82 mmol) and allowed to stir at 40° C. for 16 hours. Removal of the solvent at reduced pressure followed by purification of the resultant crude material by column chromatography on silica gel using a 3:2-mixture of hexane and ethyl acetate as the eluent yielded the (R)-1-(1,1-difluoro-2-hydroxy-ethyl)-6-nitro-indan-1-yl-cyanamide (800 mg, 42% yield) as colorless sticky solid. MS (ISP): m/z=284.0 [M+H]+.

b) (R)-5',5'-Difluoro-6-nitro-2,3,5',6'-tetrahydrospiro[indene-1,4'-[1,3]oxazin]-2'-amine In a tube, a solution of (R)-1-(1,1-difluoro-2-hydroxy-ethyl)-6-nitro-indan-1-yl-cyanamide (1.0 g, 3.55 mmol) in methanol (10 ml) was treated with ammonium hydroxide (25% in water, 3 ml). The tube was sealed and heated at 60° C. for 16 hours. For the workup, the reaction mixture was evaporated at reduced pressure. The crude material was purified by column chromatography (NH-biotage) using a 95:5-mixture of dichloromethane and methanol as the eluent. The (R)-5',5'-difluoro-6-nitro-2,3,5',6'-tetrahydrospiro[indene-1,4'-[1,3]oxazin]-2'-amine (500 mg, 50% yield) was obtained as a white solid. MS (ISP): m/z=283.4 [M+H]+.

Syntheses of the Intermediate Anilines A7
General Procedure

A solution of the nitro oxazine A6 (3 mmol) in ethanol (31 ml) was hydrogenated at atmospheric pressure using palladium (10% on carbon) (159 mg, 150 µmol) as the catalyst. After 90 minutes the reaction was complete. The reaction mixture was filtrated over a layer of Dicalit, which was washed with ethanol (3×20 ml). The combined solutions of ethanol were evaporated at reduced pressure. The product was engaged in the step without further purification.
Intermediate A7.1

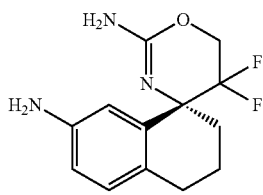

Starting from (R)-5',5'-difluoro-7-nitro-3,4,5',6'-tetrahydro-2H-spiro[naphthalene-1,4'-[1,3]oxazin]-2'-amine (intermediate A6.2), the product (R)-5',5'-difluoro-3,4,5',6'-tetrahydro-2H-spiro[naphthalene-1,4'-[1,3]oxazine]-2',7-diamine (58% yield) was obtained as a light brown solid. MS (ISP): m/z=268.3 [M+H]+.
Intermediate A7.2

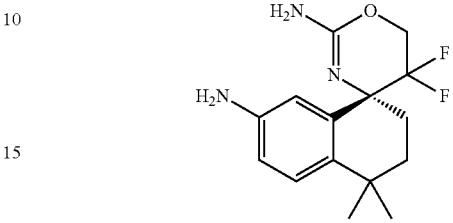

Starting from (R)-5',5'-difluoro-4,4-dimethyl-7-nitro-3,4,5',6'-tetrahydro-2H-spiro[naphthalene-1,4'-[1,3]oxazin]-2'-amine (intermediate A6.3), the product (R)-5',5'-difluoro-4,4-dimethyl-3,4,5',6'-tetrahydro-2H-spiro[naphthalene-1,4'-[1,3]oxazine]-2',7-diamine (88% yield) was obtained as a pale yellow foam. MS (ISP): m/z=296.4 [M+H]+.
Intermediate A7.3

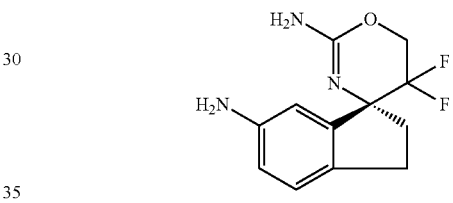

Starting from (R)-5',5'-difluoro-6-nitro-2,3,5',6'-tetrahydrospiro[indene-1,4'-[1,3]oxazin]-2'-amine (intermediate A6.6), the product (R)-5',5'-difluoro-2,3,5',6'-tetrahydrospiro[indene-1,4'-[1,3]oxazine]-2',6-diamine (75% yield) was obtained as a yellow sticky liquid. MS (ISP): m/z=254.0 [M+H]+.

Example 1

(R)-7-(5-Chloropyridin-3-yl)-5',5'-difluoro-3,4,5',6'-tetrahydro-2H-spiro[naphthalene-1,4'-[1,3]oxazin]-2'-amine In a tube a mixture of (R)-7-bromo-5',5'-difluoro-3,4,5',6'-tetrahydro-2H-spiro[naphthalene-1,4'-[1,3]oxazin]-2'-amine (intermediate A6.1) (35 mg, 106 µmol), 5-chloropyridin-3-ylboronic acid (17 mg, 106 µmol), and cesium carbonate (138 mg, 423 µmol) in tetrahydrofuran (2.8 ml) and water (1.4 ml) was purged with argon for 5 minutes. Thereafter, [1,1'-bis(diphenylphosphino)ferrocene]dichloropalladium(II) (3.9 mg, 5.3 µmol) was added, the tube was sealed and the mixture heated at 80° C. for 25 minutes. For the workup, the reaction mixture was diluted with ethyl acetate and washed with water. The organic layer was separated, dried over sodium sulphate and evaporated at reduced pressure. The residue was purified by chromatography on silica gel using a gradient of heptane/ethyl acetate=100:0 to 0:100 as the eluent. The (R)-5-(2'-amino-4,4,5',5'-tetrafluoro-3,4,5',6'-tetrahydro-2H-spiro[naphthalene-1,4'-[1,3]oxazine]-7-yl)nicotinonitrile (24 mg, 63% yield) was obtained as an off-white solid. MS (ISP): m/z=364.1 [M+H]+.

Example 2

(R)-5-(2'-Amino-5',5'-difluoro-3,4,5',6'-tetrahydro-2H-spiro[naphthalene-1,4'-[1,3]oxazine]-7-yl)nicotinonitrile In a manner analogous to that described in Example 1, the cross-coupling reaction of (R)-7-bromo-5',5'-difluoro-3,4,5',6'-tetrahydro-2H-spiro[naphthalene-1,4'-[1,3]oxazin]-2'-amine (intermediate A6.1) with 5-(4,4,5,5-tetramethyl-1,3,2-dioxaborolan-2-yl)nicotinonitrile yielded the title compound (72% yield) as an off-white solid. MS (ISP): m/z=355.2 [M+H]$^+$.

Example 3

(R)-7-(5-Chloropyridin-3-yl)-4,4,5',5'-tetrafluoro-3,4,5',6'-tetrahydro-2H-spiro[naphthalene-1,4'-[1,3]oxazin]-2'-amine In a manner analogous to that described in Example 1, the cross-coupling reaction of (R)-7-bromo-4,4,5',5'-tetrafluoro-3,4,5',6'-tetrahydro-2H-spiro[naphthalene-1,4'-[1,3]oxazin]-2'-amine (intermediate A6.4) with 5-chloropyridin-3-ylboronic acid yielded the title compound (28% yield) as a white solid. MS (ISP): m/z=399.9 [M+H]$^+$.

Example 4

(R)-4,4,5',5'-Tetrafluoro-7-(5-fluoropyridin-3-yl)-3,4,5',6'-tetrahydro-2H-spiro[naphthalene-1,4'-[1,3]oxazin]-2'-amine In a manner analogous to that described in Example 1, the cross-coupling reaction of (R)-7-bromo-4,4,5',5'-tetrafluoro-3,4,5',6'-tetrahydro-2H-spiro[naphthalene-1,4'-[1,3]oxazin]-2'-amine (intermediate A6.4) with 5-fluoropyridin-3-ylboronic acid yielded the title compound (32% yield) as a pale yellow solid. MS (ISP): m/z=384.0 [M+H]$^+$.

Example 5

(R)-5-(2'-Amino-4,4,5',5'-tetrafluoro-3,4,5',6'-tetrahydro-2H-spiro[naphthalene-1,4'-[1,3]oxazine]-7-yl)nicotinonitrile In a manner analogous to that described in Example 1, the cross-coupling reaction of (R)-7-bromo-4,4,5',5'-tetrafluoro-3,4,5',6'-tetrahydro-2H-spiro[naphthalene-1,4'-[1,3]oxazin]-2'-amine (intermediate A6.4) with 5-(4,4,5,5-tetramethyl-1,3,2-dioxaborolan-2-yl)nicotinonitrile yielded the title compound (51% yield) as a yellow solid. MS (ISP): m/z=390.3 [M]$^+$.

Example 6

(R)-6-(2-Chloropyridin-4-yl)-5',5'-difluoro-2,3,5',6'-tetrahydrospiro[indene-1,4'-[1,3]oxazin]-2'-amine In a manner analogous to that described in Example 1, the cross-coupling reaction of (R)-6-bromo-5',5'-difluoro-2,3,5',6'-tetrahydrospiro[indene-1,4'-[1,3]oxazin]-2'-amine (intermediate A6.5) with 5-chloropyridin-3-ylboronic acid in a 3:1-mixture of 1,2-dimethoxyethane and water as the solvent yielded the title compound (25% yield) as an off-white solid. MS (ISP): m/z=349.8 [M+H]$^+$.

Example 7

(R)-5',5'-Difluoro-6-(pyrimidin-5-yl)-2,3,5',6'-tetrahydrospiro[indene-1,4'-[1,3]oxazin]-2'-amine In a manner analogous to that described in Example 1, the cross-coupling reaction of (R)-6-bromo-5',5'-difluoro-2,3,5',6'-tetrahydrospiro[indene-1,4'-[1,3]oxazin]-2'-amine (intermediate A6.5) with pyrimidin-5-ylboronic acid in a 3:1-mixture of 1,2-dimethoxyethane and water as the solvent yielded the title compound (19% yield) as an off-white solid. MS (ISP): m/z=317.0 [M+H]$^+$.

Example 8

(R)-6-(3,5-Dichlorophenyl)-5',5'-difluoro-2,3,5',6'-tetrahydrospiro[indene-1,4'-[1,3]oxazin]-2'-amine In a manner analogous to that described in Example 1, the cross-coupling reaction of (R)-6-bromo-5',5'-difluoro-2,3,5',6'-tetrahydrospiro[indene-1,4'-[1,3]oxazin]-2'-amine (intermediate A6.5) with 3,5-dichlorophenylboronic acid in a 3:1-mixture of 1,2-dimethoxyethane and water as the solvent yielded the title compound (15% yield) as an off-white solid. MS (ISP): m/z=382.8 [M+H]$^+$.

Example 9

(R)-6-(5-Chloropyridin-3-yl)-5',5'-difluoro-2,3,5',6'-tetrahydrospiro[indene-1,4'-[1,3]oxazin]-2'-amine In a manner analogous to that described in Example 1, the cross-coupling reaction of (R)-6-bromo-5',5'-difluoro-2,3,5',6'-tetrahydrospiro[indene-1,4'-[1,3]oxazin]-2'-amine (intermediate A6.5) with 5-chloropyridin-3-ylboronic acid in a 3:1-mixture of 1,2-dimethoxyethane and water as the solvent yielded the title compound (19% yield) as a white solid. MS (ISP): m/z=349.8 [M+H]$^+$.

Example 10

(R)-3-(2'-Amino-5',5'-difluoro-2,3,5',6'-tetrahydrospiro[indene-1,4'-[1,3]oxazine]-6-yl)benzonitrile In a manner analogous to that described in Example 1, the cross-coupling reaction of (R)-6-bromo-5',5'-difluoro-2,3,5',6'-tetrahydrospiro[indene-1,4'-[1,3]oxazin]-2'-amine (intermediate A6.5) with 3-cyanophenylboronic acid in a 3:1-mixture of 1,2-dimethoxyethane and water as the solvent yielded the title compound (10% yield) as an off-white solid. MS (ISP): m/z=340.2 [M+H]$^+$.

Example 11

(R)-5-(2'-Amino-5',5'-difluoro-2,3,5',6'-tetrahydrospiro[indene-1,4'-[1,3]oxazine]-6-yl)nicotinonitrile In a manner analogous to that described in Example 1, the cross-coupling reaction of (R)-6-bromo-5',5'-difluoro-2,3,5',6'-tetrahydrospiro[indene-1,4'-[1,3]oxazin]-2'-amine (intermediate A6.5) with 5-cyanopyridin-3-ylboronic acid in a 3:1-mixture of 1,2-dimethoxyethane and water as the solvent yielded the title compound as an off-white solid.

General Procedure for the Preparation of Amides of Formula I.2:

A solution of the carboxylic acid (0.23 mmol) in methanol (5 ml) was cooled to 0° C. 4-(4,6-Dimethoxy[1.3.5]triazin-2-yl)-4-methylmorpholinium chloride hydrate (DMTMM) (80 mg, 0.27 mmol) was added and the solution was stirred at 0° C. for 30 minutes. Thereafter, a solution of the intermediate diamine A8 (0.21 mmol) in methanol (5 ml) was added dropwise at 0° C. via syringe. The reaction mixture was stirred at 23° C. for 18-60 hours. For the workup, the reaction mixture was poured into a solution of sodium carbonate (1M) followed by the extraction with ethyl acetate. The organic layer was separated, washed with brine and dried over sodium sulphate. Removal of the solvent at reduced pressure left a residue which was purified by chromatography on silica gel or on a silica-NH$_2$ phase using a mixture of dichloromethane and methanol (0-10%) to give the pure amides of formula I.

Example 12

(R)—N-(2'-Amino-5',5'-difluoro-3,4,5',6'-tetrahydro-2H-spiro[naphthalene-1,4'-[1,3]oxazine]-7-yl)-5-chloropicolinamide The condensation of (R)-5',5'-difluoro-3,4,5',6'-tetrahydro-2H-spiro[naphthalene-1,4'-[1,3]oxazine]-2',7-diamine (intermediate A7.1) and 5-chloropicolinic acid yielded the title compound (42% yield) as a white solid. MS (ISP): m/z=407.2 [M+H]$^+$.

Example 13

(R)—N-(2'-Amino-5',5'-difluoro-3,4,5',6'-tetrahydro-2H-spiro[naphthalene-1,4'-[1,3]oxazine]-7-yl)-5-cyanopicolinamide The condensation of (R)-5',5'-difluoro-3,4,5',6'-tetrahydro-2H-spiro[naphthalene-1,4'-[1,3]oxazine]-2',7-diamine (intermediate A7.1) and 5-cyanopicolinic acid yielded the title compound (38% yield) as a white solid. MS (ISP): m/z=398.2 [M+H]$^+$.

Example 14

(R)—N-(2'-Amino-5',5'-difluoro-4,4-dimethyl-3,4,5',6'-tetrahydro-2H-spiro[naphthalene-1,4'-[1,3]oxazine]-7-yl)-5-cyanopicolinamide The condensation of (R)-5',5'-difluoro-4,4-dimethyl-3,4,5',6'-tetrahydro-2H-spiro[naphthalene-1,4'-[1,3]oxazine]-2',7-diamine (intermediate A7.2) and 5-cyanopicolinic acid yielded the title compound (65% yield) as a pale yellow solid. MS (ISP): m/z=426.0 [M+H]$^+$.

Example 15

(R)—N-(2'-Amino-5',5'-difluoro-2,3,5',6'-tetrahydrospiro[indene-1,4'-[1,3]oxazine]-6-yl)-5-cyanopicolinamide The condensation of (R)-5',5'-difluoro-2,3,5',6'-tetrahydrospiro[indene-1,4'-[1,3]oxazine]-2',6-diamine (intermediate A7.3) and 5-cyanopicolinic acid yielded the title compound (27% yield) as an off-white solid. MS (ISP): m/z=384.2 [M+H]$^+$.

Example 16

(R)—N-(2'-Amino-5',5'-difluoro-2,3,5',6'-tetrahydrospiro[indene-1,4'-[1,3]oxazine]-6-yl)-5-chloropicolinamide The condensation of (R)-5',5'-difluoro-2,3,5',6'-tetrahydrospiro[indene-1,4'-[1,3]oxazine]-2',6-diamine (intermediate A7.3) and 5-chloropicolinic acid yielded the title compound (16% yield) as an off-white solid. MS (ISP): m/z=393.0 [M+H]$^+$.

Example 17

(R)—N-(2'-Amino-5',5'-difluoro-2,3,5',6'-tetrahydrospiro[indene-1,4'-[1,3]oxazine]-6-yl)-5-fluoropicolinamide The condensation of (R)-5',5'-difluoro-2,3,5',6'-tetrahydrospiro[indene-1,4'-[1,3]oxazine]-2',6-diamine (intermediate A7.3) and 5-fluoropicolinic acid yielded the title compound (17% yield) as an off-white solid. MS (ISP): m/z=377.2 [M+H]$^+$.

Example 18

(R)—N-(2'-Amino-5',5'-difluoro-2,3,5',6'-tetrahydrospiro[indene-1,4'-[1,3]oxazine]-6-yl)-5-(trifluoromethyl)picolinamide The condensation of (R)-5',5'-difluoro-2,3,5',6'-tetrahydrospiro[indene-1,4'-[1,3]oxazine]-2',6-diamine (intermediate A7.3) and 5-(trifluoromethyl)picolinic acid yielded the title compound (15% yield) as an off-white solid. MS (ISP): m/z=427.2 [M+H]$^+$.

Synthesis of the intermediate sulfinyl imines B2
General Procedure

To a solution of the (R)-(+)-tert-butylsulfinamide (66 mmol) in tetrahydrofuran (350 ml) was added subsequently the ketone B1 (72.6 mmol) and titanium(IV)ethoxide (132 mmol) and the solution was stirred at reflux temperature for 5 h. The mixture was cooled to 22° C., treated with brine (400 ml), the suspension was stirred for 10 min and filtered over Dicalite®. The layers were separated, the aqueous layer was extracted with ethyl acetate, the combined organic layers were washed with water, dried and concentrated in vacuo. The residue was purified by chromatography on silica using cylohexane/ethyl acetate as the eluent to give the pure sulfinyl imine B2.

Intermediate B2.1

(X=O; W=—CR$^{2a}$, R$^{2b}$; R$^{2a}$, R$^{2b}$=H; p=1)

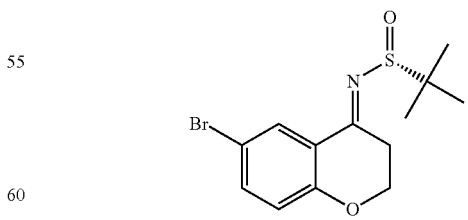

Starting from 6-bromo-chroman-4-one {CAS[49660-57-3]} (intermediate B1.1), the product (R)-2-methyl-propane-2-sulfinic acid [6-bromo-chroman-(4E)-ylidene]-amide (69% yield) was obtained as a pale yellow oil. MS (ISP): m/z=332.0 [M+H]$^+$.

Intermediate B2.2

($X=O$; $W=\!\!=\!\!CR^{2a},R^{2b}$; $R^{2a},R^{2b}=H$; $p=1$)

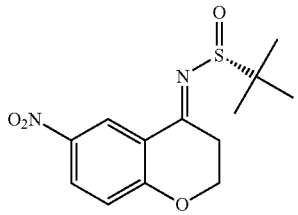 [SMILES: CC(C)(C)[S@@](=O)/N=C1\CCOc2ccc([N+](=O)[O-])cc21]

Starting from 6-nitro-chroman-4-one {CAS[68043-53-8]} (intermediate B1.2), the product (R)-2-methyl-propane-2-sulfinic acid [6-nitro-chroman-(4E)-ylidene]-amide (85% yield) was obtained as a yellow oil. MS (ISP): m/z=297.2 [M+H]$^+$.

Intermediate B2.3

($X=O$; $W=\!\!=\!\!CR^{2a},R^{2b}$; $R^{2a}$=phenyl, $R^{2b}$=H; $p=1$)

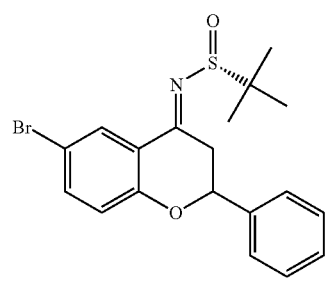 [SMILES: CC(C)(C)[S@@](=O)/N=C1\CC(c2ccccc2)Oc2ccc(Br)cc21]

Starting from (RS)-6-bromo-2-phenyl-chroman-4-one {CAS[56414-11-0]; WO2010021680} (intermediate B1.3), the product (R)-2-methyl-propane-2-sulfinic acid [(RS)-6-bromo-2-phenyl-chroman-(4E)-ylidene]-amide (64% yield) was obtained as a yellow solid. MS (ISP): m/z=407 [M+H]$^+$.

Intermediate B2.4

($X=O$; $W=\!\!=\!\!CR^{2a},R^{2b}$; $R^{2a}$=phenyl, $R^{2b}$=H; $p=1$)

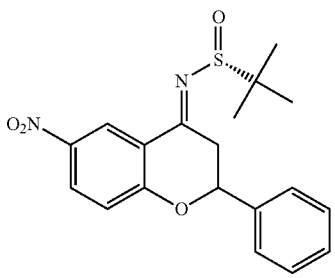 [SMILES: CC(C)(C)[S@@](=O)/N=C1\CC(c2ccccc2)Oc2ccc([N+](=O)[O-])cc21]

Starting from (RS)-6-nitro-2-phenyl-chroman-4-one {CAS[3034-03-5]} (intermediate B1.4), the product (R)-2-methyl-propane-2-sulfinic acid [(RS)-6-nitro-2-phenyl-chroman-(4E)-ylidene]-amide (43% yield) was obtained as a yellow solid. MS (ISP): m/z=373 [M+H]$^+$.

Intermediate B2.5

($X=O$; $W=\!\!=\!\!CR^{2a},R^{2b}$; $R^{2a},R^{2b}$=methyl, $R^{2b}$=H; $p=1$)

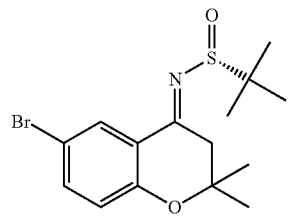 [SMILES: CC1(C)C/C(=N\[S@](=O)C(C)(C)C)c2cc(Br)ccc2O1]

Starting from 6-bromo-2,2-dimethyl-chroman-4-one {CAS[99853-21-1]; WO2010021680} (intermediate B1.5), the product (R)-2-methyl-propane-2-sulfinic acid [6-bromo-2,2-dimethyl-chroman-(4E)-ylidene]-amide (55% yield) was obtained as a yellow solid. MS (ISP): m/z=358.1 [M+H]$^+$ and 360.2 [M+2+H]$^+$.

Intermediate B2.6

($X=O$; $W=\!\!=\!\!CR^{2a},R^{2b}$; $R^{2a},R^{2b}$=methyl, $R^{2b}$=H; $p=1$)

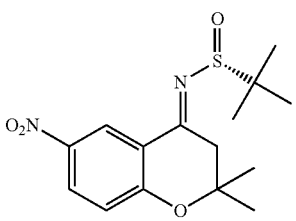 [SMILES: CC1(C)C/C(=N\[S@](=O)C(C)(C)C)c2cc([N+](=O)[O-])ccc2O1]

Starting from 2,2-dimethyl-6-nitro-chroman-4-one {CAS [111478-49-01]} (intermediate B1.6), the product (R)-2-methyl-propane-2-sulfinic acid [2,2-dimethyl-6-nitro-chroman-(4E)-ylidene]-amide (64% yield) was obtained as a yellow solid. MS (ISP): m/z=325.2 [M+H]$^+$.

Intermediate B2.7

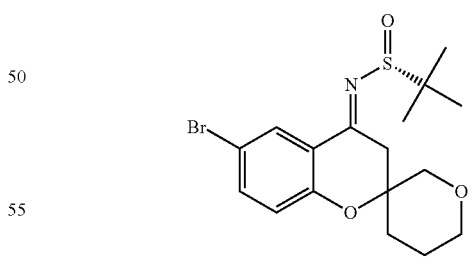

Starting from 6-bromo-2',4',5',6'-tetrahydrospiro[chroman-2,3'-pyran]-4-one {CAS[1212017-68-9]; WO2010021680} (intermediate B1.7), the product (R,E)-N-(6-bromo-2',4',5',6'-tetrahydrospiro[chroman-2,3'-pyran]-4-ylidene)-2-methylpropane-2-sulfinamide (67% yield) was obtained as a yellow solid. MS (ISP): m/z=400.1 [M+H]$^+$ and 402.2 [M+H]$^+$.

Intermediate B2.8
(X=S; W=—CR$^{2a}$, R$^{2b}$; R$^{2a}$, R$^{2b}$=H; p=1)

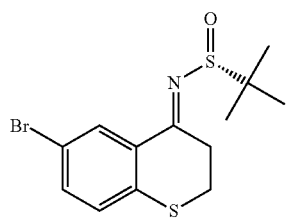 [SMILES: CC(C)(C)[S@@](=O)/N=C1\CCSc2ccc(Br)cc21]

Starting from 6-bromo-thiochroman-4-one {CAS[13735-13-2]} (intermediate B1.8), the product (R)-2-methyl-propane-2-sulfinic acid [6-bromo-thiochroman-(4E)-ylidene]-amide (73% yield) was obtained as a yellow solid. MS (ISP): m/z=346.0 [M+H]$^{+}$.

Synthesis of the Intermediate Sulfinamide Esters B3
General Procedure (Via Reformatsky Reaction)

In a dry apparatus a suspension of freshly activated zinc powder (1.63 g, 24.9 mmol) in dry tetrahydrofuran (70 ml) was heated under an inert atmosphere to reflux. A solution of the sulfinyl imine B2 (24.9 mmol) and the bromo-acetate (24.9 mmol) in dry tetrahydrofuran (15 ml) was added dropwise over a period of 15 min and the suspension was heated to reflux for 5 h. The cooled mixture was partitioned between aqueous saturated ammonium chloride and ethyl acetate, the organic layer was dried and evaporated. The crude material was purified by flash chromatography using heptane/ethyl acetate as the eluent to give the sulfinamide ester B3.

Intermediate B3.1

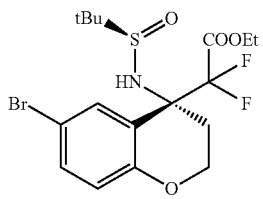 [SMILES: CCOC(=O)C(F)(F)[C@@]1(N[S@](=O)C(C)(C)C)CCOc2ccc(Br)cc21]

Starting from (R)-2-methyl-propane-2-sulfinic acid [6-bromo-chroman-(4E)-ylidene]-amide (intermediate B2.1), the product [(R)-6-bromo-4-((R)-2-methyl-propane-2-sulfinylamino)-chroman-4-yl]-difluoro-acetic acid ethyl ester (63% yield) was obtained as a yellow oil. MS (ISP): m/z=456.1 [M+H]$^{+}$.

Intermediate B3.2

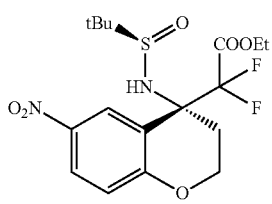 [SMILES: CCOC(=O)C(F)(F)[C@@]1(N[S@](=O)C(C)(C)C)CCOc2ccc([N+](=O)[O-])cc21]

Starting from (R)-2-methyl-propane-2-sulfinic acid [6-nitro-chroman-(4E)-ylidene]-amide (intermediate B2.2), the product difluoro-[(R)-4-((R)-2-methyl-propane-2-sulfinylamino)-6-nitro-chroman-4-yl]-acetic acid ethyl ester (52% yield) was obtained as a red oil.

Intermediate B3.3

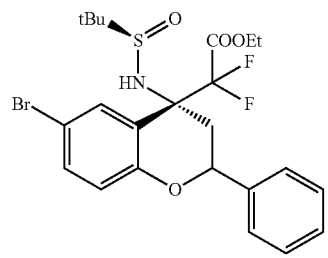

Starting from (R)-2-methyl-propane-2-sulfinic acid [(RS)-6-bromo-2-phenyl-chroman-(4E)-ylidene]-amide (intermediate B2.3), the product [(2RS,4R)-6-bromo-4-((R)-2-methyl-propane-2-sulfinylamino)-2-phenyl-chroman-4-yl]-difluoro-acetic acid ethyl ester (82% yield) was obtained as a yellow solid. MS (ISP): m/z=532 [M+H]$^{+}$.

Intermediate B3.4

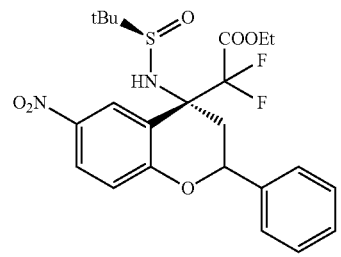

Starting from (R)-2-methyl-propane-2-sulfinic acid [(RS)-6-nitro-2-phenyl-chroman-(4E)-ylidene]-amide (intermediate B2.4), the product difluoro-[(2RS,4R)-4-((R)-2-methyl-propane-2-sulfinylamino)-6-nitro-2-phenyl-chroman-4-yl]-acetic acid ethyl ester (42% yield) was obtained as a yellow solid. MS (ISP): m/z=497 [M+H]$^{+}$.

Intermediate B3.5

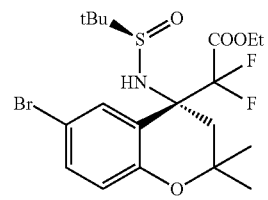 [SMILES: CCOC(=O)C(F)(F)[C@@]1(N[S@](=O)C(C)(C)C)CC(C)(C)Oc2ccc(Br)cc21]

Starting from (R)-2-methyl-propane-2-sulfinic acid [6-bromo-2,2-dimethyl-chroman-(4E)-ylidene]-amide (intermediate B2.5), the product [(R)-6-bromo-2,2-dimethyl-4-((R)-2-methyl-propane-2-sulfinylamino)-chroman-4-yl]-difluoro-acetic acid ethyl ester (53% yield) was obtained as a pale yellow solid. MS (ISP): m/z=482.2 [M+H]$^{+}$ and 484.3 [M+2+H]$^{+}$.

Intermediate B3.6

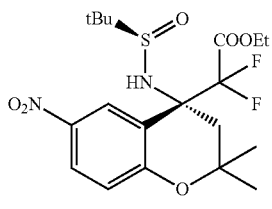 [SMILES: CCOC(=O)C(F)(F)[C@@]1(N[S@](=O)C(C)(C)C)CC(C)(C)Oc2ccc([N+](=O)[O-])cc21]

Starting from (R)-2-methyl-propane-2-sulfinic acid [2,2-dimethyl-6-nitro-chroman-(4E)-ylidene]-amide (intermediate B2.6), the product [(R)-2,2-dimethyl-6-nitro-4-((R)-2-methyl-propane-2-sulfinylamino)-chroman-4-yl]-difluoro-acetic acid ethyl ester (56% yield) was obtained as a red oil. MS (ISP): m/z=449.2 [M+H]$^+$.

Intermediate B3.7

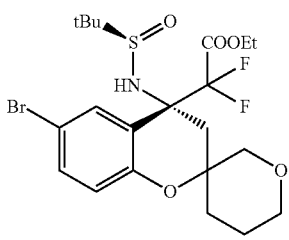

Starting from (R,E)-N-(6-bromo-2',4',5',6'-tetrahydrospiro[chroman-2,3'-pyran]-4-ylidene)-2-methylpropane-2-sulfinamide (intermediate B2.7), the product ethyl 2-((4R)-6-bromo-4-((R)-1,1-dimethylethylsulfinamido)-2',4',5',6'-tetrahydrospiro[chroman-2,3'-pyran]-4-yl)-2,2-difluoroacetate (58% yield) was obtained as a pale yellow foam. MS (ISP): m/z=524.2 [M+H]$^+$ and 526.1 [M+H]$^+$.

Intermediate B3.8

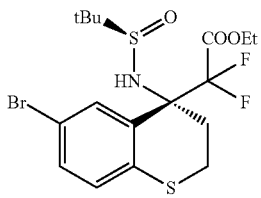 [SMILES: CCOC(=O)C(F)(F)[C@@]1(N[S@](=O)C(C)(C)C)CCSc2ccc(Br)cc21]

Starting from (R)-2-methyl-propane-2-sulfinic acid [6-bromo-thiochroman-(4E)-ylidene]-amide (intermediate B2.8), the product [(R)-6-bromo-4-((R)-2-methyl-propane-2-sulfinylamino)-thiochroman-4-yl]-difluoro-acetic acid ethyl ester (77% yield) was obtained as a yellow, viscous oil. MS (ISP): m/z=470.2 [M+H]$^+$ and 472.2 [M+2+H]$^+$.

Synthesis of the Intermediate Sulfinamide Alcohols B4

General Procedure

A solution of the sulfinamide ester B3 (12.7 mmol) in dry tetrahydrofuran (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate as the eluent to give the pure intermediate sulfinamide alcohol B4.

Intermediate B4.1

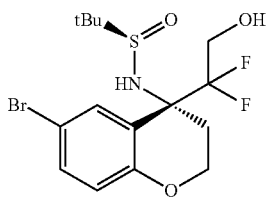 [SMILES: CC(C)(C)[S@@](=O)N[C@]1(C(F)(F)CO)CCOc2ccc(Br)cc21]

Starting from [(R)-6-bromo-4-((R)-2-methyl-propane-2-sulfinylamino)-chroman-4-yl]-difluoro-acetic acid ethyl ester (intermediate B3.1), the product (R)-2-methyl-propane-2-sulfinic acid [(R)-6-bromo-4-(1,1-difluoro-2-hydroxy-ethyl)-chroman-4-yl]-amide (96% yield) was obtained as a white solid. MS (ISP): m/z=414.1 [M+H]$^+$.

Intermediate B4.2

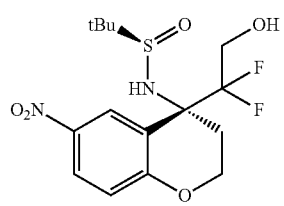 [SMILES: CC(C)(C)[S@@](=O)N[C@]1(C(F)(F)CO)CCOc2ccc([N+](=O)[O-])cc21]

Starting from difluoro-[(R)-4-((R)-2-methyl-propane-2-sulfinylamino)-6-nitro-chroman-4-yl]-acetic acid ethyl ester (intermediate B3.2), the product (R)-2-methyl-propane-2-sulfinic acid [(R)-4-(1,1-difluoro-2-hydroxy-ethyl)-6-nitro-chroman-4-yl]-amide (78% yield) was obtained as a red oil. MS (ISP): m/z=379.2 [M+H]$^+$.

Intermediate B4.3

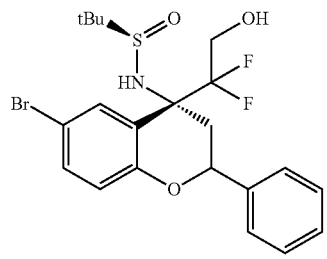

Starting from [(2RS,4R)-6-bromo-4-((R)-2-methyl-propane-2-sulfinylamino)-2-phenyl-chroman-4-yl]-difluoro-acetic acid ethyl ester (intermediate B3.3), the product (R)-2-methyl-propane-2-sulfinic acid [(2RS,4R)-6-bromo-4-(1,1-difluoro-2-hydroxy-ethyl)-2-phenyl-chroman-4-yl]-amide (78% yield) was obtained as a white solid. MS (ISP): m/z=490 [M+H]$^+$.

Intermediate B4.4

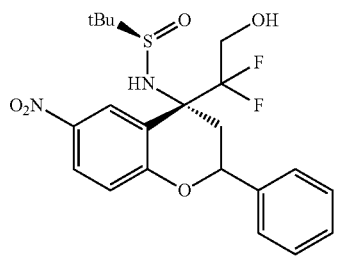

Starting from difluoro-[(2RS,4R)-4-((R)-2-methyl-propane-2-sulfinylamino)-6-nitro-2-phenyl-chroman-4-yl]-acetic acid ethyl ester (intermediate B3.4), the product (R)-2-methyl-propane-2-sulfinic acid [(2RS,4R)-4-(1,1-difluoro-2-hydroxy-ethyl)-6-nitro-2-phenyl-chroman-4-yl]-amide (64% yield) was obtained as a yellow sticky liquid. MS (ISP): m/z=455 [M+H]$^+$.

Intermediate B4.5

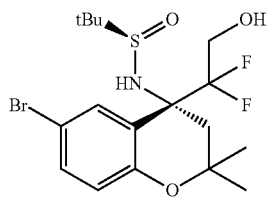 [SMILES: CC1(C)C[C@](N[S@](=O)C(C)(C)C)(C(F)(F)CO)c2cc(Br)ccc2O1]

Starting from [(R)-6-bromo-2,2-dimethyl-4-((R)-2-methyl-propane-2-sulfinylamino)-chroman-4-yl]-difluoro-acetic acid ethyl ester (intermediate B3.5), the product (R)-2-methyl-propane-2-sulfinic acid [(R)-6-bromo-4-(1,1-difluoro-2-hydroxy-ethyl)-2,2-dimethyl-chroman-4-yl]-amide (99% yield) was obtained as a white powder. MS (ISP): m/z=440.2 [M+H]$^+$ and 442.2 [M+2+H]$^+$.

Intermediate B4.6

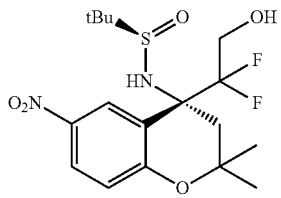 [SMILES: CC1(C)C[C@](N[S@](=O)C(C)(C)C)(C(F)(F)CO)c2cc([N+](=O)[O-])ccc2O1]

Starting from [(R)-2,2-dimethyl-6-nitro-4-((R)-2-methyl-propane-2-sulfinylamino)-chroman-4-yl]-difluoro-acetic acid ethyl ester (intermediate B3.6), the product (R)-2-methyl-propane-2-sulfinic acid [(R)-4-(1,1-difluoro-2-hydroxy-ethyl)-2,2-dimethyl-6-nitro-chroman-4-yl]-amide (59% yield) was obtained as a red oil. MS (ISP): m/z=407.3 [M+H]$^+$.

Intermediate B4.7

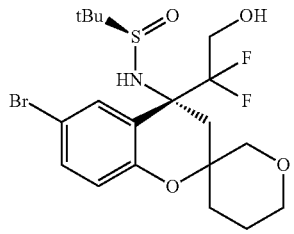

Starting from ethyl 2-((4R)-6-bromo-4-((R)-1,1-dimethylethylsulfinamido)-2',4',5',6'-tetrahydrospiro[chroman-2,3'-pyran]-4-yl)-2,2-difluoroacetate (intermediate B3.7), the product (R)—N-((4R)-6-bromo-4-(1,1-difluoro-2-hydroxyethyl)-2',4',5',6'-tetrahydrospiro[chroman-2,3'-pyran]-4-yl)-2-methylpropane-2-sulfinamide (98% yield) was obtained as a white solid. MS (ISP): m/z=482.2 [M+H]$^+$ and 484.1 [M+H]$^+$.

Intermediate B4.8

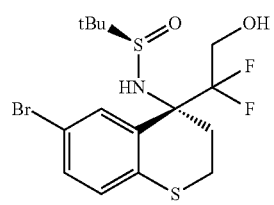

Starting from [(R)-6-bromo-4-((R)-2-methyl-propane-2-sulfinylamino)-thiochroman-4-yl]-difluoro-acetic acid ethyl ester (intermediate B3.8), the product (R)-2-methyl-propane-2-sulfinic acid [(R)-6-bromo-4-(1,1-difluoro-2-hydroxy-ethyl)-thiochroman-4-yl]-amide (94% yield) was obtained as a white foam. MS (ISP): m/z=428.2 [M+H]$^+$ and 430.2 [M+2+H]$^+$.

Synthesis of the Intermediate Amino Alcohols B5
General Procedure:

A solution of the sulfinamide alcohols B4 (10.3 mmol) in methanol or tetrahydrofuran (30 to 60 ml) was treated with a solution of hydrochloric acid in 1,4-dioxane (4 M, 10-13 ml) and stirring was continued at 23° C. for 2 to 18 h. The mixture was partitioned between ethyl acetate and an aqueous solution of sodium carbonate (2 M), the organic layer was dried over sodium sulphate, filtered and evaporated to give a residue which was purified by chromatography on silica using a mixture of n-heptane and ethyl acetate as the eluent to give the pure aminoalcohols B5.

Intermediate B5.1

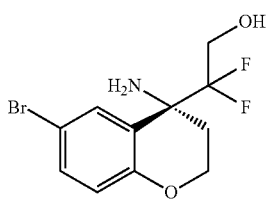 [SMILES: N[C@]1(C(F)(F)CO)CCOc2ccc(Br)cc21]

Starting from (R)-2-methyl-propane-2-sulfinic acid [(R)-6-bromo-4-(1,1-difluoro-2-hydroxy-ethyl)-chroman-4-yl]-amid (intermediate B4.1), the product 2-((R)-4-amino-6-bromo-chroman-4-yl)-2,2-difluoro-ethanol (73% yield) was obtained as a pale yellow oil.

Intermediate B5.2

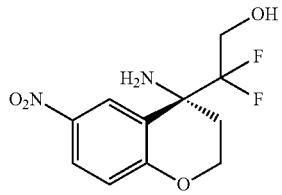 [SMILES: N[C@]1(C(F)(F)CO)CCOc2ccc([N+](=O)[O-])cc21]

Starting from (R)-2-methyl-propane-2-sulfinic acid [(R)-4-(1,1-difluoro-2-hydroxy-ethyl)-6-nitro-chroman-4-yl]-amide (intermediate B4.2), the product 2-((R)-4-amino-6-nitro-chroman-4-yl)-2,2-difluoro-ethanol (25% yield) was obtained as a yellow oil. MS (ISP): m/z=275.1 [M+H]⁺.

Intermediate B5.3

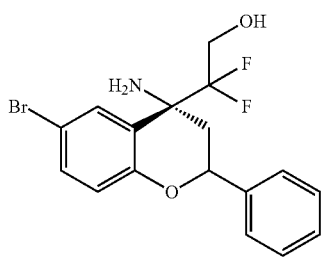

Starting from (R)-2-methyl-propane-2-sulfinic acid [(2RS,4R)-6-bromo-4-(1,1-difluoro-2-hydroxy-ethyl)-2-phenyl-chroman-4-yl]-amide (intermediate B4.3), the product 2-((2RS,4R)-4-amino-6-bromo-2-phenyl-chroman-4-yl)-2,2-difluoro-ethanol (70% yield) was obtained.

Intermediate B5.4

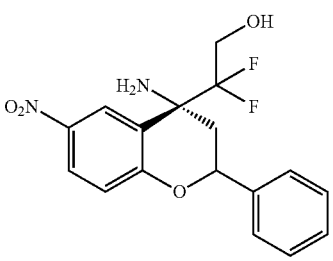

Starting from (R)-2-methyl-propane-2-sulfinic acid [(2RS,4R)-4-(1,1-difluoro-2-hydroxy-ethyl)-6-nitro-2-phenyl-chroman-4-yl]-amide (intermediate B4.4), the product 2-((2RS,4R)-4-amino-6-nitro-2-phenyl-chroman-4-yl)-2,2-difluoro-ethanol (50% yield) was obtained as a pale yellow solid. MS (ISP): m/z=351.2 [M+H]⁺.

Intermediate B5.5

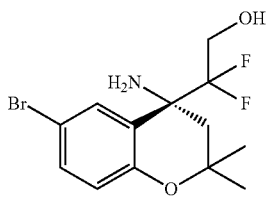 [SMILES: CC1(C)C[C@](N)(C(F)(F)CO)c2cc(Br)ccc2O1]

Starting from (R)-2-methyl-propane-2-sulfinic acid [(R)-6-bromo-4-(1,1-difluoro-2-hydroxy-ethyl)-2,2-dimethyl-chroman-4-yl]-amide (intermediate B4.5), the product 2-((R)-4-amino-6-bromo-2,2-dimethyl-chroman-4-yl)-2,2-difluoro-ethanol (47% yield) was obtained as a viscous, pale yellow oil. MS (ISP): m/z=319.0 [M+H]⁺ and 321.0 [M+2+H]⁺.

Intermediate B5.6

Starting from (R)-2-methyl-propane-2-sulfinic acid [(R)-4-(1,1-difluoro-2-hydroxy-ethyl)-2,2-dimethyl-6-nitro-chroman-4-yl]-amide (intermediate B4.6), the product 2-((R)-4-amino-2,2-dimethyl-6-nitro-chroman-4-yl)-2,2-difluoro-ethanol (69% yield) was obtained as a red oil. MS (ISP): m/z=303.1 [M+H]⁺.

Intermediates B5.7A and B5.7B

B5.7A

B5.7B

Starting from (R)—N-((4R)-6-bromo-4-(1,1-difluoro-2-hydroxyethyl)-2',4',5',6'-tetrahydrospiro[chroman-2,3'-pyran]-4-yl)-2-methylpropane-2-sulfinamide (intermediate B4.7), and after chromatography on silica gel using a gradient of heptane/ethyl acetate=100:0 to =:100 as the eluent the 2-((2R,4R)-4-amino-6-bromo-2',4',5',6'-tetrahydrospiro[chroman-2,3'-pyran]-4-yl)-2,2-difluoroethanol (47% yield)

intermediate B5.7A) was obtained as the first eluting isomer as a white foam; MS (ISP): m/z=378.0 [M+H]⁺ and 380.0 [M+2+H]⁺. The second eluting isomer, 2-((2S,4R)-4-amino-6-bromo-2',4',5',6'-tetrahydrospiro[chroman-2,3'-pyran]-4-yl)-2,2-difluoro ethanol (27% yield) (intermediate B5.7B) was also obtained as a white foam; MS (ISP): m/z=378.0 [M+H]⁺ and 380.0 [M+2+H]⁺.

Intermediate B5.8

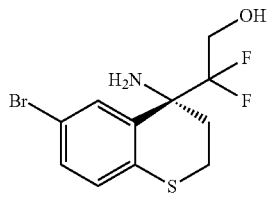

Starting from (R)-2-methyl-propane-2-sulfinic acid [(R)-6-bromo-4-(1,1-difluoro-2-hydroxy-ethyl)-thiochroman-4-yl]-amide (intermediate B4.8), the product 2-((R)-4-amino-6-bromo-thiochroman-4-yl)-2,2-difluoro-ethanol (85% yield) was obtained as a colorless, viscous oil. MS (ISP): m/z=324.0 [M+H]⁺.

Syntheses of the Intermediate Amino Oxazines B6

General Procedure

A dried tube was charged with a mixture of the amino alcohol B5 (18.8 mmol), cyanogen bromide (33.9 mmol) and ethanol (61 ml). The tube was sealed and heated at 90° C. for 16 hours. For the workup, the reaction mixture was cooled and evaporated at reduced pressure. The residue was partitioned between ethyl acetate (150 ml) and a saturated aqueous solution of sodium carbonate (50 ml). The aqueous layer was separated and re-extracted with ethyl acetate (2×50 ml). The organic layers were washed with brine (50 ml), then combined, dried over sodium sulphate and evaporated at reduced pressure. The product was used in the next step without further purification.

Intermediate B6.1

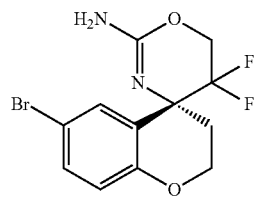

Starting from 2-((R)-4-amino-6-bromo-chroman-4-yl)-2,2-difluoro-ethanol (intermediate B5.1), the product (R)-6-bromo-5',5'-difluoro-5',6'-dihydrospiro[chroman-4,4'-[1,3]oxazin]-2'-amine (15% yield) was obtained as a colorless. MS (ISP): m/z=331.1 [M+H]⁺.

Intermediate B6.2

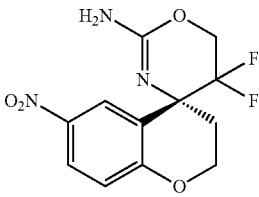 [SMILES: NC1=N[C@@]2(CCOc3ccc([N+](=O)[O-])cc32)C(F)(F)CO1]

Starting from 2-((R)-4-amino-6-nitro-chroman-4-yl)-2,2-difluoro-ethanol (intermediate B5.2), the product (R)-5',5'-difluoro-6-nitro-5',6'-dihydrospiro[chroman-4,4'-[1,3]oxazin]-2'-amine (24% yield) was obtained as a pale yellow solid. MS (ISP): m/z=300.1 [M+H]⁺.

Intermediate B6.3

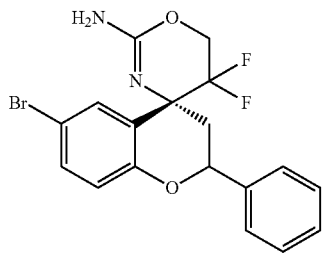

Starting from 2-((2RS,4R)-4-amino-6-bromo-2-phenyl-chroman-4-yl)-2,2-difluoro-ethanol (intermediate B5.3), the product (2RS,4R)-6-bromo-5',5'-difluoro-2-phenyl-5',6'-dihydrospiro[chroman-4,4'-[1,3]oxazin]-2'-amine (30% yield) was obtained.

Intermediate B6.4

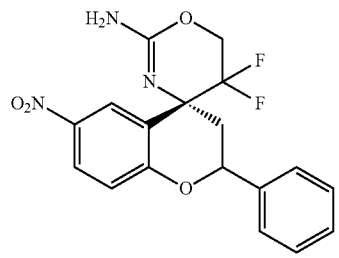

Starting from 2-((2RS,4R)-4-amino-6-nitro-2-phenyl-chroman-4-yl)-2,2-difluoro-ethanol (intermediate B5.4), the product (2RS,4R)-5',5'-difluoro-6-nitro-2-phenyl-5',6'-dihydrospiro[chroman-4,4'-[1,3]oxazin]-2'-amine was obtained.

Intermediate B6.5

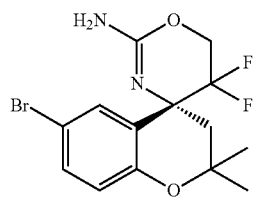 [SMILES: CC1(C)C[C@@]2(N=C(N)OCC2(F)F)c2cc(Br)ccc2O1]

Starting from 2-((R)-4-amino-6-bromo-2,2-dimethyl-chroman-4-yl)-2,2-difluoro-ethanol (intermediate B5.5), the product (R)-6-bromo-5',5'-difluoro-2,2-dimethyl-5',6'-dihydrospiro[chroman-4,4'-[1,3]oxazin]-2'-amine (35% yield) was obtained as a pale yellow solid. MS (ISP): m/z=361.1 [M+H]+ and 363.1 [M+2+H]+.

Intermediate B6.6

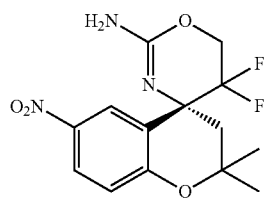 [SMILES: CC1(C)C[C@@]2(N=C(N)OCC2(F)F)c2cc([N+](=O)[O-])ccc2O1]

Starting from 2-((R)-4-amino-2,2-dimethyl-6-nitro-chroman-4-yl)-2,2-difluoro-ethanol (intermediate B5.6), the product (R)-5',5'-difluoro-2,2-dimethyl-6-nitro-5',6'-dihydrospiro[chroman-4,4'-[1,3]oxazin]-2'-amine (50% yield) was obtained as a yellow oil. MS (ISP): m/z=328.1 [M+H]+.

Intermediate B6.7

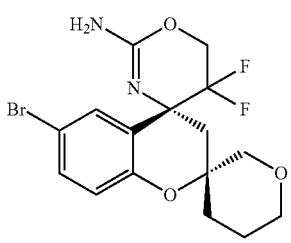 [SMILES: NC1=N[C@@]2(C[C@@]3(CCCOC3)Oc3ccc(Br)cc32)C(F)(F)CO1]

Starting from 2-((2R,4R)-4-amino-6-bromo-2',4',5',6'-tetrahydrospiro[chroman-2,3'-pyran]-4-yl)-2,2-difluoroethanol (intermediate B5.7A), the product (2'R,4R)-6'-bromo-5,5-difluoro-5,5'',6,6''-tetrahydro-4''H-dispiro[1,3-oxazine-4,4'-chromene-2',3''-pyran]-2-amine (49% yield) was obtained as a white foam; MS (ISP): m/z=403.3 [M+H]+ and 405.2 [M+2+H]+.

Intermediate B6.8

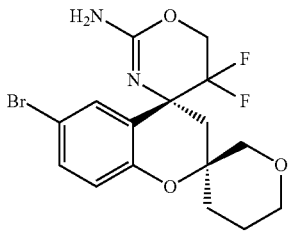 [SMILES: NC1=N[C@@]2(C[C@]3(CCCOC3)Oc3ccc(Br)cc32)C(F)(F)CO1]

Starting from 2-((2S,4R)-4-amino-6-bromo-2',4',5',6'-tetrahydro spiro[chroman-2,3'-pyran]-4-yl)-2,2-difluoroethanol (intermediate B5.7B), the product (2'S,4R)-6'-bromo-5,5-difluoro-5,5'',6,6''-tetrahydro-4''H-dispiro[1,3-oxazine-4,4'-chromene-2',3''-pyran]-2-amine (47% yield) was obtained as a white foam; MS (ISP): m/z=403.0 [M+H]+ and 405.0 [M+2+H]+.

Intermediate B6.9

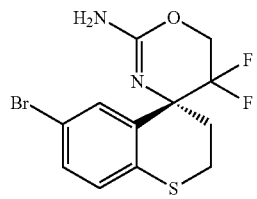

Starting from 2-((R)-4-amino-6-bromo-thiochroman-4-yl)-2,2-difluoro-ethanol (intermediate B5.9), the product (R)-6'-bromo-5,5-difluoro-5,6-dihydrospiro[[1,3]oxazine-4,4'-thiochroman]-2-amine (29% yield) was obtained as a colorless, waxy solid. MS (ISP): m/z=349.1 [M+H]+ and 351.0 [M+2+H]+.

Syntheses of Intermediate Anilines B7 (Via Reduction of Nitro Oxazines)

General Procedure

A solution of the nitro oxazine B6 (3 mmol) in ethanol (31 ml) was hydrogenated at atmospheric pressure using palladium (10% on carbon) (159 mg, 150 μmol) as the catalyst. After 90 minutes the reaction was complete. The reaction mixture was filtrated over a layer of Dicalit, which was washed with ethanol (3×20 ml). The combined solutions of ethanol were evaporated at reduced pressure. The product was engaged in the step without further purification.

Intermediate B7.1

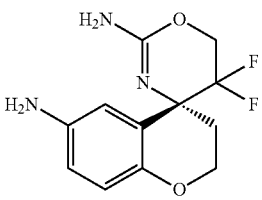

Starting from (R)-5',5'-difluoro-6-nitro-5',6'-dihydrospiro[chroman-4,4'-[1,3]oxazin]-2'-amine (intermediate B6.2), the product (R)-5',5'-difluoro-5',6'-dihydrospiro[chroman-4,4'-[1,3]oxazine]-2',6-diamine (67% yield) was obtained as a yellow solid. MS (ISP): m/z=270.3 [M+H]+.

Intermediate B7.2

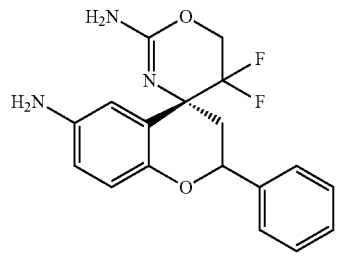

Starting from (2RS,4R)-5',5'-difluoro-6-nitro-2-phenyl-5',6'-dihydrospiro[chroman-4,4'-[1,3]oxazin]-2'-amine (intermediate B6.4), the product (2RS,4R)-5',5'-difluoro-2-phenyl-5',6'-dihydrospiro[chroman-4,4'-[1,3]oxazine]-2',6-diamine (81% yield) was obtained as a brown solid.

Intermediate B7.3

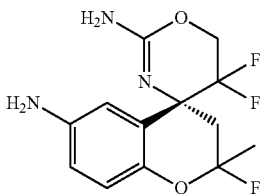

Starting from (R)-5',5'-difluoro-2,2-dimethyl-6-nitro-5',6'-dihydrospiro[chroman-4,4'-[1,3]oxazin]-2'-amine (intermediate B6.6), the product (R)-5',5'-difluoro-2,2-dimethyl-5',6'-dihydrospiro[chroman-4,4'-[1,3]oxazine]-2',6-diamine (64% yield) was obtained as a yellow oil. MS (ISP): m/z=298.2 [M+H]$^+$.

Syntheses of Intermediate Anilines B7 (Via Buchwald-Hartwig Cross Coupling Reaction)
Intermediate B7.4

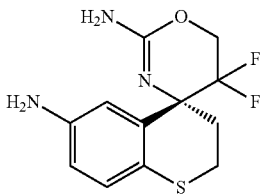

(R)-5,5-Difluoro-5,6-dihydrospiro[[1,3]oxazine-4,4'-thiochroman]-2,6'-diamine a) (R)—N-(bis(4-methoxyphenyl)(phenyl)methyl)-6'-bromo-5,5-difluoro-5,6-dihydrospiro-[[1,3]oxazine-4,4'-thiochroman]-2-amine (intermediate B6.1)

A solution of (R)-6'-bromo-5,5-difluoro-5,6-dihydro spiro [[1,3]oxazine-4,4'-thiochroman]-2-amine (intermediate B6.9) (460 mg, 1.32 mmol) and triethylamine (267 mg, 2.63 mmol) in dichloromethane (10 ml) was cooled to 0° C. and 4,4'-dimethoxytritylchloride (469 mg, 1.38 mmol) was added. The reaction mixture was left to warm to room temperature and stirred for 15 hours. For the workup, the reaction mixture was evaporated and the residue directly purified by chromatography on silica gel using a gradient of heptane/ethyl acetate=0:100 to 60:40 as the eluent. The (R)—N-(bis(4-methoxyphenyl)(phenyl)methyl)-6'-bromo-5,5-difluoro-5,6-dihydrospiro[[1,3]oxazine-4,4'-thiochroman]-2-amine (789 mg, 92% yield) was obtained as a yellow foam. MS (ISP): m/z=651.0 [M+H]$^+$ and 353.0 [M+2+H]$^+$.

b) (R)—N2-(b is (4-methoxyphenyl)(phenyl)methyl)-N6'-(diphenylmethylene)-5,5-difluoro-5,6-dihydro spiro[[1,3]oxazine-4,4'-thiochroman]-2,6'-diamine (intermediate B6.2)

In a dry tube under an atmosphere of argon to a solution of (R)—N-(bis(4-methoxyphenyl)(phenyl)methyl)-6'-bromo-5,5-difluoro-5,6-dihydrospiro[[1,3]oxazine-4,4'-thiochroman]-2-amine (789 mg, 1.21 mmol) in toluene (10 ml) were added consecutively benzophenone imine (439 mg, 2.42 mmol), sodium tert-butoxide (349 mg, 3.63 mmol), 2-di-tert-butylphosphino-2',4',6'-triisopropylbiphenyl {CAS[564483-19-8]} (51.4 mg, 121 µmol), and tris(dibenzylideneacetone)dipalladium(0) chloroform adduct {CAS[52522-40-4]} (37.6 mg, 36.3 µmol). The tube was sealed and the reaction mixture stirred at 110° C. for 15 hours. For the workup, the solvent was evaporated at reduced pressure and the residue purified by chromatography on silica gel using a gradient of heptane/ethyl acetate=0:100 to 70:30 as the eluent. The (R)—N2-(bis(4-methoxyphenyl)(phenyl)methyl)-N6'-(diphenylmethylene)-5,5-difluoro-5,6-dihydrospiro[[1,3]oxazine-4,4'-thiochroman]-2,6'-diamine (613 mg, 67% yield) was obtained as a yellow solid. MS (ISP): m/z=752.5 [M+H]$^+$.

c) (R)-5,5-Difluoro-5,6-dihydro spiro[[1,3]oxazine-4,4'-thiochroman]-2,6'-diamine A solution of (R)—N2-(bis(4-methoxyphenyl)(phenyl)methyl)-N6'-(diphenylmethylene)-5,5-difluoro-5,6-dihydrospiro[[1,3]oxazine-4,4'-thiochroman]-2,6'-diamine (613 mg, 815 µmol) in dichloromethane (10 ml) was treated with trifluoroacetic acid (930 mg, 8.15 mmol). The orange colored solution was stirred at room temperature for 15 hours. Thereafter, the reaction mixture was diluted with dichloromethane (10 ml) and washed with a 1M-solution of sodium carbonate (5 ml). The organic layer was separated, dried over sodium sulphate and evaporated. The resulting yellow oil was dissolved in dioxane (8 ml), then hydrochloric acid (4N in dioxane, 2.04 ml) was added dropwise. A precipitate was formed, which dissolved after addition of hydrochloric acid (4N in dioxane, 2.0 ml). The orange colored solution was stirred at room temperature for 15 hours. For the workup, the solution was evaporated at reduced pressure and the residue dissolved in ethyl acetate (30 ml). The organic layer was washed with hydrochloric acid (1N, 8 ml), the aqueous layer was separated and adjusted to pH 9 by addition of sodium hydroxide (2N). Thereafter, the aqueous layer was extracted with ethyl acetate (3×30 ml), the organic layers combined and dried over sodium sulphate. After evaporation at reduced pressure, the (R)-5,5-difluoro-5,6-dihydro spiro[[1,3]oxazine-4,4'-thiochroman]-2,6'-diamine (230 mg, 89% yield) was obtained as a yellow solid pure enough to be used in the next step without further purification. MS (ISP): m/z=286.1 [M+H]$^+$.

Intermediate B7.5

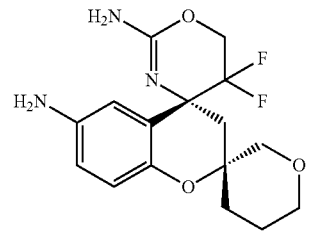 [SMILES: NC1=N[C@@]2(C[C@@]3(CCCOC3)Oc3ccc(N)cc32)C(F)(F)CO1]

In close analogy to the procedure described for the synthesis of Intermediate B7.4, the (2'R,4R)-5,5-difluoro-5,5'',6,6''-tetrahydro-4''H-dispiro[1,3-oxazine-4,4'-chromene-2',3''-pyran]-2,6'-diamine was obtained as follows:

a) (2'R,4R)—N-[bis(4-methoxyphenyl)(phenyl)methyl]-6'-bromo-5,5-difluoro-5,5'',6,6''-tetrahydro-4''H-dispiro[1,3-oxazine-4,4'-chromene-2',3''-pyran]-2-amine Starting from (2'R,4R)-6'-bromo-5,5-difluoro-5,5'',6,6''-tetrahydro-4''H-dispiro[1,3-oxazine-4,4'-chromene-2',3''-pyran]-2-amine (intermediate B6.7), the title compound (80% yield) was obtained as a white foam. MS (ISP): m/z=705.2 [M+H]⁺ and 707.2 [M+2+H]⁺.

b) (2'R,4R)—N~2~-[bis(4-methoxyphenyl)(phenyl) methyl]-N~6~'-(diphenylmethylidene)-5,5-difluoro-5,5'',6,6''-tetrahydro-4''H-dispiro[1,3-oxazine-4,4'-chromene-2',3''-pyran]-2,6'-diamine Starting from (2'R,4R)—N-[bis(4-methoxyphenyl)(phenyl)methyl]-6'-bromo-5,5-difluoro-5,5'',6,6''-tetrahydro-4''H-dispiro[1,3-oxazine-4,4'-chromene-2',3''-pyran]-2-amine, the title compound (54% yield) was obtained as a yellow solid. MS (ISP): m/z=806.5 [M+H]⁺.

c) (2'R,4R)-5,5-difluoro-5,5'',6,6''-tetrahydro-4''H-dispiro[1,3-oxazine-4,4'-chromene-2',3''-pyran]-2,6'-diamine Starting from (2'R,4R)—N~2~-[bis(4-methoxyphenyl)(phenyl)methyl]-N~6~'-(diphenylmethylidene)-5,5-difluoro-5,5'',6,6''-tetrahydro-4''H-dispiro[1,3-oxazine-4,4'-chromene-2',3''-pyran]-2,6'-diamine, the title compound (34% yield) was obtained as a pale yellow solid. MS (ISP): m/z=340.1 [M+H]⁺.

Example 19

(R)-6-(5-Chloropyridin-3-yl)-5',5'-difluoro-5',6'-dihydrospiro[chroman-4,4'-[1,3]oxazin]-2'-amine In a tube a mixture of (R)-6-bromo-5',5'-difluoro-5',6'-dihydrospiro[chroman-4,4'-[1,3]oxazin]-2'-amine (intermediate B6.1) (20 mg, 60 µmol), 5-chloropyridin-3-ylboronic acid (11 mg, 72 µmol), and cesium carbonate (78 mg, 240 µmol) in tetrahydrofuran (1.2 ml) and water (0.59 ml) was purged with argon for 5 minutes. Thereafter, [1,1'-bis(diphenylphosphino)ferrocene]dichloropalladium(II) (2.2 mg, 3.0 µmol) was added, the tube was sealed and the mixture heated at 80° C. for 30 minutes. For the workup, the reaction mixture was diluted with ethyl acetate and washed with water. The organic layer was separated, dried over sodium sulphate and evaporated at reduced pressure. The residue was purified by chromatography on a silica-NH₂ phase using a gradient of heptane/ethyl acetate=100:0 to 0:100 as the eluent. The (R)-5-(2'-amino-4,4,5',5'-tetrafluoro-3,4,5',6'-tetrahydro-2H-spiro [naphthalene-1,4'-[1,3]oxazine]-7-yl)nicotinonitrile (12 mg, 55% yield) was obtained as a pale yellow solid. MS (ISP): m/z=366.0 [M+H]⁺.

Example 20

(R)-6-(3,5-dichlorophenyl)-5',5'-difluoro-5',6'-dihydrospiro[chroman-4,4'-[1,3]oxazin]-2'-amine In a manner analogous to that described in Example 19, the cross coupling reaction of (R)-6-bromo-5',5'-difluoro-5',6'-dihydrospiro[chroman-4,4'-[1,3]oxazin]-2'-amine (intermediate B6.1) with 3,5-dichlorophenylboronic acid yielded the title compound (58% yield) as a pale yellow solid. MS (ISP): m/z=399.1 [M+H]⁺.

Example 21

(R)-5',5'-difluoro-6-(pyrimidin-5-yl)-5',6'-dihydrospiro[chroman-4,4'-[1,3]oxazin]-2'-amine In a manner analogous to that described in Example 19, the cross coupling reaction of (R)-6-bromo-5',5'-difluoro-5',6'-dihydrospiro[chroman-4,4'-[1,3]oxazin]-2'-amine (intermediate B6.1) with pyrimidin-5-ylboronic acid yielded the title compound (55% yield) as a pale yellow solid. MS (ISP): m/z=333.1 [M+H]⁺.

Example 22

(R)-5',5'-difluoro-6-(5-methoxypyridin-3-yl)-5',6'-dihydrospiro[chroman-4,4'-[1,3]oxazin]-2'-amine In a manner analogous to that described in Example 19, the cross coupling reaction of (R)-6-bromo-5',5'-difluoro-5',6'-dihydrospiro[chroman-4,4'-[1,3]oxazin]-2'-amine (intermediate B6.1) with 5-methoxypyridin-3-ylboronic acid yielded the title compound (60% yield) as a pale yellow solid. MS (ISP): m/z=362.2 [M+H]⁺.

Example 23

(2RS,4R)-6-(5-chloropyridin-3-yl)-5',5'-difluoro-2-phenyl-5',6'-dihydrospiro[chroman-4,4'-[1,3]oxazin]-2'-amine In a manner analogous to that described in Example 19, the cross coupling reaction of (2RS,4R)-6-bromo-5',5'-difluoro-2-phenyl-5',6'-dihydrospiro[chroman-4,4'-[1,3]oxazin]-2'-amine (intermediate B6.3) with 5-chloropyridin-3-ylboronic acid yielded the title compound (16% yield) as a grey solid. MS (ISP): m/z=442.3 [M+H]⁺.

Example 24

5-((2RS,4R)-2'-amino-5',5'-difluoro-2-phenyl-5',6'-dihydrospiro[chroman-4,4'-[1,3]oxazine]-6-yl)nicotinonitrile In a manner analogous to that described in Example 19, the cross coupling reaction of (2RS,4R)-6-bromo-5',5'-difluoro-2-phenyl-5',6'-dihydrospiro[chroman-4,4'-[1,3]oxazin]-2'-amine (intermediate B6.3) with 5-cyanopyridin-3-ylboronic acid yielded the title compound (16% yield) as a white solid. MS (ISP): m/z=433.3 [M+H]⁺.

Example 25

(2RS,4R)-5',5'-difluoro-2-phenyl-6-(pyrimidin-5-yl)-5',6'-dihydrospiro[chroman-4,4'-[1,3]oxazin]-2'-amine In a manner analogous to that described in Example 19, the cross coupling reaction of (2RS,4R)-6-bromo-5',5'-difluoro-2-phenyl-5',6'-dihydrospiro[chroman-4,4'-[1,3]oxazin]-2'-amine (intermediate B6.3) with pyrimidin-5-ylboronic acid yielded the title compound (22% yield) as a white solid. MS (ISP): m/z=409.3 [M+H]⁺.

Example 26

(2RS,4R)-6-(3,5-dichlorophenyl)-5',5'-difluoro-2-phenyl-5',6'-dihydrospiro[chroman-4,4'-[1,3]oxazin]-2'-amine In a manner analogous to that described in Example 19, the cross coupling reaction of (2RS,4R)-6-bromo-5',5'-difluoro-2-phenyl-5',6'-dihydrospiro[chroman-4,4'-[1,3]oxazin]-2'-amine (intermediate B6.3) with 3,5-dichlorophenylboronic acid yielded the title compound (17% yield) as a white solid. MS (ISP): m/z=475.0 [M+H]⁺.

Example 27

3-42RS,4R)-2'-amino-5',5'-difluoro-2-phenyl-5',6'-dihydrospiro[chroman-4,4'-[1,3]oxazine]-6-yl)benzonitrile In a manner analogous to that described in Example 19, the cross coupling reaction of (2RS,4R)-6-bromo-5',5'-difluoro-2-phenyl-5',6'-dihydrospiro[chroman-4,4'-[1,3]oxazin]-2'-amine (intermediate B6.3) with 3-cyanophenylboronic acid yielded the title compound (13% yield) as a white solid. MS (ISP): m/z=432.2 [M+H]⁺.

Example 28

(R)-6-(5-chloropyridin-3-yl)-5',5'-difluoro-2,2-dimethyl-5',6'-dihydrospiro[chroman-4,4'-[1,3]oxazin]-2'-amine In a manner analogous to that described in Example 19, the cross coupling reaction of (R)-6-bromo-5',5'-difluoro-2,2-dimethyl-5',6'-dihydrospiro[chroman-4,4'-[1,3]oxazin]-2'-amine (intermediate B6.5) with 5-chloropyridin-3-ylboronic acid yielded the title compound (78% yield) as a white powder. MS (ISP): m/z=394.1 [M+H]⁺.

Example 29

(2'R,4R)-6'-(5-Chloropyridin-3-yl)-5,5-difluoro-5,5",6,6"-tetrahydro-4"H-dispiro[1,3-oxazine-4,4'-chromene-2',3"-pyran]-2-amine formate In a manner analogous to that described in Example 19, the cross coupling reaction of (2'R,4R)-6'-bromo-5,5-difluoro-5,5",6,6"-tetrahydro-4"H-dispiro[1,3-oxazine-4,4'-chromene-2',3"-pyran]-2-amine (intermediate B6.7) with 5-chloropyridin-3-ylboronic acid and chromatography on preparative HPLC yielded the title compound (66% yield) as an off-white, amorphous material. MS (ISP): m/z=436 [M+H]⁺ and 438 [M+2+H]⁺.

Example 30

3-[(2'R,4R)-2-Amino-5,5-difluoro-5,5",6,6"-tetrahydro-4"H-dispiro[1,3-oxazine-4,4'-chromene-2',3"-pyran]-6'-yl]benzonitrile formate In a manner analogous to that described in Example 19, the cross coupling reaction of (2'R,4R)-6'-bromo-5,5-difluoro-5,5",6,6"-tetrahydro-4"H-dispiro[1,3-oxazine-4,4'-chromene-2',3"-pyran]-2-amine (intermediate B6.7) with 3-cyanophenylboronic acid and chromatography on preparative HPLC yielded the title compound (25% yield) as a pale yellow solid. MS (ISP): m/z=426.2 [M+H]⁺.

Example 31

(2'S,4R)-6'-(5-Chloropyridin-3-yl)-5,5-difluoro-5,5",6,6"-tetrahydro-4"H-dispiro[1,3-oxazine-4,4'-chromene-2',3"-pyran]-2-amine formate In a manner analogous to that described in Example 19, the cross coupling reaction of (2'S,4R)-6'-bromo-5,5-difluoro-5,5",6,6"-tetrahydro-4"H-dispiro[1,3-oxazine-4,4'-chromene-2',3"-pyran]-2-amine (intermediate B6.8) with 5-chloropyridin-3-ylboronic acid and chromatography on preparative HPLC yielded the title compound (66% yield) as an off-white, amorphous material. MS (ISP): m/z=436 [M+H]⁺ and 438 [M+2+H]⁺.

Example 32

(R)-6'-(5-Chloropyridin-3-yl)-5,5-difluoro-5,6-dihydrospiro[[1,3]oxazine-4,4'-thiochroman]-2-amine In a manner analogous to that described in Example 19, the cross coupling reaction of (R)-6'-bromo-5,5-difluoro-5,6-dihydrospiro[[1,3]oxazine-4,4'-thiochroman]-2-amine (intermediate B6.9) with 5-chloropyridin-3-ylboronic acid yielded the title compound (70% yield) as a white solid. MS (ISP): m/z=382.0 [M+H]⁺.

General Procedure for the Preparation of Amides of Formula I.4:

A solution of the carboxylic acid (0.23 mmol) in methanol (5 ml) was cooled to 0° C. 4-(4,6-Dimethoxy[1.3.5]triazin-2-yl)-4-methylmorpholinium chloride hydrate (DMTMM) (80 mg, 0.27 mmol) was added and the solution was stirred at 0° C. for 30 minutes. Thereafter, a solution of the intermediate diamine B7 (0.21 mmol) in methanol (5 ml) was added dropwise at 0° C. via syringe. The reaction mixture was stirred at 23° C. for 18-60 hours. For the workup, the reaction mixture was poured into a solution of sodium carbonate (1M) followed by the extraction with ethyl acetate. The organic layer was separated, washed with brine and dried over sodium sulphate. Removal of the solvent at reduced pressure left a residue which was purified by chromatography on silica gel or on a silica-NH₂ phase using a mixture of dichloromethane and methanol (0-10%) to give the pure amides of formula I.

Example 33

(R)—N-(2'-Amino-5',5'-difluoro-5',6'-dihydrospiro[chroman-4,4'-[1,3]oxazine]-6-yl)-5-chloropicolinamide The condensation of (R)-5',5'-difluoro-5',6'-dihydrospiro[chroman-4,4'-[1,3]oxazine]-2',6-diamine (intermediate B7.1) and 5-chloropicolinic acid yielded the title compound (56% yield) as a white solid. MS (ISP): m/z=409.2 [M+H]⁺.

Example 34

(R)—N-(2'-Amino-5',5'-difluoro-5',6'-dihydrospiro[chroman-4,4'-[1,3]oxazine]-6-yl)-5-cyanopicolinamide The condensation of (R)-5',5'-difluoro-5',6'-dihydrospiro[chroman-4,4'-[1,3]oxazine]-2',6-diamine (intermediate B7.1) and 5-cyanopicolinic acid yielded the title compound (74% yield) as a yellow solid. MS (ISP): m/z=400.2 [M+H]⁺.

Example 35

(R)—N-(2'-Amino-5',5'-difluoro-5',6'-dihydrospiro[chroman-4,4'-[1,3]oxazine]-6-yl)-5-cyanopicolinamide The condensation of (R)-5',5'-difluoro-5',6'-dihydrospiro[chroman-4,4'-[1,3]oxazine]-2',6-diamine (intermediate B7.1) and 4-chloro-1H-pyrazole-5-carboxylic acid yielded the title compound (34% yield) as a pale yellow solid. MS (ISP): m/z=398.1 [M+H]$^+$.

Example 36

N-((2R or 2S,4R)-2'-Amino-5',5'-difluoro-2-phenyl-5',6'-dihydrospiro[chroman-4,4'-[1,3]oxazine]-6-yl)-5-chloropicolinamide The condensation of (2RS,4R)-5',5'-difluoro-2-phenyl-5',6'-dihydrospiro[chroman-4,4'-[1,3]oxazine]-2',6-diamine (intermediate B7.2) and 5-chloropicolinic acid yielded the title compound (21% yield) as an off-white solid. MS (ISP): m/z=485.1 [M+H]$^+$.

Example 37

N-((2R or 2S,4R)-2'-Amino-5',5'-difluoro-2-phenyl-5',6'-dihydrospiro[chroman-4,4'-[1,3]oxazine]-6-yl)-5-cyanopicolinamide The condensation of (2RS,4R)-5',5'-difluoro-2-phenyl-5',6'-dihydrospiro[chroman-4,4'-[1,3]oxazine]-2',6-diamine (intermediate B7.2) and 5-cyanopicolinic acid yielded the title compound (33% yield) as an off-white solid. MS (ISP): m/z=476.1 [M+H]$^+$.

Example 38

N-((2R or 2S,4R)-2'-Amino-5',5'-difluoro-2-phenyl-5',6'-dihydrospiro[chroman-4,4'-[1,3]oxazine]-6-yl)-5-fluoropicolinamide The condensation of (2RS,4R)-5',5'-difluoro-2-phenyl-5',6'-dihydrospiro[chroman-4,4'-[1,3]oxazine]-2',6-diamine (intermediate B7.2) and 5-fluoropicolinic acid yielded the title compound (26% yield) as an off-white solid. MS (ISP): m/z=469.2 [M+H]$^+$.

Example 39

N-((2R or 2S,4R)-2'-Amino-5',5'-difluoro-2-phenyl-5',6'-dihydrospiro[chroman-4,4'-[1,3]oxazine]-6-yl)-5-(trifluoromethyl)picolinamide The condensation of (2RS,4R)-5',5'-difluoro-2-phenyl-5',6'-dihydrospiro[chroman-4,4'-[1,3]oxazine]-2',6-diamine (intermediate B7.2) and 5-fluoropicolinic acid yielded the title compound (27% yield) as an off-white solid.

Example 40

(R)—N-(2'-Amino-5',5'-difluoro-2,2-dimethyl-5',6'-dihydrospiro[chroman-4,4'-[1,3]oxazine]-6-yl)-5-chloropicolinamide The condensation of (R)-5',5'-difluoro-2,2-dimethyl-5',6'-dihydrospiro[chroman-4,4'-[1,3]oxazine]-2',6-diamine (intermediate B7.3) and 5-chloropicolinic acid yielded the title compound (85% yield) as a white solid. MS (ISP): m/z=437.1 [M+H]$^+$.

Example 41

(R)—N-(2'-Amino-5',5'-difluoro-2,2-dimethyl-5',6'-dihydrospiro[chroman-4,4'-[1,3]oxazine]-6-yl)-5-cyanopicolinamide The condensation of (R)-5',5'-difluoro-2,2-dimethyl-5',6'-dihydrospiro[chroman-4,4'-[1,3]oxazine]-2',6-diamine (intermediate B7.3) and 5-cyanopicolinic acid yielded the title compound (78% yield) as a yellow solid. MS (ISP): m/z=428.3 [M+H]$^+$.

Example 42

(R)—N-(2-Amino-5,5-difluoro-5,6-dihydrospiro[[1,3]oxazine-4,4'-thiochroman]-6'-yl)-5-chloropicolinamide The condensation of (R)-5',5'-difluoro-2,2-dimethyl-5',6'-dihydrospiro[chroman-4,4'-[1,3]oxazine]-2',6-diamine (intermediate B7.4) and 5-chloropicolinic acid yielded the title compound (55% yield) as a white solid. MS (ISP): m/z=424.9 [M+H]$^+$.

Example 43

(R)—N-(2-Amino-5,5-difluoro-5,6-dihydrospiro[[1,3]oxazine-4,4'-thiochroman]-6'-yl)-5-cyanopicolinamide The condensation of (R)-5',5'-difluoro-2,2-dimethyl-5',6'-dihydrospiro[chroman-4,4'-[1,3]oxazine]-2',6-diamine (intermediate B7.4) and 5-cyanopicolinic acid yielded the title compound (57% yield) as a yellow solid. MS (ISP): m/z=415.9 [M+H]$^+$.

Example 44

N-[(2'R,4R)-2-Amino-5,5-difluoro-5,5'',6,6''-tetrahydro-4''H-dispiro[1,3-oxazine-4,4'-chromene-2',3''-pyran]-6'-yl]-5-cyanopyridine-2-carboxamide The condensation of (2'R,4R)-5,5-difluoro-5,5'',6,6''-tetrahydro-4''H-dispiro[1,3-oxazine-4,4'-chromene-2',3''-pyran]-2,6'-diamine (intermediate B7.5) and 5-cyanopicolinic acid yielded the title compound (64% yield) as a yellow solid. MS (ISP): m/z=470.3 [M+H]$^+$.

Example 45

N-[(4R)-2-amino-5,5-difluoro-1',1'-dioxido-2',3',5,6-tetrahydrospiro[1,3-oxazine-4,4'-thiochromen]-6'-yl]-5-chloropyridine-2-carboxamide A solution of (R)—N-(2-amino-5,5-difluoro-5,6-dihydrospiro[[1,3]oxazine-4,4'-thiochroman]-6'-yl)-5-chloropicolinamide (Example 42) (30 mg, 70.6 μmol) in methanol (2 ml) was treated with potassium peroxomonosulphate (52.1 mg, 84.7 μmol). The suspension was stirred at room temperature for 5 days. For the workup, the reaction mixture was evaporated at reduced pressure and the residue directly purified by chromatography on a silica-NH$_2$ phase using a gradient of heptane/ethyl acetate=100:0 to 20:80 as the eluent. The title compound (30 mg, 93% yield) was obtained as a white solid. MS (ISP): m/z=457.2 [M+H]$^+$.

Example 46

N-[(4R)-2-amino-5,5-difluoro-1',1'-dioxido-2',3',5,6-tetrahydrospiro[1,3-oxazine-4,4'-thiochromen]-6'-yl]-5-cyanoopyridine-2-carboxamide In a manner analogous to that described in Example 45, the oxidation of the N-[(2'R,4R)-2-amino-5,5-difluoro-5,5",6,6"-tetrahydro-4"H-dispiro[1,3-oxazine-4,4'-chromene-2',3"-pyran]-6'-yl]-5-cyanopyridine-2-carboxamide (Example 44) yielded the title compound (74% yield) as a white solid. MS (ISP): m/z=448.2 [M+H]⁺.

Synthesis of the Intermediate Sulfinamide Nitrile C1

General Procedure

A solution of the sulfinamide alcohol A4 (4.1 mmol) in dichloromethane (23 ml) was subsequently treated at 22° C. with 2-bromoacetonitrile (6.2 mmol), silver(I) oxide (1.9 g) and tetrabutylammonium iodide (0.30 g), and stiffing was continued for 2 hours. For the workup, the suspension was filtered and the filtrate was washed with an aqueous saturated solution of sodium hydrogencarbonate. The organic layer was dried and evaporated to give the crude sulfinamide nitrile C1 which was used without further purification.

Intermediate C1.1

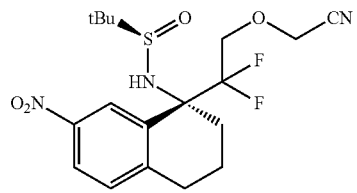 [SMILES: CC(C)(C)[S@@](=O)N[C@]1(C(F)(F)COCC#N)CCCc2ccc([N+](=O)[O-])cc21]

Starting from (R)-2-methyl-propane-2-sulfinic acid [(R)-1-(1,1-difluoro-2-hydroxy-ethyl)-7-nitro-1,2,3,4-tetrahydro-naphthalen-1-yl]-amide (intermediate A4.2), the product (R)-2-methyl-propane-2-sulfinic acid [(R)-1-(2-cyanomethoxy-1,1-difluoro-ethyl)-7-nitro-1,2,3,4-tetrahydro-naphthalen-1-yl]-amide (68% yield) was obtained as a brown oil. MS (ISP): m/z=416.3 [M+H]⁺.

Intermediate C1.2

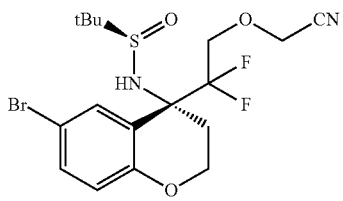 [SMILES: CC(C)(C)[S@@](=O)N[C@]1(C(F)(F)COCC#N)CCOc2ccc(Br)cc21]

Starting from (R)-2-methyl-propane-2-sulfinic acid [(R)-6-bromo-4-(1,1-difluoro-2-hydroxy-ethyl)-chroman-4-yl]-amide (intermediate B4.1), the product (R)-2-methyl-propane-2-sulfinic acid [(R)-6-bromo-4-(2-cyanomethoxy-1,1-difluoro-ethyl)-chroman-4-yl]-amide (64% yield) was obtained as an off-white waxy solid. MS (ISP): m/z=451.0 [M+H]⁺ and 453.0 [M+2+H]⁺.

Intermediate C1.3

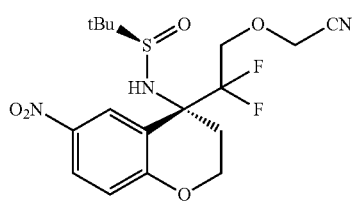 [SMILES: CC(C)(C)[S@@](=O)N[C@]1(C(F)(F)COCC#N)CCOc2ccc([N+](=O)[O-])cc21]

Starting from (R)-2-methyl-propane-2-sulfinic acid [(R)-4-(1,1-difluoro-2-hydroxy-ethyl)-6-nitro-chroman-4-yl]-amide (intermediate B4.2), the product (R)-2-methyl-propane-2-sulfinic acid [(R)-4-(2-cyanomethoxy-1,1-difluoro-ethyl)-6-nitro-chroman-4-yl]-amide (79% yield) was obtained as a brown oil. MS (ISP): m/z=418.2 [M+H]⁺.

Intermediate C1.4

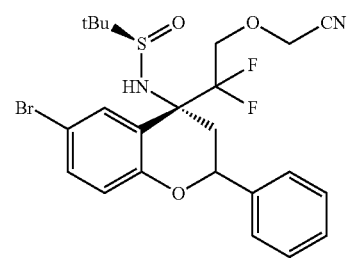

Starting from (R)-2-methyl-propane-2-sulfinic acid [(2RS,4R)-6-bromo-4-(1,1-difluoro-2-hydroxy-ethyl)-2-phenyl-chroman-4-yl]-amide (intermediate B4.3), the product (R)-2-methyl-propane-2-sulfinic acid [(2 S,4R)-6-bromo-4-(2-cyano methoxy-1,1-difluoro-ethyl)-2-phenyl-chroman-4-yl]-amide (79% yield) was obtained as a white solid.

Intermediate C1.5

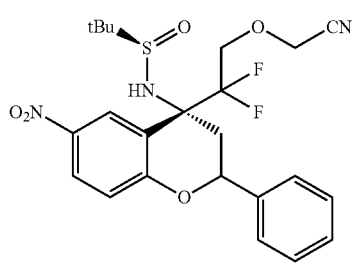

Starting from (R)-2-methyl-propane-2-sulfinic acid [(2RS,4R)-4-(1,1-difluoro-2-hydroxy-ethyl)-6-nitro-2-phenyl-chroman-4-yl]-amide (intermediate B4.4), the product (R)-2-methyl-propane-2-sulfinic acid [(2RS,4R)-4-(2-cyanomethoxy-1,1-difluoro-ethyl)-6-nitro-2-phenyl-chroman-4-yl]-amide (76% yield) was obtained as a sticky yellow liquid.

Synthesis of the Intermediate Amino Nitrile C2

General Procedure

A solution of the sulfinamide nitrile C1 (4.25 mmol) in 1,4-dioxane (20 ml) was treated with a solution of hydrochloric acid in 1,4-dioxane (4 M, 5.3 ml), and stiffing was continued at 22° C. for 1 hour. For the workup, the mixture was diluted with ethyl acetate and washed with a saturated aqueous solution of sodium carbonate. The organic layer was dried and evaporated. The crude material was purified on silica using a mixture of n-heptane and ethyl acetate as the eluent to give the pure amino nitrile C2.

Intermediate C2.1

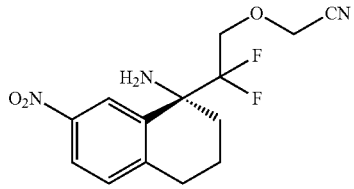

Starting from (R)-2-methyl-propane-2-sulfinic acid [(R)-1-(2-cyanomethoxy-1,1-difluoro-ethyl)-7-nitro-1,2,3,4-tetrahydro-naphthalen-1-yl]-amide (intermediate C1.1), the product [2-((R)-1-amino-7-nitro-1,2,3,4-tetrahydro-naphthalen-1-yl)-2,2-difluoro-ethoxy]-acetonitrile (76% yield) was obtained as a light brown oil. MS (ISP): m/z=312.1 [M+H]$^+$.

Intermediate C2.2

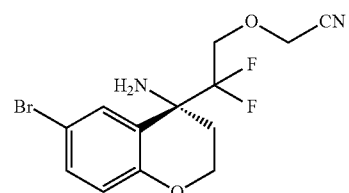

Starting from (R)-2-methyl-propane-2-sulfinic acid [(R)-6-bromo-4-(2-cyanomethoxy-1,1-difluoro-ethyl)-chroman-4-yl]-amide (intermediate C1.2), the product [2-((R)-4-amino-6-bromo-chroman-4-yl)-2,2-difluoro-ethoxy]-acetonitrile (50% yield) was obtained as an off-white oil. MS (ISP): m/z=347.0 [M+H]$^+$ and 349.2 [M+2+H]$^+$.

Intermediate C2.3

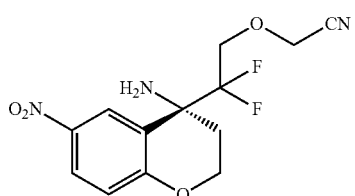 [SMILES: N#CCOCC(F)(F)[C@@]1(N)CCCc2ccc([N+](=O)[O-])cc21]

Starting from (R)-2-methyl-propane-2-sulfinic acid [(R)-4-(2-cyanomethoxy-1,1-difluoro-ethyl)-6-nitro-chroman-4-yl]-amide (intermediate C1.3), the product [2-((R)-4-amino-6-nitro-chroman-4-yl)-2,2-difluoro-ethoxy]-acetonitrile (87% yield) was obtained as a yellow oil. MS (ISP): m/z=313.9 [M+H]$^+$.

Intermediate C2.4

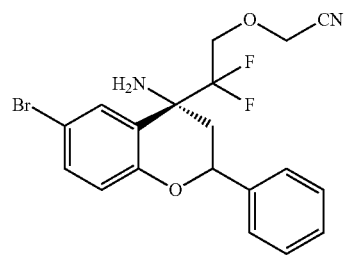

Starting from (R)-2-methyl-propane-2-sulfinic acid [(2RS,4R)-6-bromo-4-(2-cyanomethoxy-1,1-difluoro-ethyl)-2-phenyl-chroman-4-yl]-amide (intermediate C1.4), the product [2-((2RS,4R)-4-amino-6-bromo-2-phenyl-chroman-4-yl)-2,2-difluoro-ethoxy]-acetonitrile (62% yield) was obtained as a pale yellow solid.

Intermediate C2.5

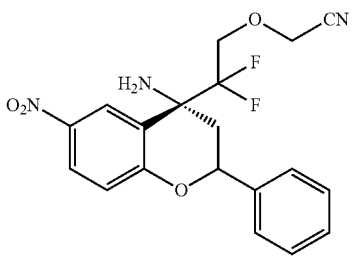

Starting from (R)-2-methyl-propane-2-sulfinic acid [(2RS,4R)-4-(2-cyanomethoxy-1,1-difluoro-ethyl)-6-nitro-2-phenyl-chroman-4-yl]-amide (intermediate C1.5), the product [2-((2RS,4R)-4-amino-6-nitro-2-phenyl-chroman-4-yl)-2,2-difluoro-ethoxy]-acetonitrile (63% yield) was obtained as a brown solid.

Synthesis of the Intermediate 1,4-Oxazepine C3

General Procedure

A solution of the amino nitrile C2 (2.20 mmol) in toluene (38 ml) was treated at 22° C. with a solution of trimethylaluminium in toluene (2 M, 1.2 ml) and the mixture was heated to 80° C. for 1 hour. For the workup, the mixture was cooled to 0° C., diluted with a saturated aqueous solution of sodium carbonate. The aqueous layer was extracted with ethyl acetate, the organic layers were combined, dried, and evaporated. The residue was purified by chromatography on a silica-NH$_2$ phase using a mixture of n-heptane and ethyl acetate as the eluent to give the pure 1,4-oxazepine C3.

Intermediate C3.1

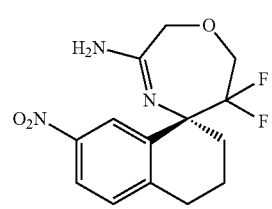 [SMILES: NC1=N[C@@]2(CCCc3ccc([N+](=O)[O-])cc32)C(F)(F)COC1]

Starting from [2-((R)-1-amino-7-nitro-1,2,3,4-tetrahydro-naphthalen-1-yl)-2,2-difluoro-ethoxy]-acetonitrile (intermediate C2.1), the product (R)-6',6'-difluoro-7-nitro-3,4,6',7'- tetrahydro-2H,2'H-spiro[naphthalene-1,5'-[1,4]oxazepin]-3'-amine (70% yield) was obtained as a light brown foam. MS (ISP): m/z=312.1 [M+H]$^+$.

Intermediate C3.2

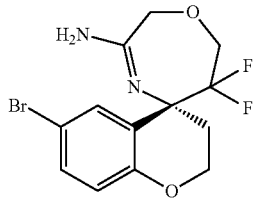 [SMILES: NC1=N[C@@]2(CCOc3ccc(Br)cc32)C(F)(F)COC1]

Starting from [2-((R)-4-amino-6-bromo-chroman-4-yl)-2,2-difluoro-ethoxy]-acetonitrile (intermediate C2.2), the product (R)-6-bromo-6',6'-difluoro-6',7'-dihydro-2'H-spiro[chroman-4,5'-[1,4]oxazepin]-3'-amine was obtained in quantitative yield as an off-white foam. MS (ISP): m/z=347.1 [M+H]$^+$ and 349.1 [M+2+H]$^+$.

Intermediate C3.3

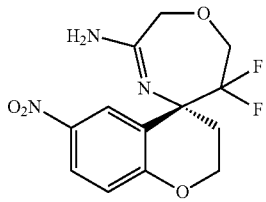 [SMILES: NC1=N[C@@]2(CCOc3ccc([N+](=O)[O-])cc32)C(F)(F)COC1]

Starting from [2-((R)-4-amino-6-nitro-chroman-4-yl)-2,2-difluoro-ethoxy]-acetonitrile (intermediate C2.3), the product (R)-6',6'-difluoro-6-nitro-6',7'-dihydro-2'H-spiro[chroman-4,5'-[1,4]oxazepin]-3'-amine (98% yield) was obtained as a red oil. MS (ISP): m/z=313.9 [M+H]$^+$.

Intermediate C3.4

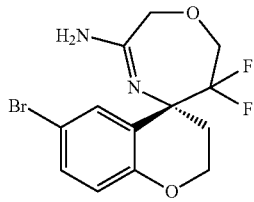 [SMILES: NC1=N[C@@]2(CCOc3ccc(Br)cc32)C(F)(F)COC1]

Starting from [2-((2RS,4R)-4-amino-6-bromo-2-phenyl-chroman-4-yl)-2,2-difluoro-ethoxy]-acetonitrile (intermediate C2.4), the product (2RS,4R)-6-bromo-6',6'-difluoro-2-phenyl-6',7'-dihydro-2'H-spiro[chroman-4,5'-[1,4]oxazepin]-3'-amine (67% yield) was obtained as a yellow semi-solid. MS (ISP): m/z=422.9 [M+H]$^+$.

Intermediate C3.5

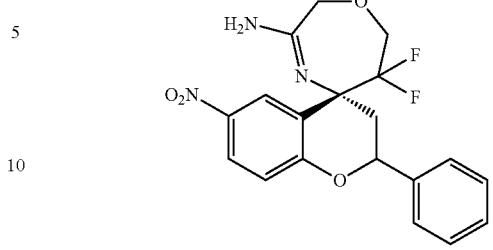

Starting from [2-((2RS,4R)-4-amino-6-nitro-2-phenyl-chroman-4-yl)-2,2-difluoro-ethoxy]-acetonitrile (intermediate C2.5), the product (2RS,4R)-6',6'-difluoro-6-nitro-2-phenyl-6',7'-dihydro-2'H-spiro[chroman-4,5'-[1,4]oxazepin]-3'-amine (37% yield) was obtained as a brown solid. MS (ISP): m/z=390.0 [M+H]$^+$.

Syntheses of Intermediate Anilines C4 (Via Reduction of Nitro 1,4-Oxazepines)

General Procedure

A solution of the nitro oxazepine C3 (3 mmol) in ethanol (31 ml) was hydrogenated at atmospheric pressure using palladium (10% on carbon) (159 mg, 150 μmol) as the catalyst. After 90 minutes the reaction was complete. The reaction mixture was filtrated over a layer of Dicalit, which was washed with ethanol (3×20 ml). The combined solutions of ethanol were evaporated at reduced pressure. The product was engaged in the step without further purification.

Intermediate C4.1

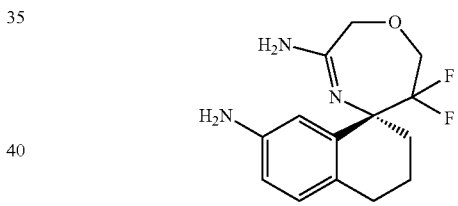

Starting from (R)-6',6'-difluoro-7-nitro-3,4,6',7'-tetrahydro-2H,2'H-spiro[naphthalene-1,5'-[1,4]oxazepin]-3'-amine (intermediate C3.1), the product (R)-6',6'-difluoro-3,4,6',7'-tetrahydro-2H,2'H-spiro[naphthalene-1,5'-[1,4]oxazepine]-3',7-diamine was obtained in quantitative yield as a yellow foam. MS (ISP): m/z=282.2 [M+H]$^+$.

Intermediate C4.2

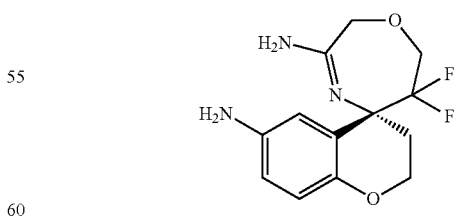

Starting from (R)-6',6'-difluoro-6-nitro-6',7'-dihydro-2'H-spiro[chroman-4,5'-[1,4]oxazepin]-3'-amine (intermediate C3.3), the product (R)-6',6'-difluoro-6',7'-dihydro-2'H-spiro[chroman-4,5'-[1,4]oxazepine]-3',6-diamine (95% yield) was obtained as a yellow solid. MS (ISP): m/z=284.1 [M+H]$^+$.

Intermediate C4.3

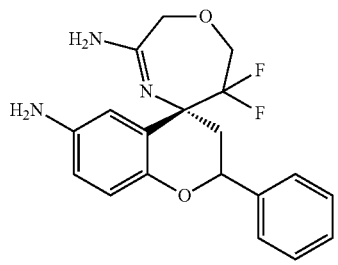

Starting from (2RS,4R)-6',6'-difluoro-6-nitro-2-phenyl-6',7'-dihydro-2'H-spiro[chroman-4,5'-[1,4]oxazepin]-3'-amine (intermediate C3.5), the product (2RS,4R)-6',6'-difluoro-2-phenyl-6',7'-dihydro-2'H-spiro[chroman-4,5'-[1,4]oxazepine]-3',6-diamine (54% yield) was obtained as a brown solid. MS (ISP): m/z=360.0 $[M+H]^+$.

In analogy to the general procedure for the preparation of amides of formula I, the reaction of the intermediate anilines of formula C4 with acids by 4-(4,6-dimethoxy[1.3.5]triazin-2-yl)-4-methylmorpholinium chloride hydrate (DMTMM) as the condensating agent yielded the following compounds:

Example 47

(R)—N-(3'-Amino-6',6'-difluoro-3,4,6',7'-tetrahydro-2H,2'H-spiro[naphthalene-1,5'-[1,4]oxazepine]-7-yl)-5-cyanopicolinamide The condensation of (R)-6',6'-difluoro-3,4,6',7'-tetrahydro-2H,2'H-spiro[naphthalene-1,5'-[1,4]oxazepine]-3',7-diamine (intermediate C4.1) and 5-cyanopicolinic acid yielded the title compound (37% yield) as an off-white solid. MS (ISP): m/z=412.2 $[M+H]^+$.

Example 48

(R)—N-(3'-Amino-6',6'-difluoro-3,4,6',7'-tetrahydro-2H,2'H-spiro[naphthalene-1,5'-[1,4]oxazepine]-7-yl)-5-chloropicolinamide The condensation of (R)-6',6'-difluoro-3,4,6',7'-tetrahydro-2H,2'H-spiro[naphthalene-1,5'-[1,4]oxazepine]-3',7-diamine (intermediate C4.1) and 5-chloropicolinic acid yielded the title compound (45% yield) as an off-white solid. MS (ISP): m/z=421.1 $[M+H]^+$.

Example 49

(R)—N-(3'-Amino-6',6'-difluoro-6',7'-dihydro-2'H-spiro[chroman-4,5'-[1,4]oxazepine]-6-yl)-5-cyanopicolinamide The condensation of (R)-6',6'-difluoro-6',7'-dihydro-2'H-spiro[chroman-4,5'-[1,4]oxazepine]-3',6-diamine (intermediate C4.2) and 5-cyanopicolinic acid yielded the title compound (51% yield) as a yellow solid. MS (ISP): m/z=414.3 $[M+H]^+$.

Example 50

(R)—N-(3'-Amino-6',6'-difluoro-6',7'-dihydro-2'H-spiro[chroman-4,5'-[1,4]oxazepine]-6-yl)-5-chloropicolinamide The condensation of (R)-6',6'-difluoro-6',7'-dihydro-2'H-spiro[chroman-4,5'-[1,4]oxazepine]-3',6-diamine (intermediate C4.2) and 5-chloropicolinic acid yielded the title compound (54% yield) as a pale yellow solid. MS (ISP): m/z=423.2 $[M+H]^+$.

Example 51

(R)—N-(3'-Amino-6',6'-difluoro-6',7'-dihydro-2'H-spiro[chroman-4,5'-[1,4]oxazepine]-6-yl)-3,5-dichloropicolinamido The condensation of (R)-6',6'-difluoro-6',7'-dihydro-2'H-spiro[chroman-4,5'-[1,4]oxazepine]-3',6-diamine (intermediate C4.2) and 3,5-chloropicolinic acid yielded the title compound (38% yield) as a pale yellow solid. MS (ISP): m/z=457.2 $[M+H]^+$ and 459.2 $[M+2+H]^+$.

Example 52

N-((2RS,4R)-3'-Amino-6',6'-difluoro-2-phenyl-6',7'-dihydro-2'H-spiro[chroman-4,5'-[1,4]oxazepine]-6-yl)-5-(trifluoromethyl)picolinamide The condensation of (2RS,4R)-6',6'-difluoro-2-phenyl-6',7'-dihydro-2'H-spiro[chroman-4,5'-[1,4]oxazepine]-3',6-diamine (intermediate C4.3) and 5-trifluoromethyl-pyridine-2-carboxylic acid yielded the title compound (7% yield) as a light brown solid. MS (ISP): m/z=532.8 $[M+H]^+$.

Example 53

N-((2RS,4R)-3'-Amino-6',6'-difluoro-2-phenyl-6',7'-dihydro-2'H-spiro[chroman-4,5'-[1,4]oxazepine]-6-yl)-5-cyanopicolinamide The condensation of (2RS,4R)-6',6'-difluoro-2-phenyl-6',7'-dihydro-2'H-spiro[chroman-4,5'-[1,4]oxazepine]-3',6-diamine (intermediate C4.3) and 5-cyanopicolinic acid yielded the title compound as an off-white solid. MS (ISP): m/z=490.2 $[M+H]^+$. In a manner analogous to that described in Example 19, the following compounds were obtained:

Example 54

(R)-6-(5-Chloropyridin-3-yl)-6',6'-difluoro-6',7'-dihydro-2'H-spiro[chroman-4,5'-[1,4]oxazepin]-3'-amine The cross coupling reaction of (R)-6-bromo-6',6'-difluoro-6',7'-dihydro-2'H-spiro[chroman-4,5'-[1,4]oxazepin]-3'-amine (intermediate C3.2) with 5-chloropyridin-3-ylboronic acid yielded the title compound (35% yield) as a light brown, amorphous material. MS (ISP): m/z=380.2 $[M+H]^+$.

Example 55

(R)-6-(3,5-Dichlorophenyl)-6',6'-difluoro-6',7'-dihydro-2'H-spiro[chroman-4,5'-[1,4]oxazepin]-3'-amine The cross coupling reaction of (R)-6-bromo-6',6'-difluoro-6',7'-dihydro-2'H-spiro[chroman-4,5'-[1,4]oxazepin]-3'-amine (intermediate C3.2) with 3,5-dichlorophenylboronic acid yielded the title compound (40% yield) as a light brown foam. MS (ISP): m/z=413.2 [M+H]⁺ and 415.2 [M+2+H]⁺.

Example 56

(2RS,4R)-6-(5-Chloropyridin-3-yl)-6',6'-difluoro-2-phenyl-6',7'-dihydro-2'H-spiro[chroman-4,5'-[1,4]oxazepin]-3'-amine The cross coupling reaction of (2RS,4R)-6-bromo-6',6'-difluoro-2-phenyl-6',7'-dihydro-2'H-spiro[chroman-4,5'-[1,4]oxazepin]-3'-amine (intermediate C3.4) with 5-chloropyridin-3-ylboronic acid yielded the title compound (7% yield) as a white solid.

Example 57

(2RS,4R)-6-(3,5-Dichlorophenyl)-6',6'-difluoro-2-phenyl-6',7'-dihydro-2'H-spiro[chroman-4,5'-[1,4]oxazepin]-3'-amine The cross coupling reaction of (2RS,4R)-6-bromo-6',6'-difluoro-2-phenyl-6',7'-dihydro-2'H-spiro[chroman-4,5'-[1,4]oxazepin]-3'-amine (intermediate C3.4) with 3,5-dichlorophenylboronic acid yielded the title compound (8% yield) as a white solid. MS (ISP): m/z=489.4 [M+H]⁺.

Example 58

(2RS,4R)-6',6'-difluoro-2-phenyl-6-(pyrimidin-5-yl)-6',7'-dihydro-2'H-spiro[chroman-4,5'-[1,4]oxazepin]-3'-amine The cross coupling reaction of (2RS,4R)-6-bromo-6',6'-difluoro-2-phenyl-6',7'-dihydro-2'H-spiro[chroman-4,5'-[1,4]oxazepin]-3'-amine (intermediate C3.4) with pyrimidin-5-ylboronic acid yielded the title compound (12% yield). MS (ISP): m/z=423.0 [M+H]⁺.

Example 59

5-((2RS,4R)-3'-amino-6',6'-difluoro-2-phenyl-6',7'-dihydro-2'H-spiro[chroman-4,5'-[1,4]oxazepine]-6-yl)nicotinonitrile The cross coupling reaction of (2RS,4R)-6-bromo-6',6'-difluoro-2-phenyl-6',7'-dihydro-2'H-spiro[chroman-4,5'-[1,4]oxazepin]-3'-amine (intermediate C3.4) with 5-cyanopyridin-3-ylboronic acid yielded the title compound (15% yield) as a colorless solid. MS (ISP): m/z=447.4 [M+H]⁺.

Example 60

3-((2RS,4R)-3'-amino-6',6'-difluoro-2-phenyl-6',7'-dihydro-2'H-spiro[chroman-4,5'-[1,4]oxazepine]-6-yl)benzonitrile The cross coupling reaction of (2RS,4R)-6-bromo-6',6'-difluoro-2-phenyl-6',7'-dihydro-2'H-spiro[chroman-4,5'-[1,4]oxazepin]-3'-amine (intermediate C3.4) with 3-cyanophenylboronic acid yielded the title compound (10% yield) as a colorless solid. MS (ISP): m/z=446.0 [M+H]⁺.

The invention claimed is:
1. A compound of formula I,

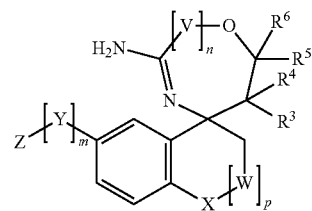

wherein
V is —$CR^{7a}R^{7b}$—;
W is —$CR^{2a}R^{2b}$—;
X is —$CR^{1a}R^{1b}$—; —O—, —S— or —$SO_2$—;
Y —NH—C=O—;
Z is selected from the group consisting of
heteroaryl substituted by 1-4 substituents individually selected from $R^8$,
aryl, and
aryl substituted by 1-4 substituents individually selected from $R^8$;
$R^{1a}$ is selected from the group consisting of
hydrogen,
halogen, and
$C_{1-6}$-alkyl;
$R^{1b}$ is selected from the group consisting of
hydrogen,
halogen, and
$C_{1-6}$-alkyl;
$R^{2a}$ is selected from the group consisting of
hydrogen, and
$C_{1-6}$-alkyl;
$R^{2b}$ is selected from the group consisting of
hydrogen,
aryl, and $C_{1-6}$-alkyl;
or $R^{2a}$ and $R^{2b}$ together with the C to which they are attached form a heterocyclyl;
$R^3$ is
halogen,
$R^4$ is selected from the group consisting of
hydrogen, and
halogen,
$R^5$ is selected from the group consisting of
hydrogen and
$C_{1-6}$-alkyl;
$R^6$ is selected from the group consisting of
hydrogen and
$C_{1-6}$-alkyl;
$R^{7a}$ is selected from the group consisting of
hydrogen and
$C_{1-6}$-alkyl;
$R^{7b}$ is selected from the group consisting of
hydrogen and
$C_{1-6}$-alkyl;
$R^8$ is selected from the group consisting of
cyano,
cyano-$C_{1-6}$-alkyl,
halogen,
halogen-$C_{1-6}$-alkoxy,
halogen-$C_{1-6}$-alkyl,
$C_{1-6}$-alkoxy,
$C_{1-6}$-alkoxy-$C_{1-6}$-alkyl,
$C_{2-6}$-alkynyl, and $C_{1-6}$-alkyl;
n is 0;
m is 0 or 1; and
p is 0 or 1;
or a pharmaceutically acceptable salt thereof.

2. The compound of claim 1, wherein
V is —$CR^{7a}R^{7b}$—;
W is —$CR^{2a}R^{2b}$—;
X is —$CR^{1a}R^{1b}$—; —O—, —S— or —$SO_2$—;
Y —NH—C=O—;
Z is selected from the group consisting of
heteroaryl substituted by 1-2 substituents individually selected from $R^8$, and
aryl substituted by 1-2 substituents individually selected from $R^8$;
$R^{1a}$ is selected from the group consisting of
hydrogen,
halogen, and
$C_{1-6}$-alkyl;
$R^{1b}$ is selected from the group consisting of
hydrogen,
halogen, and
$C_{1-6}$-alkyl;
$R^{2a}$ is selected from the group consisting of
hydrogen and
$C_{1-6}$-alkyl;
$R^{2b}$ is selected from the group consisting of
hydrogen,
phenyl, and
or $R^{2a}$ and $R^{2b}$ together with the C to which they are attached form tetrahydropyranyl;
$R^3$ is halogen;
$R^4$ is halogen;
$R^5$ is hydrogen;
$R^6$ is hydrogen;
$R^{7a}$ is hydrogen;
$R^{7b}$ is hydrogen;
$R^8$ is selected from the group consisting of
cyano,
halogen,
halogen-$C_{1-6}$-alkyl, and
$C_{1-6}$-alkoxy;
n is 0;
m is 0 or 1; and
p is 0 or 1;
or a pharmaceutically acceptable salt thereof.

3. The compound of claim 1, wherein X is —$CR^{1a}R^{1b}$— and $R^{1a}$ and $R^{1b}$ are both hydrogen.

4. The compound of claim 1, wherein p is 0.

5. The compound of claim 1, wherein X is —O—.

6. The compound of claim 1, wherein p is 1, W is —$CR^{2a}R^{2b}$ and $R^{2a}$ and $R^{2b}$ are both hydrogen.

7. The compound of claim 1, wherein $R^3$ is F.

8. The compound of claim 1, wherein $R^4$ is halogen.

9. The compound of claim 8, wherein $R^4$ is F.

10. The compound of claim 1, wherein $R^5$ is hydrogen.

11. The compound of claim 1, wherein $R^6$ is hydrogen.

12. The compound of claim 1, wherein m is 0.

13. The compound of claim 1, wherein m is 1.

14. The compound of claim 1, wherein Z is heteroaryl substituted by halogen or cyano.

15. The compound of claim 1, selected from the group consisting of
(R)-7-(5-chloropyridin-3-yl)-5',5'-difluoro-3,4,5',6'-tetrahydro-2H-spiro[naphthalene-1,4'-[1,3]oxazin]-2'-amine,
(2R,4R)-6'-(5-chloropyridin-3-yl)-5,5-difluoro-5,5",6,6"-tetrahydro-4"H-dispiro[1,3-oxazine-4,4'-chromene-2',3'-pyran]-2-amine formate,
(2RS,4R)-6-(3,5-dichlorophenyl)-5',5'-difluoro-2-phenyl-5',6'-dihydrospiro[chroman-4,4'-[1,3]oxazin]-2'-amine,
(2RS,4R)-6-(5-chloropyridin-3-yl)-5',5'-difluoro-2-phenyl-5',6'-dihydrospiro[chroman-4,4'-[1,3]oxazin]-2'-amine,
(2S,4R)-6'-(5-chloropyridin-3-yl)-5,5-difluoro-5,5",6,6"-tetrahydro-4"H-dispiro[1,3-oxazine-4,4'-chromene-2',3'-pyran]-2-amine formate, and
(R)-3-(2'-amino-5',5'-difluoro-2,3,5',6'-tetrahydrospiro[indene-1,4'-[1,3]oxazine]-6-yl)benzonitrile.

16. The compound of claim 1, selected from the group consisting of
(R)-4,4,5',5'-tetrafluoro-7-(5-fluoropyridin-3-yl)-3,4,5',6'-tetrahydro-2H-spiro[naphthalene-1,4'-[1,3]oxazin]-2'-amine,
(R)-5-(2'-amino-4,4,5',5'-tetrafluoro-3,4,5',6'-tetrahydro-2H-spiro[naphthalene-1,4'-[1,3]oxazine]-7-yl)nicotinonitrile,
(R)-5-(2'-amino-5',5'-difluoro-2,3,5',6'-tetrahydrospiro[indene-1,4'-[1,3]oxazine]-6-yl)nicotinonitrile,
(R)-5-(2'-amino-5',5'-difluoro-3,4,5',6'-tetrahydro-2H-spiro[naphthalene-1,4'-[1,3]oxazine]-7-yl)nicotinonitrile,
(R)-5',5'-difluoro-6-(5-methoxypyridin-3-yl)-5',6'-dihydrospiro[chroman-4,4'-[1,3]oxazin]-2'-amine,
(R)-6-(2-chloropyridin-4-yl)-5',5'-difluoro-2,3,5',6'-tetrahydrospiro[indene-1,4'-[1,3]oxazin]-2'-amine,
(R)-6-(3,5-dichlorophenyl)-5',5'-difluoro-2,3,5',6'-tetrahydrospiro[indene-1,4'-[1,3]oxazin]-2'-amine, and
(R)-6-(3,5-dichlorophenyl)-5',5'-difluoro-5',6'-dihydrospiro[chroman-4,4'-[1,3]oxazin]-2'-amine.

17. The compound of claim 1, selected from the group consisting of (R)-6-(5-chloropyridin-3-yl)-5',5'-difluoro-2,2-dimethyl-5',6'-dihydrospiro[chroman-4,4'-[1,3]oxazin]-2'-amine,
(R)-6-(5-chloropyridin-3-yl)-5',5'-difluoro-2,3,5',6'-tetrahydrospiro[indene-1,4'-[1,3]oxazin]-2'-amine,
(R)-6'-(5-chloropyridin-3-yl)-5,5-difluoro-5,6-dihydrospiro[[1,3]oxazine-4,4'-thiochroman]-2-amine,
(R)-6-(5-chloropyridin-3-yl)-5',5'-difluoro-5',6'-dihydrospiro[chroman-4,4'-[1,3]oxazin]-2'-amine,
(R)-7-(5-chloropyridin-3-yl)-4,4,5',5'-tetrafluoro-3,4,5',6'-tetrahydro-2H-spiro[naphthalene-1,4'-[1,3]oxazin]-2'-amine,
(R)—N-(2'-amino-5',5'-difluoro-2,2-dimethyl-5',6'-dihydrospiro[chroman-4,4'-[1,3]oxazine]-6-yl)-5-chloropicolinamide,
(R)—N-(2'-amino-5',5'-difluoro-2,2-dimethyl-5',6'-dihydrospiro[chroman-4,4'-[1,3]oxazine]-6-yl)-5-cyanopicolinamide, and
(R)—N-(2'-amino-5',5'-difluoro-2,3,5',6'-tetrahydrospiro[indene-1,4'-[1,3]oxazine]-6-yl)-5-cyanopicolinamide.

18. The compound of claim 1, selected from the group consisting of
(R)—N-(2'-amino-5',5'-difluoro-2,3,5',6'-tetrahydrospiro[indene-1,4'-[1,3]oxazine]-6-yl)-5-chloropicolinamide,
(R)—N-(T-amino-5',5'-difluoro-2,3,5',6'-tetrahydrospiro[indene-1,4'-[1,3]oxazine]-6-yl)-5-fluoropicolinamide,
(R)—N-(2'-amino-5',5'-difluoro-2,3,5',6'-tetrahydrospiro[indene-1,4'-[1,3]oxazine]-6-yl)-5-(trifluoromethyl)picolinamide,
(R)—N-(2'-amino-5',5'-difluoro-3,4,5',6'-tetrahydro-2H-spiro[naphthalene-1,4'-[1,3]oxazine]-7-yl)-5-chloropicolinamide, (R)—N-(2'-amino-5',5'-difluoro-3,4,5',6'-tetrahydro-2H-spiro[naphthalene-1,4'-[1,3]oxazine]-7-yl)-5-cyanopicolinamide, (R)—N-(T-amino-5',5'-difluoro-4,4-dimethyl-3,4,5',6'-tetrahydro-2H-spiro[naphthalene-1,4'-[1,3]oxazine]-7-yl)-5-cyanopicolinamide, (R)—N-(2-amino-5,5-difluoro-5,6-dihydrospiro[[1,3]oxazine-4,4'-thiochroman]-6'-yl)-5-chloropicolinamide, (R)—N-(2-amino-5,5-difluoro-5,6-dihydrospiro[[1,3]oxazine-4,4'-thiochroman]-6'-yl)-5-cyanopicolinamide, (R)—N-(2'-amino-5',5'-difluoro-5',6'-dihydrospiro[chroman-4,4'-[1,3]oxazine]-6-yl)-5-chloropicolinamide, and (R)—N-(2'-amino-5',5'-difluoro-5',6'-dihydrospiro[chroman-4,4'-[1,3]oxazine]-6-yl)-5-cyanopicolinamide.

19. The compound of claim 1, selected from the group consisting of (R)—N-(2'-amino-5',5'-difluoro-5',6'-dihydrospiro[chroman-4,4'-[1,3]oxazine]-6-yl)-4-chloro-1H-pyrazole-5-carboxamide, 3-((2RS,4R)-2'-amino-5',5'-difluoro-2-phenyl-5',6'-dihydrospiro[chroman-4,4'-[1,3]oxazine]-6-yl)benzonitrile, 3-[(2'R,4R)-2-amino-5,5-difluoro-5,5'',6,6''-tetrahydro-4''H-dispiro[1,3-oxazine-4,4'-chromene-2',3'-pyran]-6'-yl]benzonitrile formate, and 5-((2RS,4R)-2'-amino-5',5'-difluoro-2-phenyl-5',6'-dihydrospiro[chroman-4,4'-[1,3]oxazine]-6-yl)nicotinonitrile.

20. The compound of claim 1, selected from the group consisting of

N-((2R or 2S,4R)-2'-amino-5',5'-difluoro-2-phenyl-5',6'-dihydrospiro[chroman-4,4'-[1,3]oxazine]-6-yl)-5-chloropicolinamide, N-((2R or 2S,4R)-2'-amino-5',5'-difluoro-2-phenyl-5',6'-dihydrospiro[chroman-4,4'-[1,3]oxazine]-6-yl)-5-cyanopicolinamide, N-((2R or 2S,4R)-2'-amino-5',5'-difluoro-2-phenyl-5',6'-dihydrospiro[chroman-4,4'-[1,3]oxazine]-6-yl)-5-fluoropicolinamide, N-((2R or 2S,4R)-2'-amino-5',5'-difluoro-2-phenyl-5',6'-dihydrospiro[chroman-4,4'-[1,3]oxazine]-6-yl)-5-(trifluoromethyl)picolinamide, N-[(2'R,4R)-2-amino-5,5-difluoro-5,5'',6,6''-tetrahydro-4''H-dispiro[1,3-oxazine-4,4'-chromene-2',3'-pyran]-6'-yl]-5-cyanopyridine-2-carboxamide, N-[(4R)-2-amino-5,5-difluoro-1',1'-dioxido-2',3',5,6-tetrahydrospiro[1,3-oxazine-4,4'-thiochromen]-6'-yl]-5-chloropyridine-2-carboxamide, and N-[(4R)-2-amino-5,5-difluoro-1',1'-dioxido-2',3',5,6-tetrahydrospiro[1,3-oxazine-4,4'-thiochromen]-6'-yl]-5-cyanopyridine-2-carboxamide.

21. The compound of claim 1, selected from the group consisting of (R)—N-(2'-amino-5',5'-difluoro-2,3,5',6'-tetrahydrospiro[indene-1,4'-[1,3]oxazine]-6-yl)-5-cyanopicolinamide, (R)-6-(5-chloropyridin-3-yl)-5',5'-difluoro-5',6'-dihydrospiro[chroman-4,4'-[1,3]oxazin]-2'-amine, (R)—N-(2'-amino-5',5'-difluoro-2,3,5',6'-tetrahydrospiro[indene-1,4'-[1,3]oxazine]-6-yl)-5-chloropicolinamide, and (R)—N-(2'-amino-5',5'-difluoro-2,3,5',6'-tetrahydrospiro[indene-1,4'-[1,3]oxazine]-6-yl)-5-fluoropicolinamide.

22. A pharmaceutical composition comprising a therapeutically effective amount of a compound of formula I

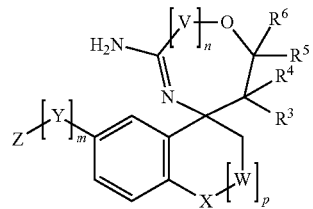

wherein
V is —CR$^{7a}$R$^{7b}$—;
W is —CR$^{2a}$R$^{2b}$—;
X is —CR$^{1a}$R$^{1b}$—; —O—, —S— or —SO$_2$—;
Y —NH—C=O—;
Z is selected from the group consisting of
heteroaryl substituted by 1-4 substituents individually selected from R$^8$,
aryl, and
aryl substituted by 1-4 substituents individually selected from R$^8$;
R$^{1a}$ is selected from the group consisting of
hydrogen,
halogen, and
C$_{1-6}$-alkyl;
R$^{1b}$ is selected from the group consisting of
hydrogen,
halogen, and
C$_{1-6}$-alkyl;
R$^{2a}$ is selected from the group consisting of
hydrogen, and
C$_{1-6}$-alkyl;
R$^{2b}$ is selected from the group consisting of
hydrogen,
aryl, and
C$_{1-6}$-alkyl;
or R$^{2a}$ and R$^{2b}$ together with the C to which they are attached form a heterocyclyl;
R$^3$ is
halogen,
R$^4$ is selected from the group consisting of
hydrogen, and
halogen,
R$^5$ is selected from the group consisting of
hydrogen and
C$_{1-6}$-alkyl;
R$^6$ is selected from the group consisting of
hydrogen and
C$_{1-6}$-alkyl;
R$^{7a}$ is selected from the group consisting of
hydrogen and
C$_{1-6}$-alkyl;
R$^{7b}$ is selected from the group consisting of
hydrogen and
C$_{1-6}$-alkyl;
R$^8$ is selected from the group consisting of
cyano,
cyano-C$_{1-6}$-alkyl,
halogen,
halogen-C$_{1-6}$-alkoxy,
halogen-C$_{1-6}$-alkyl,
C$_{1-6}$-alkoxy,
C$_{1-6}$-alkoxy-C$_{1-6}$-alkyl,
C$_{2-6}$-alkynyl, and
n is 0;

m is 0 or 1; and
p is 0 or 1;
or a pharmaceutically acceptable salt thereof and a pharmaceutically acceptable carrier.

* * * * *